US010376244B1

(12) United States Patent
Cancelos et al.

(10) Patent No.: US 10,376,244 B1
(45) Date of Patent: Aug. 13, 2019

(54) APPARATUS FOR MONITORING THE PRESENCE, AMOUNT AND SIZE OF BUBBLES IN THE BLOODSTREAM AND/OR TISSUE OF A PERSON AND METHOD OF USING THE SAME

(71) Applicants: Silvina Cancelos, Rincon, PR (US); Carlos Javier Marin, Rincon, PR (US); Andrés Saavedra, Mayaguez, PR (US)

(72) Inventors: Silvina Cancelos, Rincon, PR (US); Carlos Javier Marin, Rincon, PR (US); Andrés Saavedra, Mayaguez, PR (US)

(73) Assignee: University of Puerto Rico, San Juan, PR (US)

( * ) Notice: Subject to any disclaimer, the term of this patent is extended or adjusted under 35 U.S.C. 154(b) by 0 days.

(21) Appl. No.: 14/862,093

(22) Filed: Sep. 22, 2015

Related U.S. Application Data

(60) Provisional application No. 62/053,258, filed on Sep. 22, 2014.

(51) Int. Cl.
*A61B 7/04* (2006.01)
*A61B 10/00* (2006.01)
(Continued)

(52) U.S. Cl.
CPC .............. *A61B 8/5223* (2013.01); *A61B 7/04* (2013.01); *A61B 8/4494* (2013.01); *G06K 9/00523* (2013.01); *G06K 9/00536* (2013.01); *G06K 9/6223* (2013.01); *G06K 9/6232* (2013.01); *G06K 9/6267* (2013.01); *G06K 9/6269* (2013.01)

(58) Field of Classification Search
None
See application file for complete search history.

(56) References Cited

U.S. PATENT DOCUMENTS

| 6,408,679 B1 * | 6/2002 | Kline-Schoder | A61B 8/08 73/19.03 |
| 8,055,330 B2 * | 11/2011 | Egozi | A61B 5/0059 600/473 |
| 2003/0233044 A1 * | 12/2003 | Brock-Fisher | A61B 8/481 600/437 |

OTHER PUBLICATIONS

T. G. Leighton, D. G. Ramble, A. D. Phelps, C. L. Morfey, P. P. Harris; Acoustic Detection of Gas Bubbles in a Pipe; Sep. 1998; Acustica-acta acustica; Institute of Sound and Vibration Research, University of Southampton; vol. 84; pp. 801-814. (Year: 1998).*

(Continued)

*Primary Examiner* — Daniel J Colilla
(74) *Attorney, Agent, or Firm* — Hoglund & Pamias, PSC; Roberto J. Rios

(57) ABSTRACT

Decompression sickness (DCS) occurs when divers rise to the surface exposing the body to sudden changes in pressure, generating nitrogen bubbles in tissues, causing serious bodily injury and even death. Therefore, the present invention allows prevention of DCS with a method that detects the presence of bubbles in real time. The invention proposes a new method for bubble detection with a piezoelectric ring (PZT) and pill microphones (PM) placed around a divers thigh. The electrical signals from the piezoelectric ring (PZT) and microphones (PM) are the inputs to a pattern recognition algorithm used for determining the presence, amount and size of bubbles.

20 Claims, 61 Drawing Sheets

(51) Int. Cl.
*A61B 8/08* (2006.01)
*G06K 9/00* (2006.01)
*G06K 9/62* (2006.01)
*A61B 8/00* (2006.01)

(56) References Cited

OTHER PUBLICATIONS

Georges L. Chahine, Greg Loraine; Michel Tanguay; Dynaflow, Inc.; Acoustic Measurements Bubbles in Biological Tissue; Feb. 2009; Journal of Hydrodynamics; 21(1); pp. 47-64. (Year: 2009).*
Francisco I. Valentin, Silvina Cancelos; Detecting presence of bubbles within simulated blood vessels using a piezoelectrtic ring set to oscillate at matching resonant conditions; Proceedings of the ASME 2012 Summer Bioengineering Conference; Jun. 20-23, 2012, Fajardo, Puerto Rico. (Year: 2012).*
C. L. Christman, P. W. Cartron, E. T. Flynn, P. K. Weathersby; In vivo microbubble detection in decompression sickness using a second harmonic resonant bubble detector; Mar. 1986; Undersea Biomedical Research, vol. 13, No. 1., pp. 1-18. (Year: 1986).*

* cited by examiner

APPARATUS FOR MONITORING THE PRESENCE, AMOUNT AND SIZE OF BUBBLES IN THE BLOODSTREAM AND/OR TISSUE OF A PERSON AND METHOD OF USING THE SAME

GOVERNMENT INTEREST

The claimed invention was made with U.S. Government support under grant number W911NF1110135 awarded by the U.S. Army. The government has certain rights in this invention.

BACKGROUND OF THE INVENTION

Diving is the action where an individual immerses himself in water (sea, lake or river) to carry out marine-related activities, rescue operations, structure repairs, among others. Like any other activity, there are risks. Some might be present by the complexity of the work and others might be avoided by following certain safety rules. Nevertheless, diving in and of itself represents exposure to a dangerous disease called decompression sickness.

Decompression sickness (DCS) is a disease that occurs with the sudden loss of pressure which generates small bubbles. These bubbles (nitrogen bubbles), formed in blood and other tissues, are seen in divers who surface too quickly. DCS can occur when diving at approximate depths of 60 to 65 meters. As a safety precaution, a level of monitoring should be performed at a depth of 30-40 meters to identify the diver's condition and avoid unnecessary risks. Monitoring is important since this phenomenon may cause temporary paralysis, permanent injury or death. In 1878, a French scientist named Paul Bert, demonstrated the formation of bubbles in tissues and proposed the idea of a slow ascent to the surface. The symptoms associated with decompression can be divided into two types.

Type I is usually characterized by pain in the joints with mottling of the skin producing a red or purplish-blue tinge, fatigue, mood swings, and irritable behavior. Onset may be gradual and may be transient. Type II is characterized by central nervous system (CNS) spinal and cranial abnormalities often masked by pain distractions. In addition, some patients have symptoms such as: unusual fatigue, headache, and abdominal encircling. The locations of the above symptoms are illustrated in FIG. 1.

To avoid injury due to decompression sickness while diving, dive tables have been developed by the British biologist John Scott Haldane. These tables provide information about the speed of descent, ascent to the surface, and the waiting time for decompression stops, which allow bubbles formed to be dissolved. A typical diving table is the Diver table: No-decompression limits and group designation table, incorporated herein by reference. Since the occurrence of decompression sickness is correlated to bubble formation in tissues, some researchers began studies on the detection of bubbles using different methods.

The incidence of decompression sickness is a problem that continues to be studied since it is seen in divers that strictly follow dive tables. Research continues in order to determine the causes of decompression sickness; in this field, the main objective is the detection of bubbles. "All bubble detection techniques in some way fail to sample the entire population of bubbles that could potentially exist, for example, as a result of limits in sensitivity or resolution" (Leighton, 1994). One of the methods used to detect bubbles in this field of research is the Doppler method, mostly because the ease of operation and its relatively reduce cost. As the previous method, most other systems used today fail to detect the size and number of micro-bubbles prior to the occurrence of the decompression symptoms. Other methods have been developed using ultrasound as a detection tool for the presence of bubble.

1. Pulse echo-ultrasound: a technique in which pulses of ultrasound generated by a piezoelectric transducer are sent into the region to be studied (tissues), and echo signals resulting from scattering and reflection are detected and displayed. The depth of a reflective structure is inferred from the delay between pulse transmission and echo reception. Stephen Daniels in 1981 used an integrating pulse-echo technique where the number of pulse echo-ultrasounds in a scan of the tissue are counted and recorded in a preselected time interval as a signal. The stationary bubbles would be seen as an increase to the echo count and the non-stationary ones would contribute to the variability in echo count, therefore, the echo count gives an estimate of gas volume in tissues.
2. Doppler ultrasound: measures the shift in frequency of a continuous ultrasonic wave when the wave source and/or detector are in motion. Doppler is still the most sensitive technique available. In addition, a Doppler unit is far smaller and less expensive than most instruments required by other methods. The Doppler's ease of operation has aided in its popularity as a tool to examine divers after decompression.
3. Harmonic ultrasound: technique based on the principle of exciting a bubble with a low frequency signal and comparing it to the bubble resonance frequency. If acoustic energy from the bubble is scattered, it can be detected. The excited bubble will oscillate in a non-linear manner, emitting a wave with a doubled frequency.
4. Dual frequency ultrasound: uses a low frequency signal ("pump") to excite bubbles with a known radius, which makes them resonate. A second-high frequency signal ("image") is emitted. When it is incident on the resonating bubbles, a non-linear mixing occurs. This non-linear mixing causes results in a signal with the frequency of the "image" plus or minus the "pump" frequency.

Techniques such as pulse echo ultrasound, harmonic ultrasound and dual frequency ultrasound are under study since Doppler bubble detection is useful for deciding whether a diver needs to receive hyperbaric treatment.

SUMMARY OF THE INVENTION

The present invention provides a feasible method for bubble detection in real time to prevent DCS. The technique was tested on a simulated simplified artificial thigh that acts as an acoustic chamber where the situation of decompression was created by introducing bubbles of known size. Electrical signals emitted by a piezoelectric (PZT) ring placed around the artificial leg indicated the presence of bubbles.

Signal analysis was conducted to determine a relationship between the electrical signals and the presence of stationary or non-stationary bubbles and once the relationship was established, a pattern recognition algorithm was developed for creating a data base in order to determine the size and amount of micro-bubbles present in the blood system that can potentially cause decompression sickness.

The present invention implements a pattern recognition scheme to indicate the presence of micro-bubbles in a diver's bloodstream and tissues. In order to achieve this, the invention provides the system and steps to: (i) analyze the signals that are generated due to bubbles passing through the PZT ring, (ii) determine the size of the bubbles with image processing techniques of the images obtained from a high-speed camera, and (iii) identify the relationship between the size of the bubbles and the PZT ring signals.

BRIEF DESCRIPTION OF THE DRAWINGS

Further features and advantages of the invention will become apparent from the following detailed description taken in conjunction with the accompanying figures showing illustrative embodiments of the invention, in which.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

In order to fully appreciate the novel contribution of the present invention a detailed background description will be provided.

Acoustic Chambers

An acoustic chamber is a simple structure that consists of a glass cylinder with a piezoelectric (PZT) device glued around it. They are made to generate large and controlled pressure oscillations. The excitation of the glass cylinder is caused by the motion of the PZT that deforms when a sinusoidal voltage is applied to it. The crystal contracts and expands at the same frequency at which the electrical current changes polarity. The piezoelectric deformation is transferred to the walls; this is the force that creates the standing acoustic pressure field in the liquid.

Figure 1:
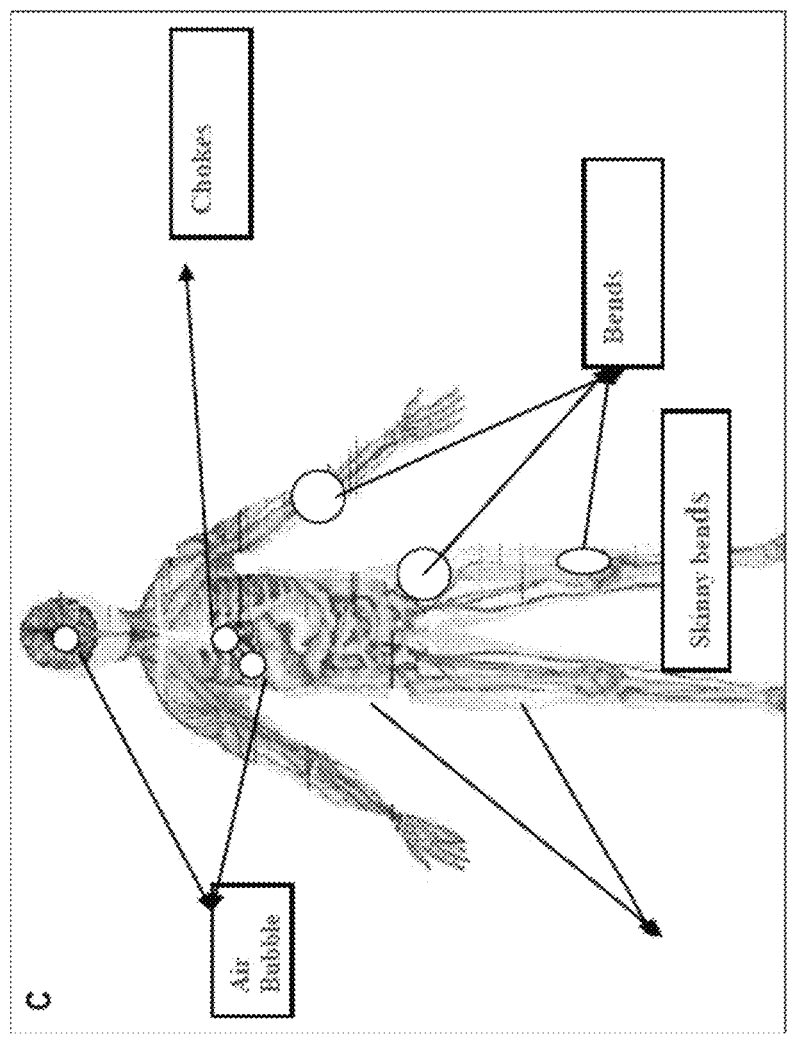
FIG. 1 shows the location of Decompression sickness type 2 on a body.
Figure 2:
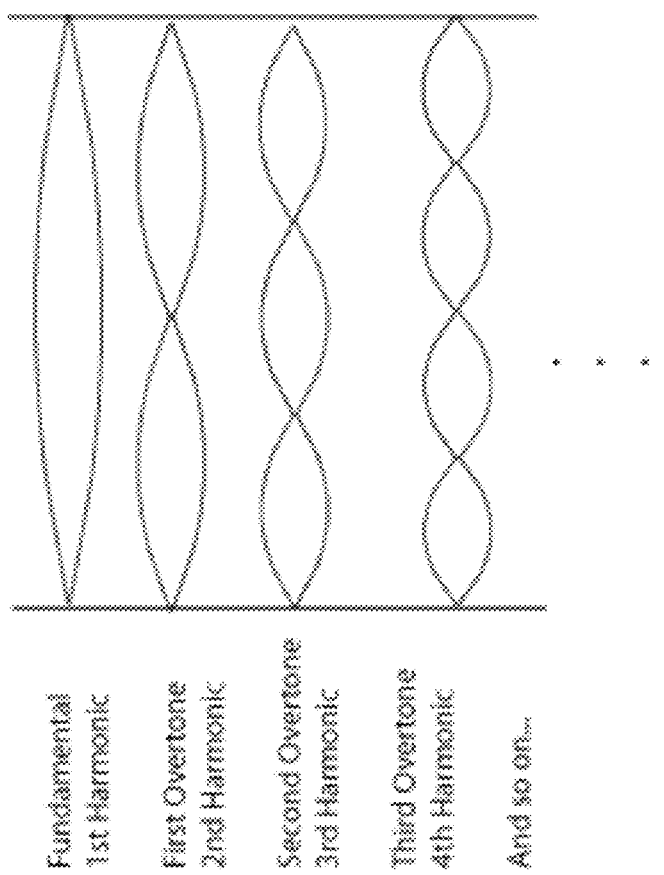
FIG. 2 shows the different standing waves harmonics.

For all structures, there are an infinite number of natural vibration modes. FIG. 2 shows the different standing waves harmonics. However, the greatest acoustic pressure obtained in the fluid occurs when an oscillating voltage with a frequency that matches the first resonance mode is applied. When the system works at the resonance condition, the sensitivity in the elastic properties of the medium become high. If a bubble is introduced in the acoustic chamber, it causes a change in the elastic properties of the fluid, also causing the electrical properties of PZT to change.

Piezoelectric Ring

The piezoelectric ring is a lead-zirconate-titanate ceramic, known by the acronym (PZT). This material has the property of generating an electric current when it is subjected to a mechanical stress, and vice versa, when an electric field is applied to the material, it generates a mechanical deformation. The analysis of the PZT and the interactions with an acoustic chamber is a multi-dimensional model of wave propagation in fluids. A simplified piezoelectric model can be explained as a constitutive equation, expressed as:

$$D = d_1 T + \varepsilon^T E \quad (1)$$

$$S = s^E T + d_2 E \quad (2)$$

Where D is the electric displacement, $d_1$ and $d_2$ are the piezoelectric charge coefficients, respectively for the direct piezoelectric effect and the inverse piezoelectric effect. T is the mechanical stress, $\varepsilon^T$ permittivity constant at constant stress, E is the electric field, E mechanical strain, and $s^E$ is the mechanical compliance. Equations (1) and (2) assume a linear coupling between electric field and strain and that there is no variation in temperature. Equation (1) shows that part of an electrical field applied to material is converted into mechanical stress. Similarly, equation (2) shows that part of a mechanical strain applied to material is converted into an electrical field.

When a piezoelectric material is subjected to acoustic vibrations, it generates an electric field with the same frequency as the vibration. For some frequencies, the transfer of electrical-mechanical energy is maximum, but in other frequencies it is minimum. This behavior, allows an analogy between the piezoelectric and the RLC circuit to be made. The most common electrical circuit used to characterize a piezoelectric device is the Van Dyke Model as illustrated in FIG. 3.

Figure 3:
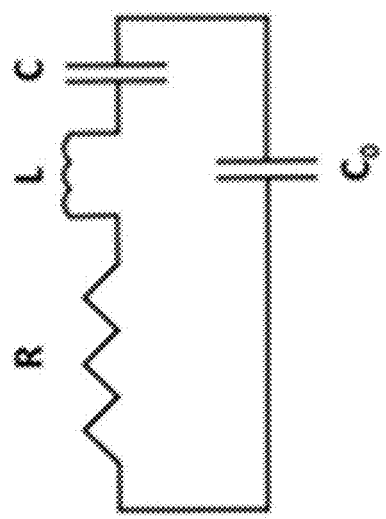
FIG. 3 shows the Van Dyke Model simplified equivalent RLC Circuit of a piezoelectric device.

The following equation shows the equivalent electrical admittance ($Y_{eq}$ of the circuit shown in FIG. 3:

$$Y_{eq} = jwC_0 + \frac{1}{R + j\left(wL - \frac{1}{wc}\right)} \quad (3)$$

In the above equation R, L and C represent the resistance, inductance and capacitance of the system respectively and $C_0$ is the real value of the measured capacitance of the PZT and it is often called blocked capacitance. Finally, applying conjugate, and expanding equation (3), equation (4) can be obtained. The real part (left hand side of equation (4)) is called conductance and the frequency that maximizes this quantity corresponds to the mechanical resonance frequency of the system. In this invention the electrical conductance is measured to determine the mechanical resonance of the system.

$$Y_{eq} = \frac{R}{R^2 + \left(\frac{w^2 LC - 1}{wC}\right)^2} + jwC_0 + \frac{j\left(\frac{w^2 LC - 1}{wC}\right)}{R^2 + \left(\frac{w^2 LC - 1}{wC}\right)^2} \quad (4)$$

Bubble Detection Methods

Some methods for the detection of bubbles such as: basics of ultrasound, pulse echo ultrasound, Doppler ultrasound, harmonic ultrasound, and dual frequency ultrasound will be discussed. The ultrasound term indicates sound waves of frequencies above 20 KHz. Frequencies between 1-30 MHz are used as diagnostic tools since they allow to capture images of internal body structures with non-invasively manner.

Ultrasound

Ultrasound uses the reflection of sound waves off the boundaries between tissues of varying acoustic properties. The acoustic properties of a medium are quantified in terms of its acoustic impedance, which is a measure of the degree to which the medium impedes the motion that constitutes the sound wave. The acoustic impedance "z" is rationed as:

$$z = \rho c \quad (5)$$

Where "$\rho$" is the density of the medium and "c" is the sound velocity. The sound reflection coefficient $\alpha$ at the boundary between two tissue types ($z_1$ and $z_2$) is calculated with equation (6):

$$\alpha = \left(\frac{z_2 - z_1}{z_2 + z_1}\right)^2 \qquad (6)$$

As the acoustic impedance of a gas bubble is much lower than the impedance of any tissue in the body this method can be used as a bubble detector.

Pulse-Echo Ultrasound

Figure 4:
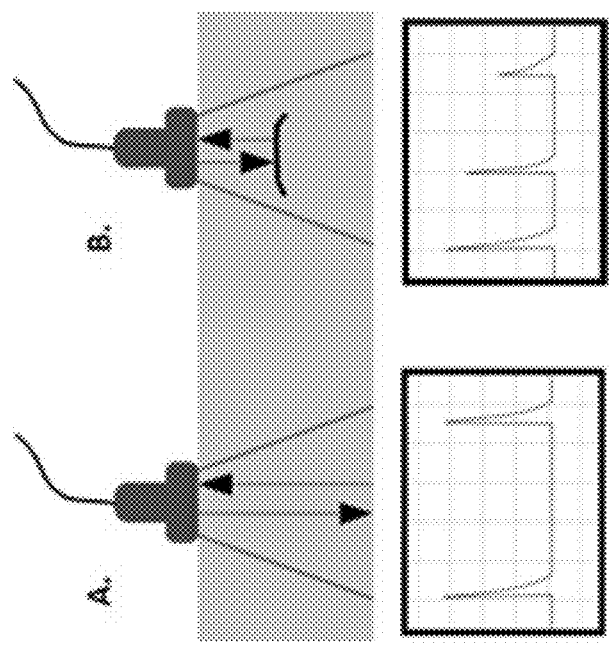
FIG. 4 shows an echo ultrasound with and without bubbles.

This method consists in a pulsed ultrasonic transmitter that sends a signal to scan a tissue region, and a detector that records echoes reflected from scanned tissue in a pre-selected time interval. The method has been used for stationary and non-stationary bubbles. FIG. 4 shows echoes count without bubble (A) and for a stationary bubble, it generates an increase on the echoes counts (B). The biggest problem with this method is the sensitivity to motion and when it is applied on a person in motion (as a diver) alteration in the echo are observed by increasing or decreasing the count and therefore it confuses the bubble detection method.

Doppler Ultrasound

The Doppler effect is described as a change in the frequency of the wave due to relative motion between the source generating a wave and the observer receiving said wave. The Doppler ultrasound has the wave source and the observer or receiver fixed, but there is a reflector that is in motion. The reflector can act as transmitter and receiver. Therefore, the relationship between the frequency experienced by a source and a receptor when both are moving is shown in the equation (7):

$$f = f_o\left(\frac{v_s + v_r}{v_s - v_r}\right) \qquad (7)$$

Where, "$f_o$" is the ultrasound frequency, "$v_r$" is the speed of the reflector, "$v_s$" is the speed of sound and "f" is the detected frequency. When the Doppler effect is applied to the detection of microbubbles, the reflected ultrasound wave produces shifted frequencies. If "$v_s$" is larger than "$v_r$" and the angle between the transducer and the moving object is considered, Doppler shift "$f_d$" can be computed as:

$$f_d = \frac{-2f_o v_r \cos(\theta)\cos\left(\frac{\gamma}{2}\right)}{v_s} \qquad (8)$$

With the angle "$\theta$" being the bisector of the transmitter and receiver beams and the direction of movement. The angle "$\gamma$" is the angle between transmitter and receiver beams. The Doppler shift is not observed in bubbles within tissues because they are stationary structures. On the other hand, the gas bubbles in the blood flow present strong reflections that can be distinguished.

Harmonic Ultrasound

This method uses an acoustic field with a wavelength greater than the radius of the bubble. By inducing a bubble to said acoustic field, it will respond to changes in pressure and it will oscillate causing scattering in the acoustic energy and the bubble can be detected.

Figure 5:
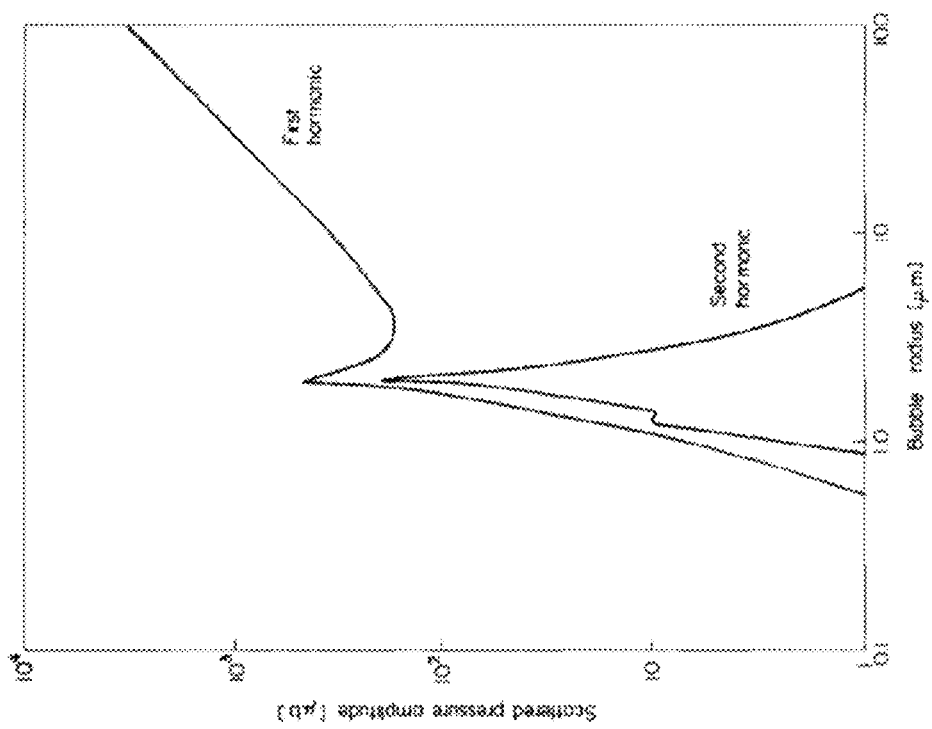
FIG. 5 shows a plot indicating the relationship between pressure amplitude and bubble radius.

The scattered pressure is measured as a function of the bubble radius for the first and second harmonic. At low wave amplitude, the bubbles oscillate in sine-wave fashion, generating the same incident fundamental range of frequencies. At higher acoustic pressures at the resonant frequency, the bubbles' velocity pattern between compression and rarefaction is no longer sinusoidal and the waveform of the returning sound is distorted, containing harmonic frequencies as well as the incident frequency. The results show that both harmonics have a linear response for bubble radius smaller than approximately 4 um where both present a peak in pressure. However, as shown in FIG. 5, the first harmonic continues showing a linear increase in pressure as the bubble radius increases, while the second harmonic doesn't. Moreover, the first harmonic can be measured for bigger bubble radius. This means that the largest bubbles produce the greatest first harmonic response. Otherwise, the second harmonic does not. Excluding the second harmonic, the bubble can be detected with the first harmonic.

Dual Frequency Ultrasound

This method applies two waves with different frequencies. The first wave is called "pump ($f_p$)", and the second wave is called "image ($f_i$)". The frequency range of the pump operation is between low KHz to low MHz. The pump frequency is adjusted to different bubble sizes, i.e, the pump frequency is adjusted to the resonance of the bubble's target size. If a bubble with a resonance frequency equal to the pump frequency is present, then a wave with a frequency given by equation (9) is detected.

$$f_{DFU} = f_i \pm f_p \qquad (9)$$

Figure 6:
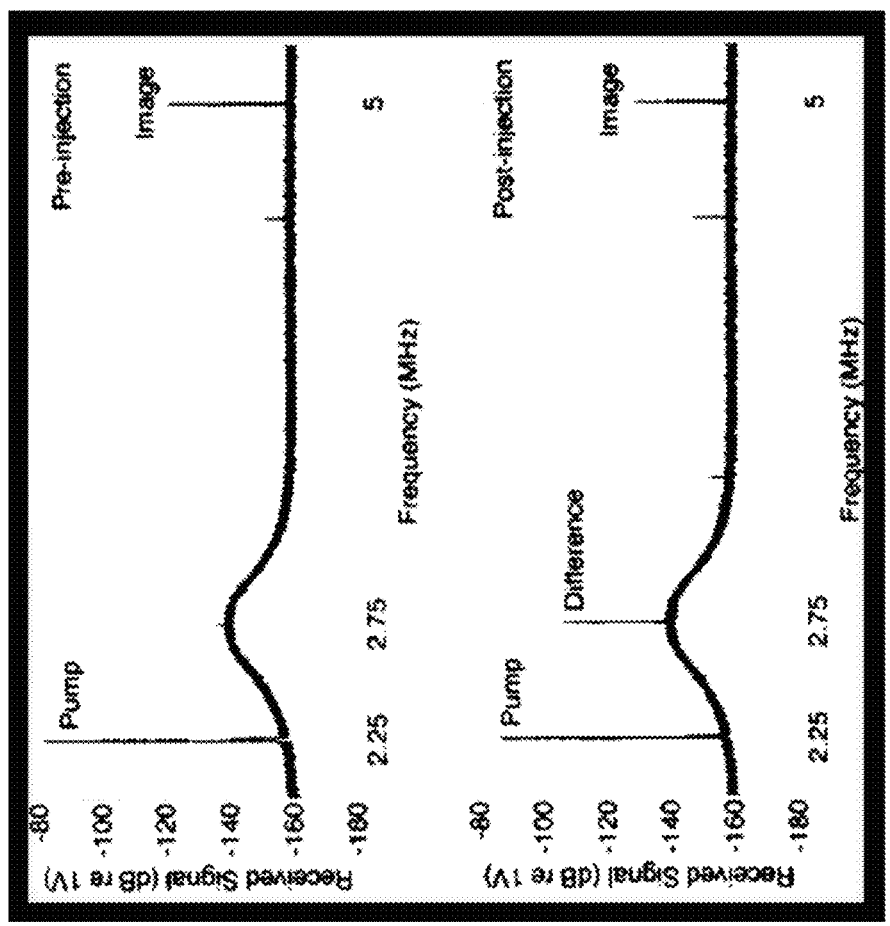
FIG. 6 shows dual frequency data of a target in the hip of an anesthetized swine before and after injection of microbubbles.

The applicability of this method was proven to be feasible in experimental studies. $f_i$=5 MHz and $f_p$=2.25 MHz were used and the results obtained are shown in FIG. 6 where a received signal at 2.75 MHz, which is comparable with $f_i$–$f_p$ is observed indicating the presence of micro-bubbles with a mean diameter of 2-3 µm.

Pattern Recognition

Figure 7:
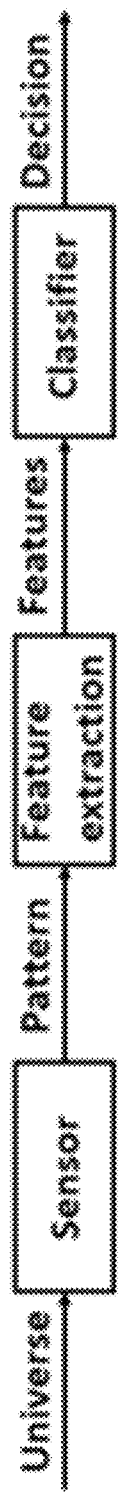
FIG. 7 shows a block diagram of a pattern recognition scheme.

Pattern recognition is the act of taking in raw data and taking an action based on the "category" of the pattern. A simplified process flow diagram of pattern recognition as previously proposed is illustrated in FIG. 7.

Sensor

A sensor is a device capable of capturing information transforming physical or chemical magnitudes in electrical magnitudes. In the present invention, the sensors comprise a piezoelectric ring, the pill microphones, and the high-speed cameras.

Features Extraction

The feature extraction is the process that determines the system variables that will be used as classifiers. There are several techniques that are typically used on the row data to extract a useful variable. The most widely used techniques to process data are: the Root Mean Square (RMS), the Discrete Fourier Transform (DFT) and the Cross Correlation. The choice of technique will be based upon the type of change in the signal induced by the presence of the bubbles.

The Root Mean Square

When a signal has only amplitude changes, the common method to analyze this phenomenon is the root mean square (RMS). The RMS method takes a squaring of each point that represents the waveform ($x_N^2$), dividing it with the length of the waveform (N), obtaining the mathematical average. The RMS is defined as:

$$X_{RMS} = \sqrt{\frac{(x_1^2 + x_2^2 + x_3^2 + \ldots + x_N^2)}{N}} = \sqrt{\frac{1}{N}\sum_{i=1}^{N} x_i^2} \qquad (10)$$

Figure 8:
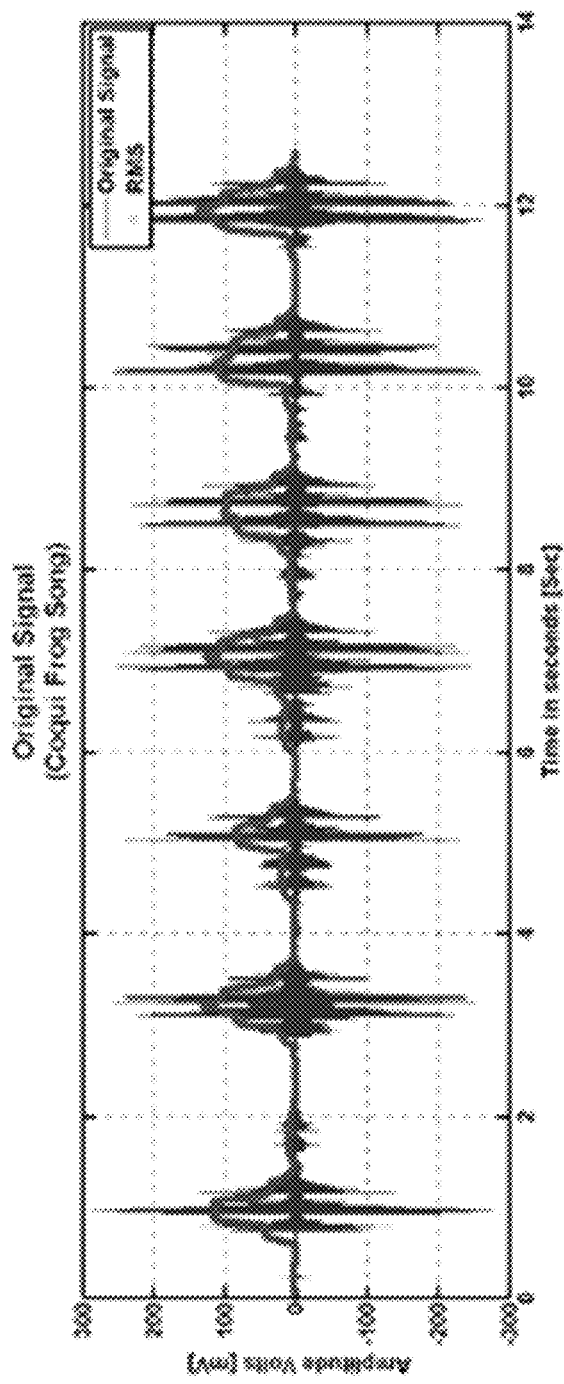
FIG. 8 shows an example of the RMS method applied on the coqui frog song (CFS) Signal.

The RMS method is usually applied in power system measurements, because it is fast and it requires less memory than other methods. The RMS method has been used as a speech/music discriminator. Two signals were acquired: the first one was a speech signal (the total duration was 11328 sec) and the second one was a music signal (the total duration was 3131 sec). For both signals the RMS was computed and the next step was to calculate the histogram from both RMS values. The distributions obtained from the histograms (histogram of the speech signal and the histogram of the music signal) are almost non-overlapping, therefore, indicating this method is adequate as a discriminator. FIG. 8 shows an example of the RMS method applied on the "coqui frog" song (CFS) signal.

The RMS value increases according to the amplitude of the original signal. One problem with this method is shown with the above example; even though the signal comes from the same frog, there are fluctuations. The RMS value requires similar conditions when used for signal detection, otherwise, false positives will be generated.

Figure 9B:
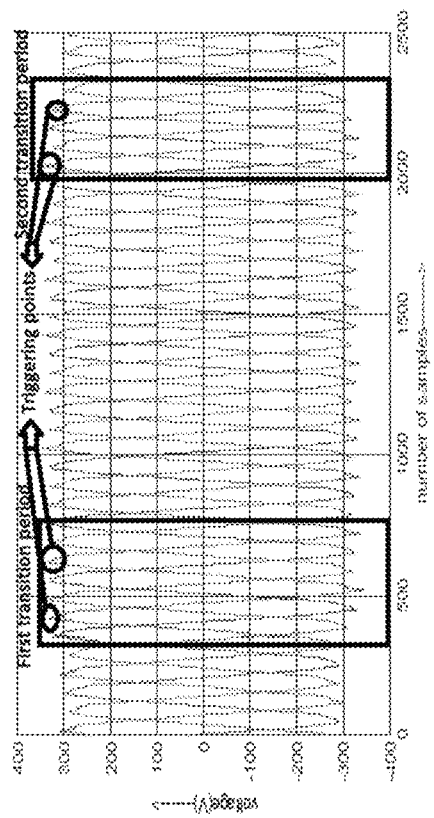
FIG. 9B shows a 3-phase voltage swell waveform with 2 transition periods and four triggering points.
Figure 9A:
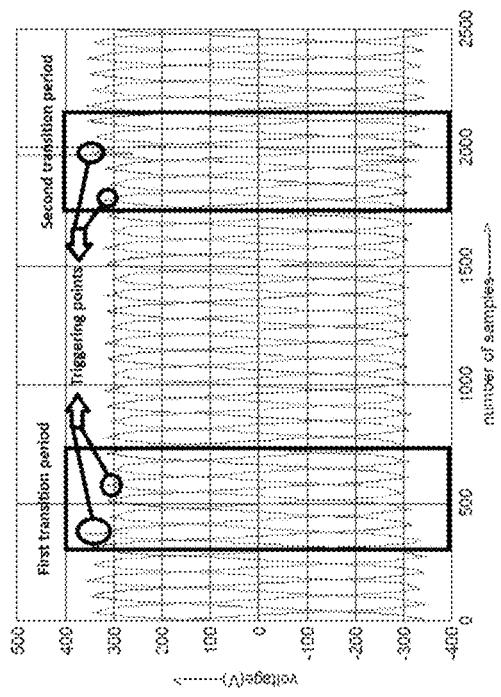
FIG. 9A shows a 3-phase voltage sag waveform with 2 transition periods and four triggering points.

The RMS method has also been used as detection of power quality disturbances. The RMS value was computed for 2 cases: sag waveform and swell waveform. FIG. 9A shows a 3-phase voltage sag waveform with 2 transition periods and four triggering points. Triggering points refer to sudden changes on the voltage amplitude. When the RMS was computed, it detected 5 triggering points of the 4. A similar problem was found when the swell waveform was analyzed FIG. 9B. This method shows high sensitivity to changes in signal amplitude causing false positives for the triggering point's detection, but on the other hand, it is useful for the changes in amplitude detection.

Discrete Fourier Transform

The Discrete Fourier Transform (DFT) is a tool that, besides transforming the samples of signals from the time domain into the frequency domain, can be used in image compression, interpolation, and in the others tasks. DFT is a modification of Fourier transform. The DFT is used, when the data are available as sampled time function form, and it were represented by a time series of amplitudes with fixed time intervals of limited duration. The DFT is calculated with the formula (11):

$$X_k = \sum_{i=0}^{N-1} x_i e^{\frac{-j2\pi ik}{N}} \quad (11)$$

Where N is the total amount of the data points, $x_i$ refers to each total point with i=0, . . . , N−1, $X_k$ is the amplitude of each frequency k, with k=1 . . . N−1. The frequency resolution $\Delta f$ is determined by:

$$\Delta f = \frac{f_s}{N} \quad (12)$$

with $f_s$ as sample rate in samples per seconds.

Figure 10A:
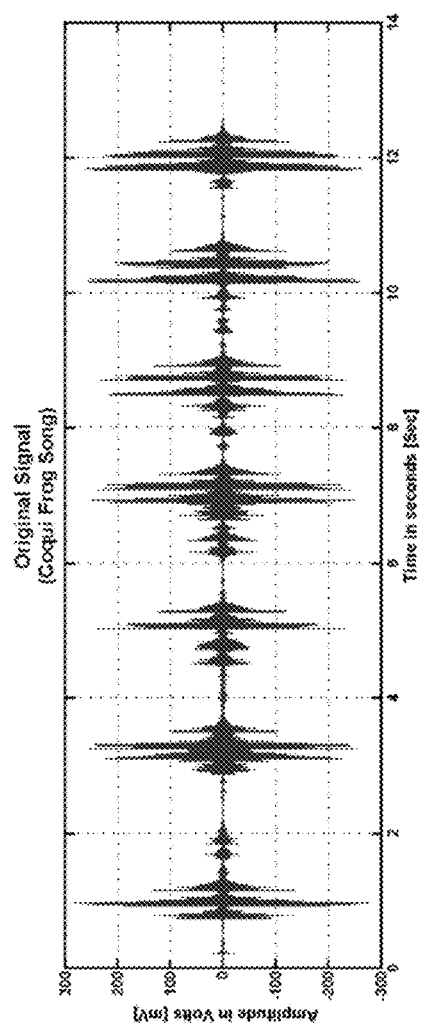
FIG. 10A shows an original signal of the coqui frog song (CFS).
Figure 10B:
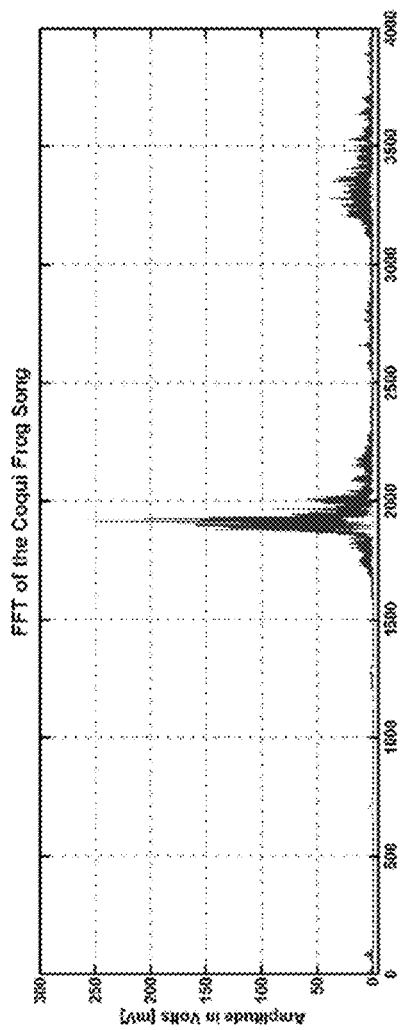
FIG. 10B shows the frequency components of the coqui frog song (CFS).

The Fast Fourier Transform (FFT) is a faster version of the DFT. Therefore, FFT algorithms such as Cooley-Tukey reduce the computational work and the rate of converge. The DFT is not suitable for non-stationary signals, in which case the STFT should be applied. The STFT, splits the signal into intervals that are considered as stationary, and then the DFT in each partitions is used. An example of the analysis of signals using FFT is shown in FIG. 10A and FIG. 10B. In this example the "Coqui frog" song was analyzed as shown in FIG. 10A. At first glance the different frequency components are not noticeable. FIG. 10B shows the frequency components of the CFS, the components between 1800-2100 Hz characterize the "Co" and the components between 3200-3500 Hz represents the "qui". The use of the DFT in this case is capable of extracting the main features of the CFS.

Cross-Correlation

The auto-correlation and cross correlation are used to analyze the similarity between signals. If the comparison of the signal is done with itself, it is called "auto-correlation", and it is defined by equation (13) and equation (14) for the case of continuous and discrete signals, respectively.

$$R_{xx(\tau)} = \int_{-\infty}^{\infty} x_{(t)} x_{(t-\tau)} dt \quad (13)$$

$$R_{xx(m)} = \sum_{-\infty}^{\infty} x_{(n)} x_{(n-m)} \quad (14)$$

The "cross correlation" between two signals is defined by equation (15) and equation (16) for continuous signals and discrete signal, respectively $$R_{xy(\tau)} = \int_{-\infty}^{\infty} x_{(t)} y_{(t-\tau)} dt \quad (15)$$

$$R_{xy(m)} = \sum_{-\infty}^{\infty} x_{(n)} Y_{(n-m)} \quad (16)$$

In equations (13) and (15) "t" is the time and "T" is the time shift. T=0, ±$a_1$, +$a_2$, . . . , $a_{T-1}$, where "T" is the length of the analyzed signal and an refers to interval sections of the signal (smaller than the period of the signal). In the equations (14) and (16) "$x_n$" refers to each data in the signal and "m" is the "lag". "m" is defined as 0, ±1, ±2, . . . , N−1, where N is the length of the sampled signal. In the analysis of the structures, autocorrelation is frequently used to determine for example the bridges condition. An example is shown in FIG. 11A and FIG. 11B.

Figures 11A, 11B:
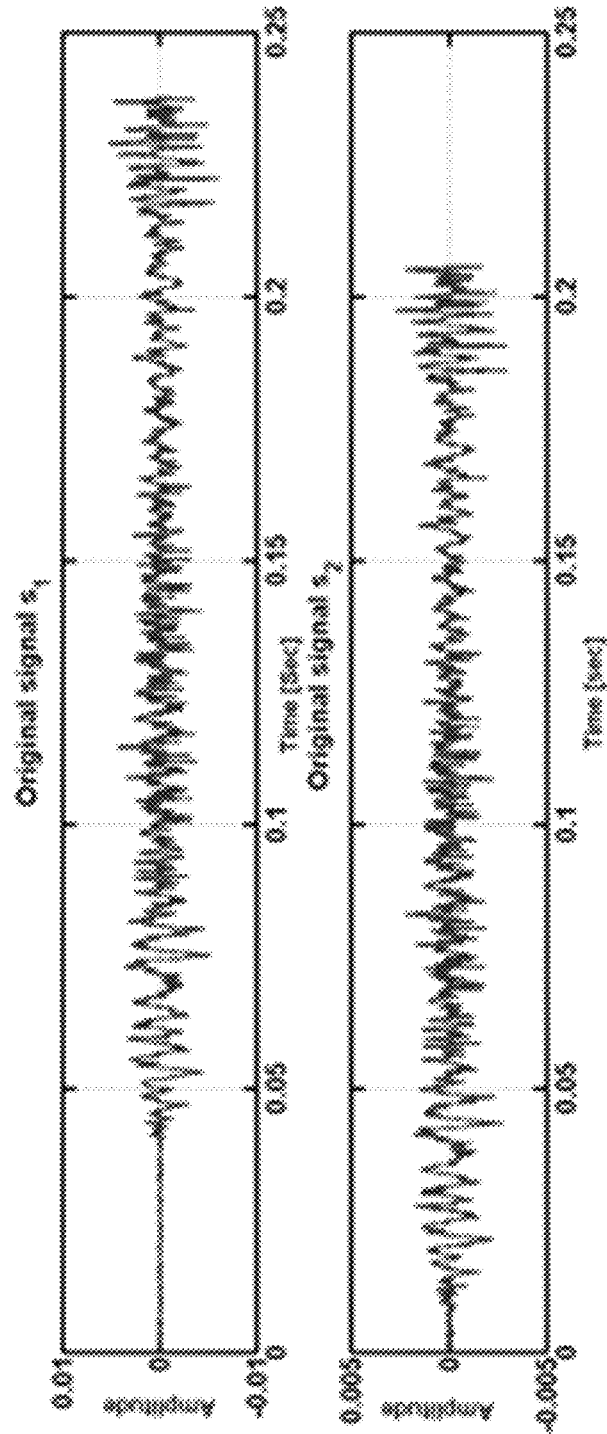
FIG. 11A shows the vibrations measured by sensor 1 when a car crosses a bridge.
FIG. 11B shows the vibrations measured by sensor 2 arriving at an earlier time than the signal from Sensor 1.
Figure 12:
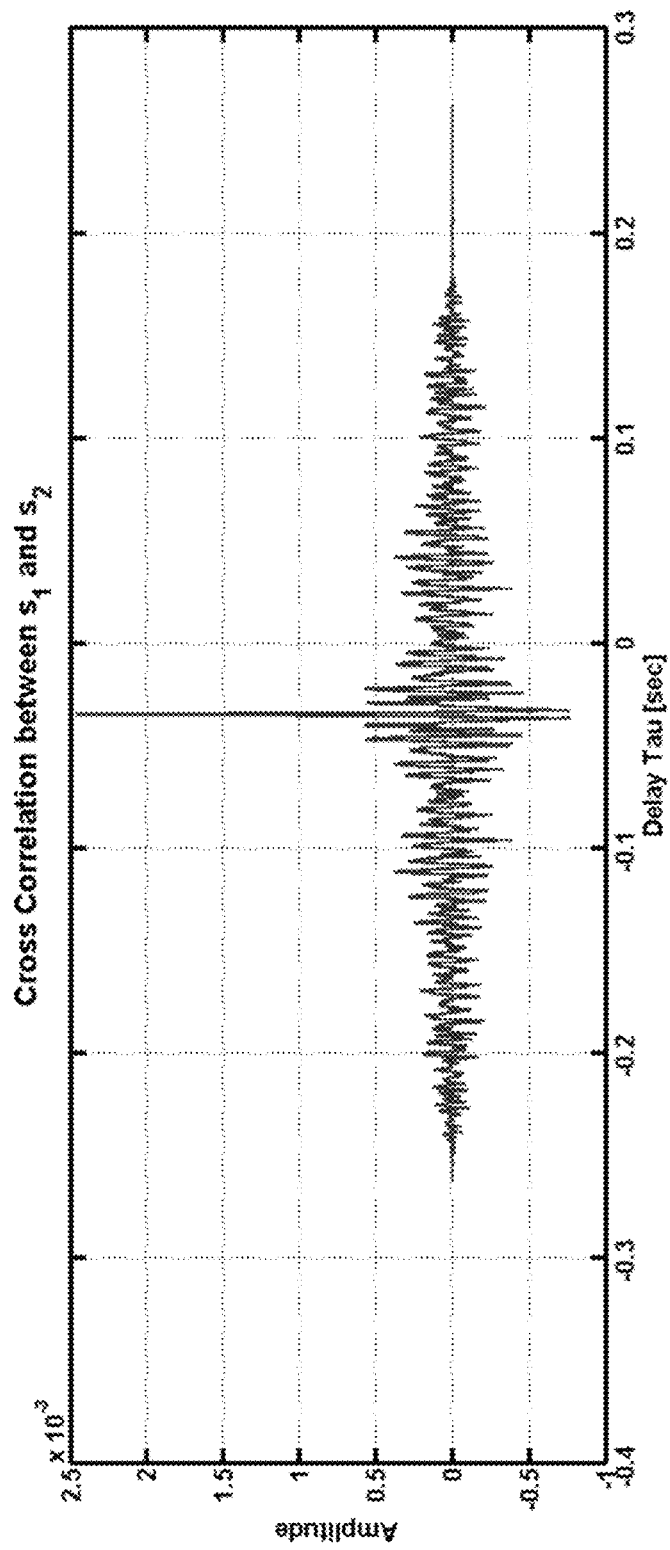
FIG. 12 shows the ross correlation between sensor 1 and sensor 2.

FIG. 11A shows the vibrations measured by sensor 1 when a car crosses a bridge. FIG. 11B shows a similar signal measured by sensor 2 but it arrives at an earlier time than the signal from Sensor 1. When the cross correlation was applied, the delay between the sensors 1 and 2 is clearly identified as shown on FIG. 12. The absolute maximum of the cross correlation amplitude occurs for T=0.035 sec, which is coincident with the delay between the sensors. Therefore, the cross correlation indicates the similarity between signals (showing the maximum amplitude and comparing it with the original signal), and, it shows the delay between signals too.

Accordingly, the above-explained methods should be used depending on the approach to extract information:
- The RMS is useful for extracting features related to changes in amplitude.
- The DFT is useful to extracting a features related to frequency.
- The Cross correlation is useful for extracting features related to changes in amplitude, in frequency and delays between signals.

Classifier

The main function of the classifier is to assign different characteristics to groups with largest similarity between them. The classifiers can be of two types: supervised or unsupervised.

The supervised classification is the essential tool used for extracting quantitative information. Using this method, the analyst has sufficient known data available to generate representative parameters for each class of interest. This step is called training. Once trained, the classifier is used to attach labels to all the data according to the trained parameters. Among the most widely used supervised classifiers are the Neural Nes (NN) and Support Vectors Machine (SVM). On the other hand, the unsupervised classification does not require a human to have the foreknowledge of the classes, and uses clustering algorithms to classify a set data. Among the most widely used unsupervised classifiers is the k-mean. The choice of the best classifier depends on the applications. For example, if clustering of data is needed, the unsupervised classifiers are the most appropriate, while if the detection for recognition is needed the supervised methods should be chosen.

Support Vector Machine

Support Vector Machines (SVM) is defined by kernel functions that analyze data and recognize patterns. The simplicity comes from the fact that Support Vector Machines apply a simple linear method to the data but in a high-dimensional feature space on-linearly related to the input space. Given a set of training, SVM takes a set of input data and predicts, for each given input, which of two possible classes forms the output, making it a non-probabilistic binary linear classifier.

Figure 13:
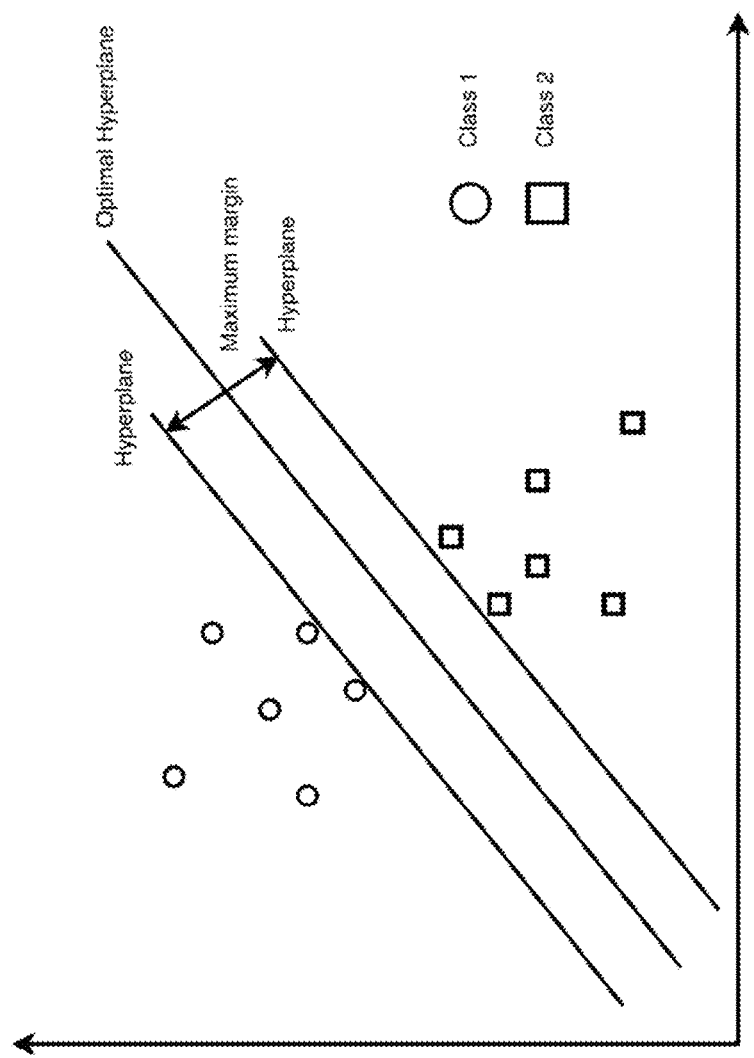
FIG. 13 shows an example of a linearly separable set.

FIG. 13 shows an example of a linearly separable set. SVM designs a hyperplane to separate classes:

$$s_{(x)} = \vec{a}^T \vec{x} + b \quad (17)$$

Where $a^T$ and b are real coefficients and z is the input vector with the trained data.

The classification can be defined as follows:

$$\text{Class} = \text{sign}(\vec{a}^T \vec{x} + b) \quad (18)$$

Where the sign function determines if the $s_{(x)}$ is greater than zero, equal to zero or less than zero. The SVM algorithm is known for finding the maximum separation between classes. The decision for each point is given by:

$$\text{Class } 1 \rightarrow \vec{a}^T \vec{x} + b = 1 \quad (19)$$

$$\text{Class } 2 \rightarrow \vec{a}^T \vec{x} + b = -1 \quad (20)$$

The distance to origin is:

$$\text{Hyperplane } 1 \rightarrow \frac{|1-b|}{\|w\|} \quad (21)$$

$$\text{Hyperplane } 2 \rightarrow \frac{|-1-b|}{\|w\|} \quad (22)$$

The resulting margin is:

$$\frac{2}{\|w\|} \quad (23)$$

The minimizing "w" causes the maximization of the separability. This is an optimization problem, with the following solution:

$$\vec{w} = \Sigma_{i=0}^N \alpha_i y_i \vec{x}_i \quad (24)$$

$$\Sigma_{i=0}^N \alpha_i y_i = 0 \quad (25)$$

The supervised methods SVM and NN have been used to identify the muscle motion in humans. The information of the surface electromyography (sEMG) was obtained for the six muscles of the upper-limb from 7 subjects. RMS method was used to extract the feature as the sEMG detects changes amplitude. It was introduced in classifiers creating a pattern to muscle motion. The results showed that NN classifier produced the highest recognition accuracy rate. On the other hand, SVM took less time in training process than NN. SVM classifier is the most appropriate for real time applications.

Artificial Neural Networks (NN)

Figure 14:
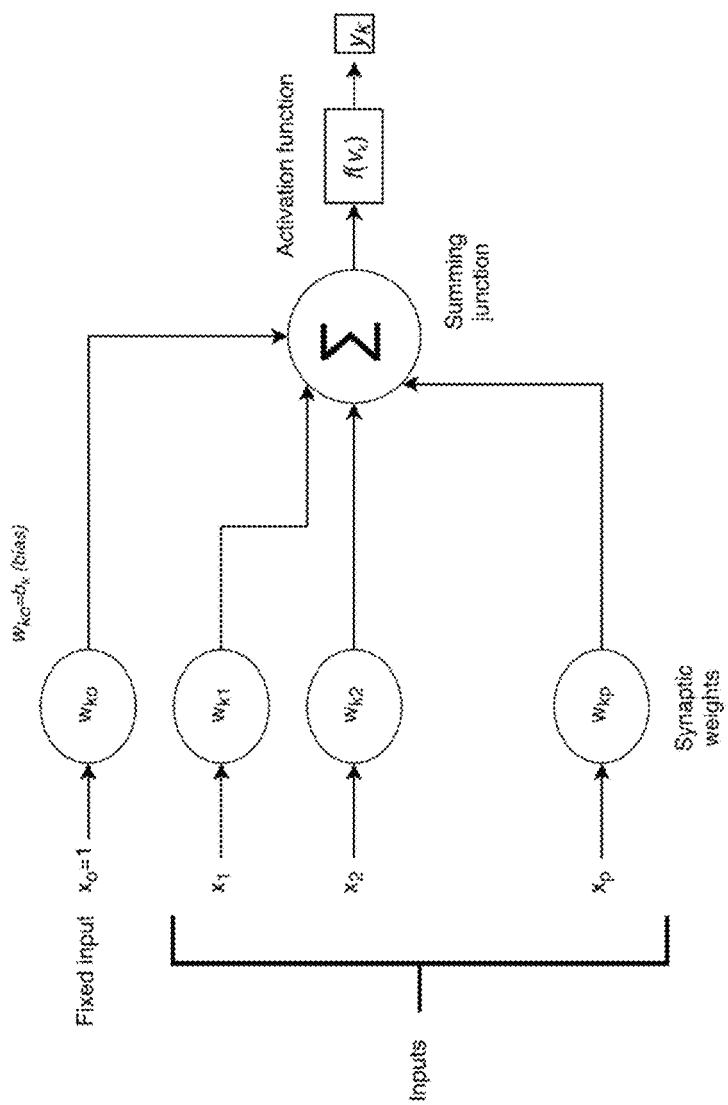
FIG. 14 shows an algorithm explaining the non-lineal neuron model.

A neuron is a processing element with the capacity to receive and transmit information to another neighbor neuron. Artificial neural networks are a computational attempt at modeling the information processing capabilities of nervous systems. As shown in FIG. 14, in the neuron model it is possible to identify three elements:

1. The synaptic weights indicate the strength of a connection between neurons.
2. Summing junction, is an added weight by the respective synapses of the neuron.
3. An activation function is used to limit the amplitude of the output neuron.

The mathematical model of a neuron can be written by:

$$v_k = \Sigma_{i=0}^p w_{ki} x_i \quad (26)$$

With the output:

$$y_k = f(v_k) \quad (27).$$

The activation function determines the output associated to specific inputs. Different types of the activation function exist, some of which are explained below.

Figure 15:
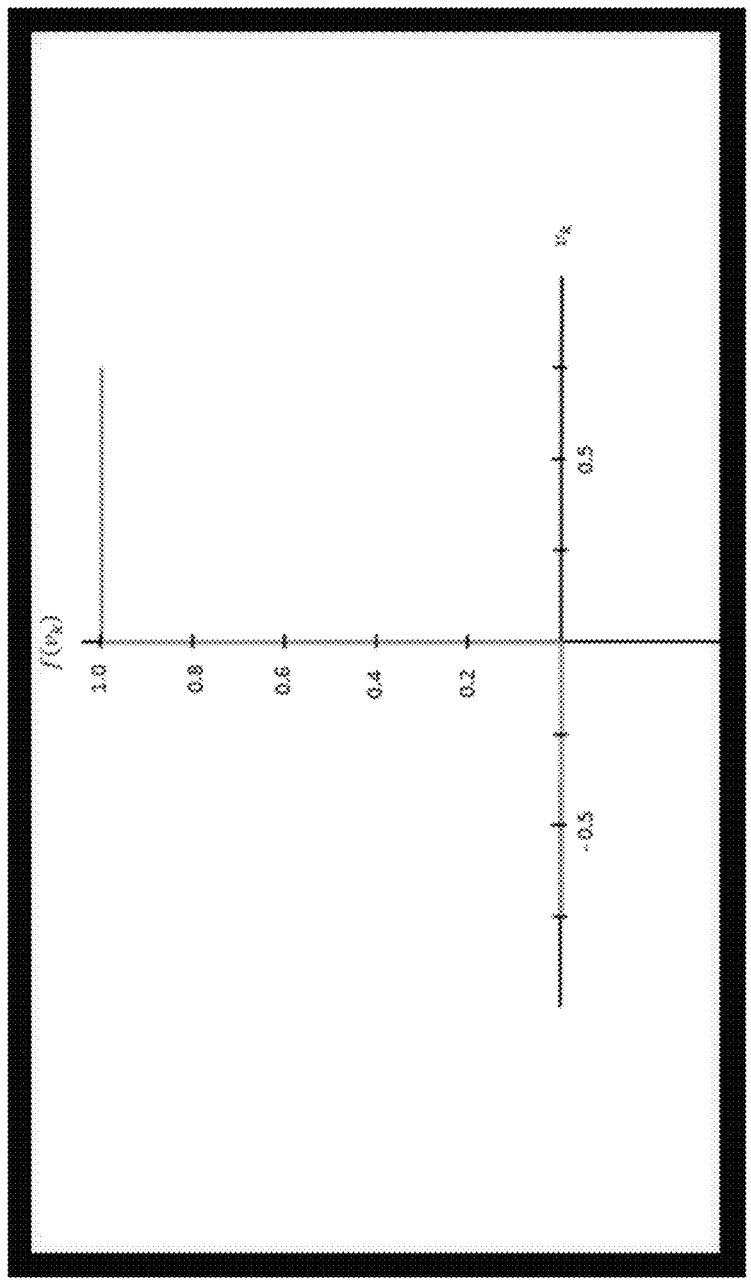
FIG. 15 shows the Threshold activation function.

FIG. 15 shows the Threshold activation function (McCulloch-Pitts model), where:

$$f(v_k) = \begin{cases} 1, & \text{if } v_k = \sum_{i=0}^p w_{ki} x_i \geq 0 \\ 0, & \text{otherwise} \end{cases} \quad (28)$$

Figure 16:
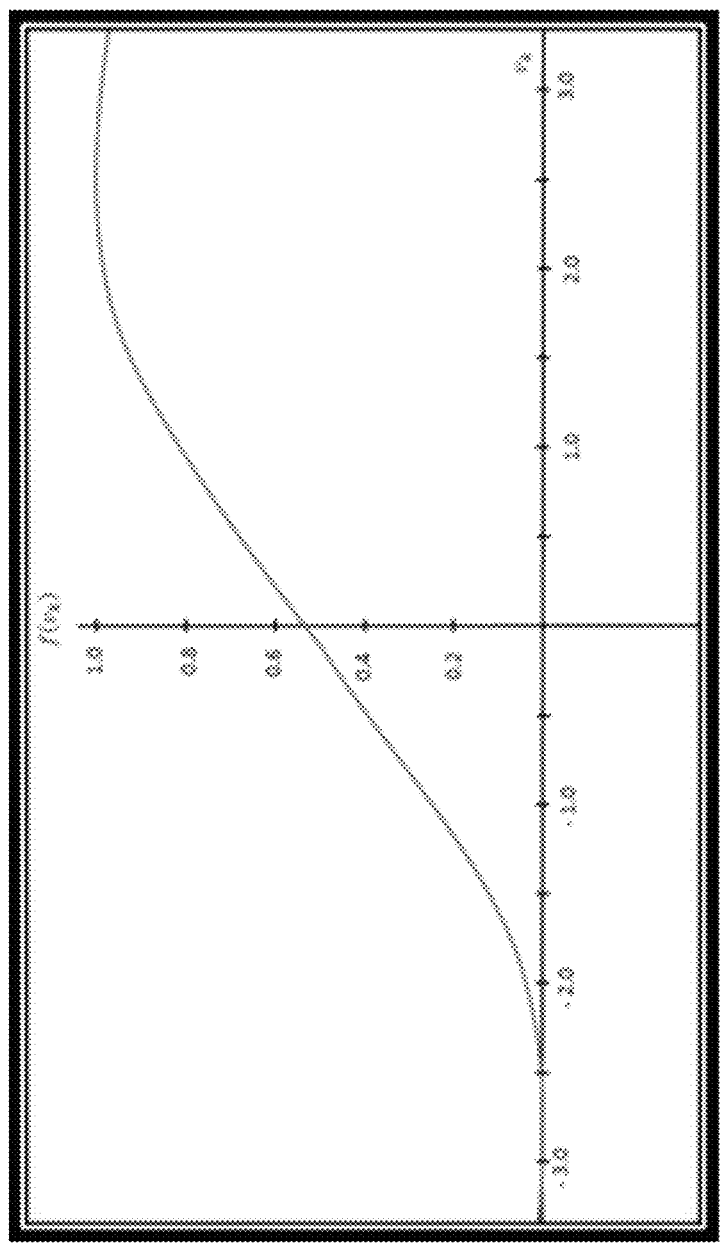
FIG. 16 shows the Sigmoid activation function.

FIG. 16 shows the Sigmoid activation function, where:

$$f(v_k) = \frac{1}{1+e^{-v}} \quad (29)$$

Figure 17:
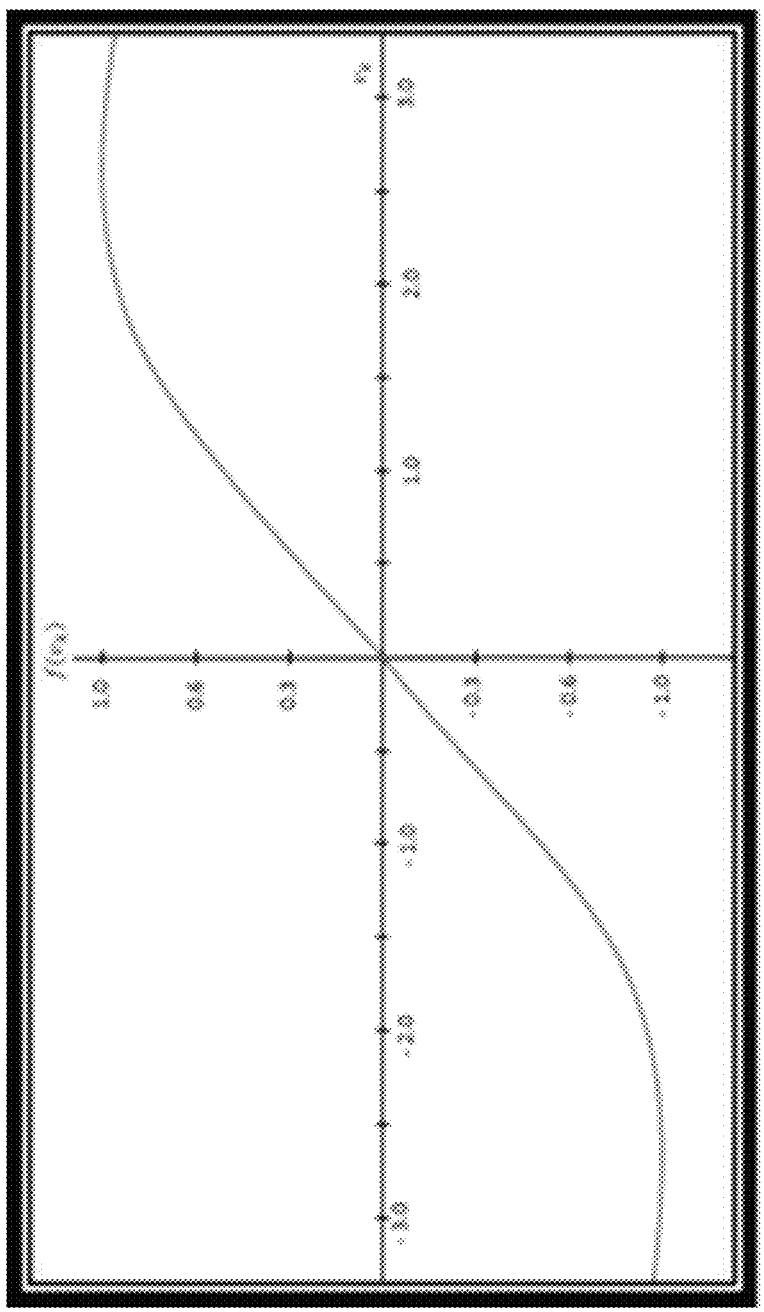
FIG. 17 shows the Hyperbolic tangent function.

FIG. 17 shows the Hyperbolic tangent function, where the definition of the hyperbolic tangent function is showed in the equation (30) which can be re-written as equation (31):

$$f(v_k) = \frac{e^v - e^{-v}}{e^v + e^{-v}} \quad (30)$$

$$f(v_k) = \frac{1-e^{-2v}}{1+e^{-2v}} \quad (31)$$

NN has been used to differentiate impulsive events, such as artillery fire, and non-impulsive events, such as wind or aircraft noise. Cross correlation technique was implemented as feature extraction, and the NN algorithm was trained with different types of noise source as: tank main gun, Mortar impact, Hand grenade, wind noise, helicopter, etc. A total of 2670 recordings were used. The result shows that NN produced a high precision to discriminate between impulsive events and non-impulse events. NN is an appropriate method when accuracy is more important than computational cost.

K-Mean

Figure 18:
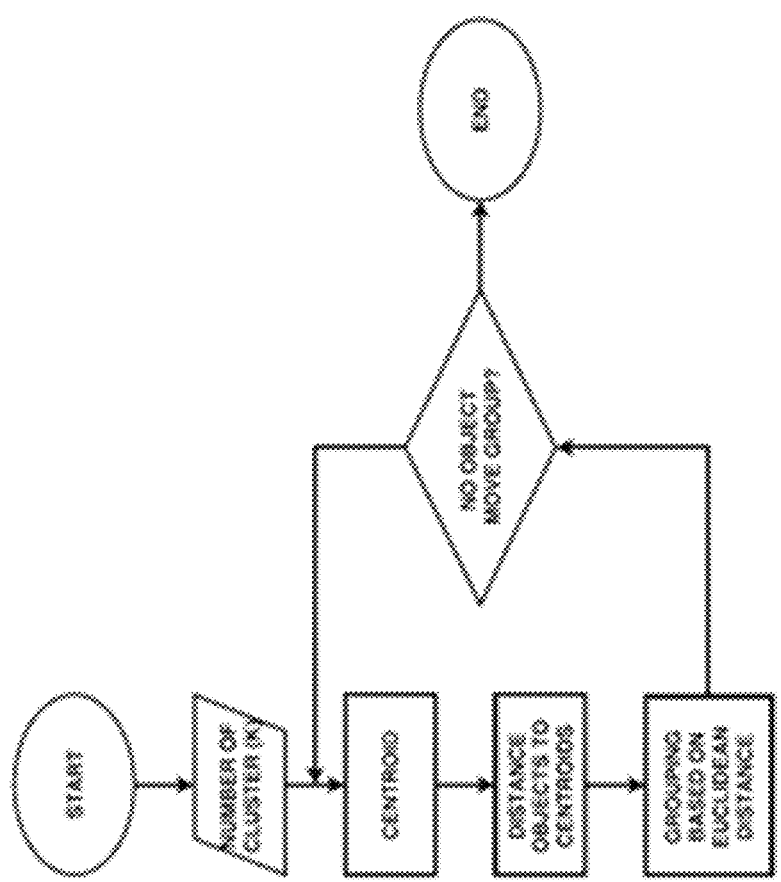
FIG. 18 shows a block diagram of the K-mean algorithm.

K-mean is an algorithm to classify objects based on features into k number of clusters. The grouping is done by minimizing the sum of squares of distances between data and the corresponding cluster centroid. A simple algorithm for this classifier is shown in FIG. 18.
1. The first step is to select the number of clusters "k".
2. Choosing the initial partition (centroids $x_{si}$, $y_{si}$) to classify "k" clusters data.
3. Compare each sample with the centroid of each cluster; the shortest distance indicated that belongs to that group. The Euclidean distance is used normally to determine the distances between pairs of the data. The Euclidean distance between to data points of the sampled signal ($x_i$ and $y_i$) is defined as:

$$d_{(x,y)} = \sqrt{\sum_{i=1}^{N}(x_i-x_{si})^2+(y_i-y_{si})^2} \quad (32)$$

4. When the clustering is done, the new centroid is determined with the average.

$$C_{k(x,y)} = \left(\frac{x_1+x_2+\ldots+x_N}{N}, \frac{y_1+y_2+\ldots+y_N}{N}\right) \quad (33)$$

Where $C_{k(x,y)}$ is the centroid of the k cluster, $x_N$ are the values of the feature x, and $y_N$ are the values of the feature y. N is the length of the data.
5. If the centroids value change, then repeat step 3.
6. If the centroids not change, then done.

If the number of data is less than the number of clusters, then we assign each data as the centroids of the cluster. The unsupervised K-mean method has been used as detection of anomalies in new monitoring data. The features used to clustering were: the total number of packages, total numbers of bytes, and number of different source-destination. These data were obtained of the flow records (2 minutes of recording) which are available in networks due to wide deployment of Cisco Netflow. In this case two clusters were created (k=2), normal traffic and anomalous traffic. The cluster creation process is called traineing. The next step is to take the new data, extract the features and by computing the Euclidean distance to each of the clusters centroid determine if it is a normal or anomalous traffic. The results show that K-mean algorithm can be used as detector for anomalous traffic and it has a low computational cost, therefore it can be implemented in real-time.

The system according to the present invention and its methodology will be explained below.

Methodology

Artificial Thigh

With the main objective of detecting bubble size, an artificial thigh was built with a PZT ring placed around it, generating an acoustic chamber. The experimentally used acoustic glass chamber consists of a Pyrex cylinder with 95±0.4 mm OD and 300±5 mm length (Pyrex 7740, Ace Glass, Vineland, N.J.) and an inner cylinder with 20 mm OD and 300 mm in length made of a material that mimics human bone (3403-09, Sawbones, Vashon, Wash.). The vein and artery were vinyl tubes with (7.94±0.16 mm and 6.35±0.1 mm OD respectively). The PZT ring has the following specifications (BM400, Sensor Technology Ltd., Canada): was radially polarized with 110±0.1 mm OD, 98 mm ID, and 25.07±0.8 mm height. The BM400 material is equivalent to Navy PZT Type IV materials (Sensor Technology, Collingwood, ON, Canada). The PZT belts the glass cylinder and was glued with Stycast 1264 (Emerson & Cumming, Billerica, Mass.) epoxy, cured at room temperature. Three piezoelectric discs (C-5400, Santa Barbara, Calif.), were glued to the glass cylinder to 0 cm, 1 cm and 2 cm from the bottom edge of the PZT ring.

Figure 19:
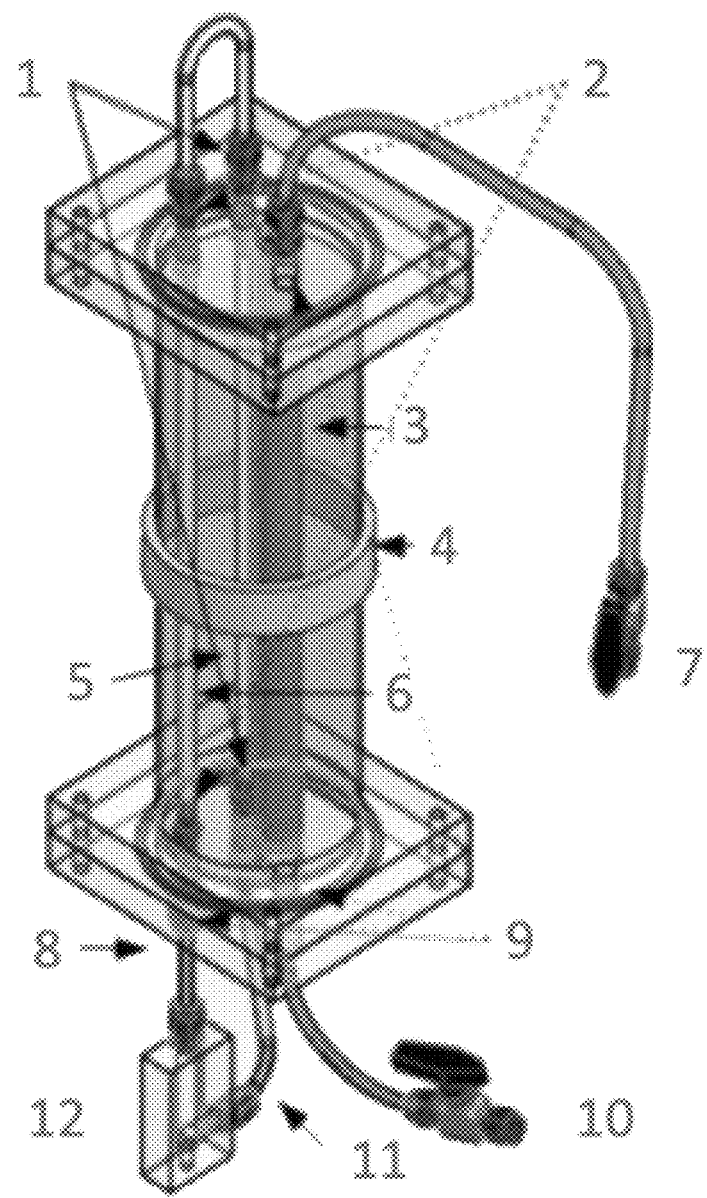
FIG. 19 shows an acoustic chamber design to model a human tight, according to the present invention.

Using the simulated simplified human thigh, the micro bubbles were detected, and characterized. The simulated simplified human thigh shown in FIG. 19 includes: NY 2 HC 1-2 (1), NY 3 HC 1-2 (2), an artificial bone 3, a piezoelectric ring 4, "Artery" vinyl tubing 5, "Vein" vinyl tubing 6, a vacuum valve 7, acoustic chamber flow entrance 8, NY 400 1-2 (9), a filing/drain valve 10, acoustic chamber flow exit 11 and a bubble generator device 12. The acoustic chamber was filled with distilled filtered water. The acoustic chamber shown in FIG. 19 is filled with degassed water while at vacuum pressures of approximately 5-6 Torr. This procedure prevents the formation of random bubble nucleation, allowing for a better characterization of the system. When the process is completed, a gas free acoustic chamber is ready for a frequency response analysis with the objective of determining its resonance frequency.

Bubble Generating System

Figure 20:
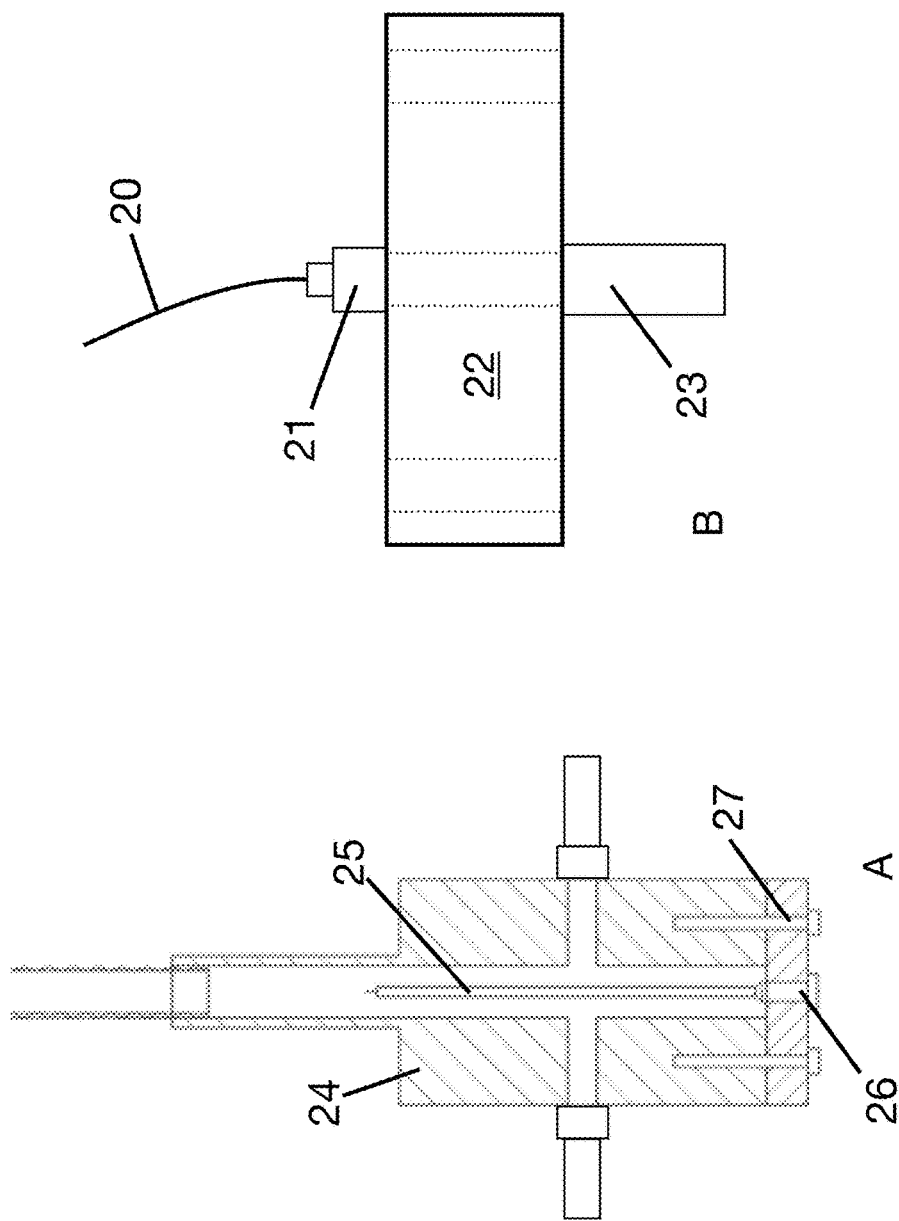
FIG. 20 shows a piece of acrylic used to drive bubbles into the artificial artery.

A bubble generating is used to introduce bubbles in the artificial thigh and it is composed by 33-gauge needle with a point style number 3 (91033, Hamilton Company, Reno, Nev.) connected to a luer connector. FIG. 20B shows the connections of the needle 20 with luer connector 21 and a small piece of acrylic 22. The piece is used such as convertor between luer connector to PTFE tubing 23. The tubing is connected with a Valve (86580, Hamilton Company, Reno, Nev.).

Figure 21:
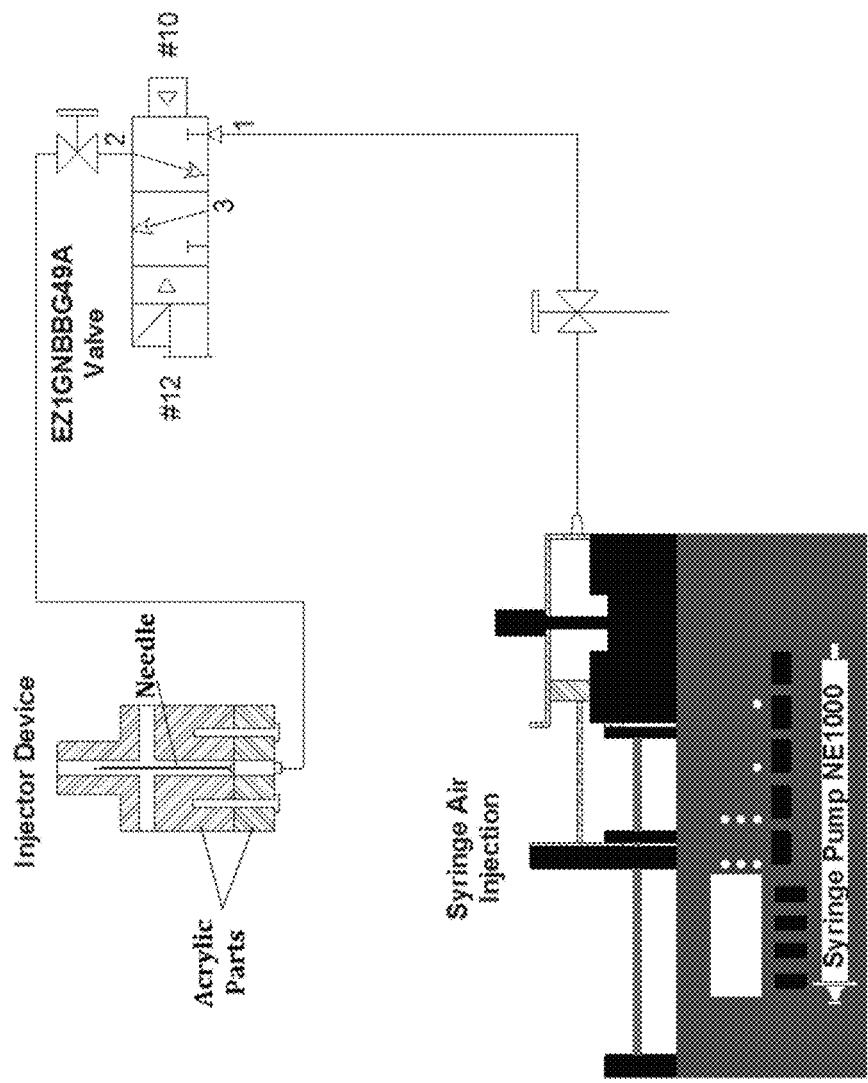
FIG. 21 shows a bubble generator system, according to the present invention.

FIG. 20A shows a piece of acrylic 24 that has a 120 mm length to drive bubbles into the artificial artery. A needle 25, a luer connector 26 and socket bolts 27 are also shown in FIG. 20A. An electro-valve that is a single solenoid 3 way 1 position, normally closed (EZ1GNBBG49A, Richland, Mich.), and syringe pump (NE-1000, Farmingdale, N.Y.), were used such as a control system (see FIG. 21) to the volume of the minimum air induced to create one bubble into the acoustic chamber. The electro valve is controlled by a program developed in Labview.

Figure 22:
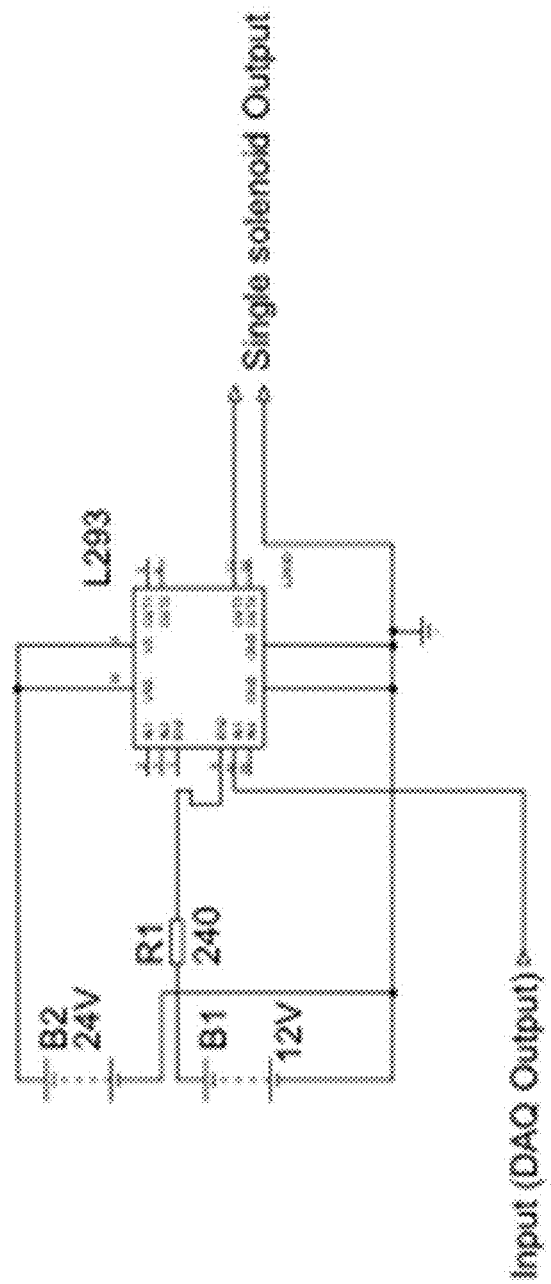
FIG. 22 shows en electrical diagram of a power converter circuit, according to the present invention.

The voltage required to operate the solenoid is 24 VDC. However the 24 VDC cannot come from the NI6356 card port. Because of this, the solenoid must be fitted with a circuit to operate at low voltage signals, power systems. The diagram of FIG. 22 shows an integrated circuit "L293" (used as a power converter) for the implementation.

Figure 23:
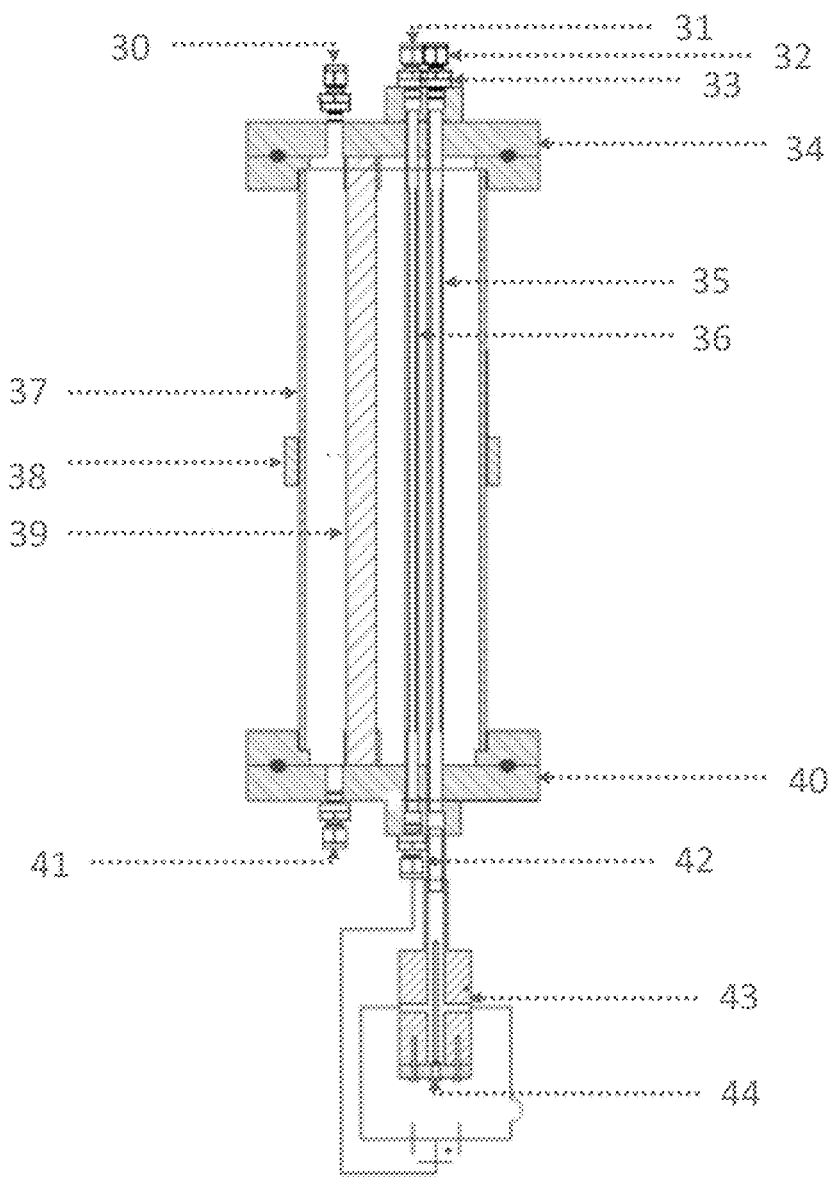
FIG. 23 illustrates a prototype scheme of the artificial thigh, according to the present invention.

Degassing Protocol Initially, 3 liters of filtered deionized (Milli-Di, EMD Millipore, Merck KGaA, Germany) water in Erlenmeyer glass was magnetically stirred with (11-100-100S Isotemp, Fisher Scientific, Waltham, Mass.) to promote off-gassing while a continuous vacuum that was applied by a vacuum pump (8890A, Welch, Niles, Ill.) for 45 minutes. Before filling the system shown in FIG. 23, it is necessary to apply vacuum. Vacuum pressure was measured with a digital pressure gauge (68936-80,760 torr, Cole Parmer, USA). The Erlenmeyer was previously coupled to a closed valve named inlet 1 (41) in FIG. 23 that connects the artificial thigh. The system includes: an outlet 1 (30), an inlet 2 (31), an outlet 2 (32), a stainless fitting 33, an acrylic 34, "Artery" vinyl tubing 35, "Vein" vinyl tubing 36, a glass cylinder 37, a PZT 38, artificial bone 39, an acrylic 40, a stainless steel fitting 42, an injector device 42 and an air injector system 44.

Finally, the system was filled with approximately 2 liters. The next step was close the inlet 1, and the connections of the Erlenmeyer's output was connected to inlet 2. The vacuum flask was removed, and the vein and artery were filled with the leftover water.

Data Acquisition
Voltage Divider

Figure 24:
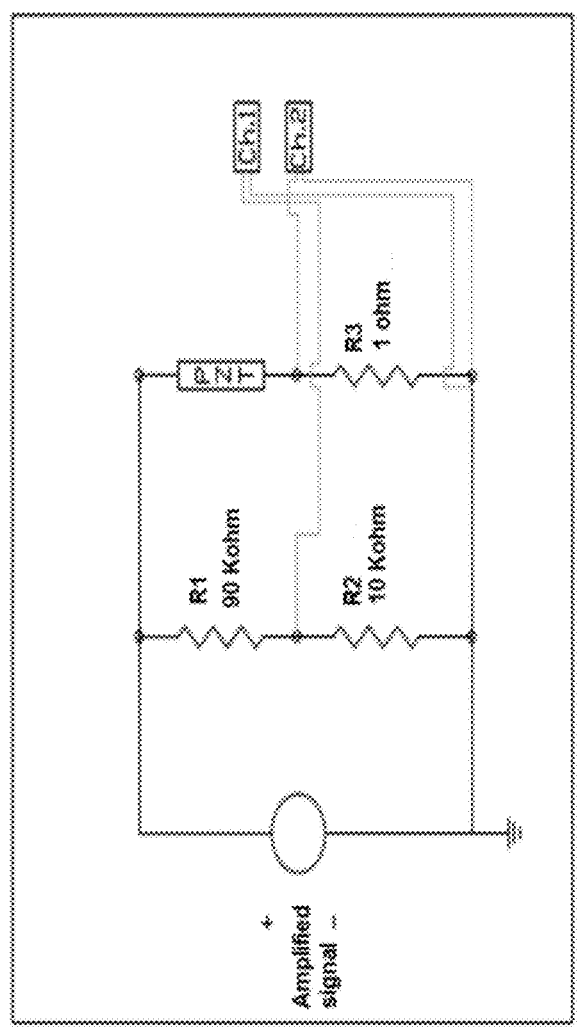
FIG. 24 shows en electrical diagram of a voltage divider circuit, according to the present invention.

A signal generator (3312A, Hewlett Packard Company, Palo Alto, Calif.) was connected to a PZT amplifier (EPA102, Piezo Systems Inc., Cambridge, Mass.).; the voltage from this device was 10 Vpp. When the signal passed through the amplifier, it was amplified 20 times, making the signal transmitted to the PZT ring 200 Vpp. Through a voltage divider (FIG. 24), which attenuated it 10.09, the voltage (20 Vpp) and current (250-270 mApp) signals were displayed on the oscilloscope. The oscilloscope (54615B, Hewlett Packard Company, Palo Alto, Calif.) and signal generator were connected via a GPIB (488.1, NI, Austin, Tex.) device to a computer.

Frequency Response

A program developed in Labview was used to measure the frequency response; this program acquired current and voltage signals on the PZT and computed the electrical admittance on the PZT ring as a function of frequency. Electrical admittance is a complex quantity; its real part corresponds to the conductance on the PZT ring, the maximum conductance coincides with the mechanical resonance.

Figure 25:
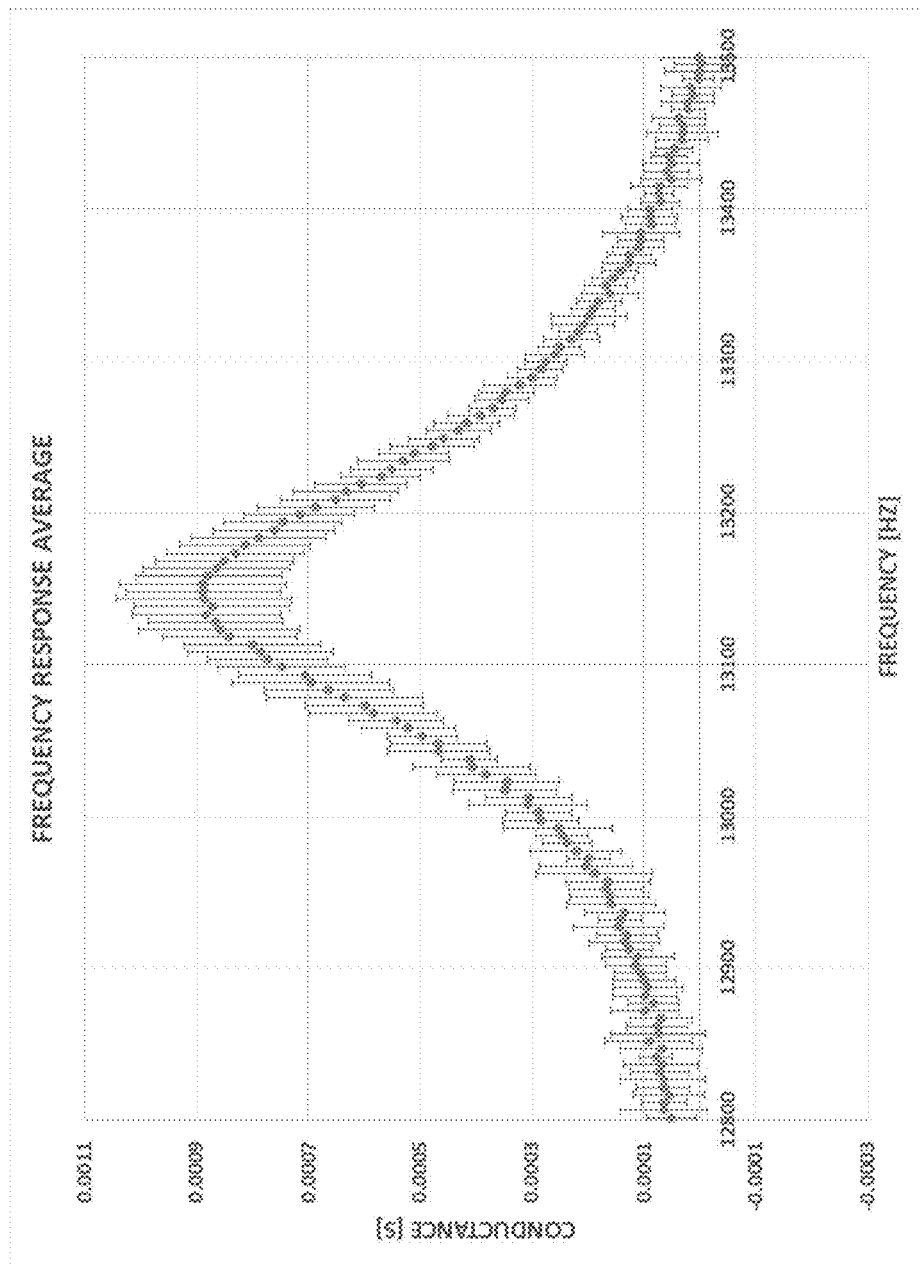
FIG. 25 shows a plot of the frequency response of the acoustic chamber, according to the present invention.

A typical frequency response is shown in FIG. 25, where the resonance frequency was (13,158±40) Hz. The frequency response should always be found previously to performing the experiment because it changes with environmental conditions. With the measured resonance frequency, the signal generator was configured to generate a sinusoidal signal at this frequency, resulting in the formation of a standing wave in the acoustic chamber. When the acoustic chamber was excited with a frequency that matched its first resonant mode, any minor disturbance in this medium was a measurable response through the PZT ring. Disturbances in this acoustic chamber were associated with the bubbles that were introduced into the system.

Data Acquisition Card

The data acquisition card (NI 6356, National Instruments Corporation, Austin, Tex.) is a device capable of operating its eight analog channels at a sampling frequency of 1.25 MHz. It also has two output analog channels and twenty-four digital channels of input and output (inputs and outputs are controlled by software). This device was configured to receive signals from the PZT ring using 5 analog channels.

Figure 26:
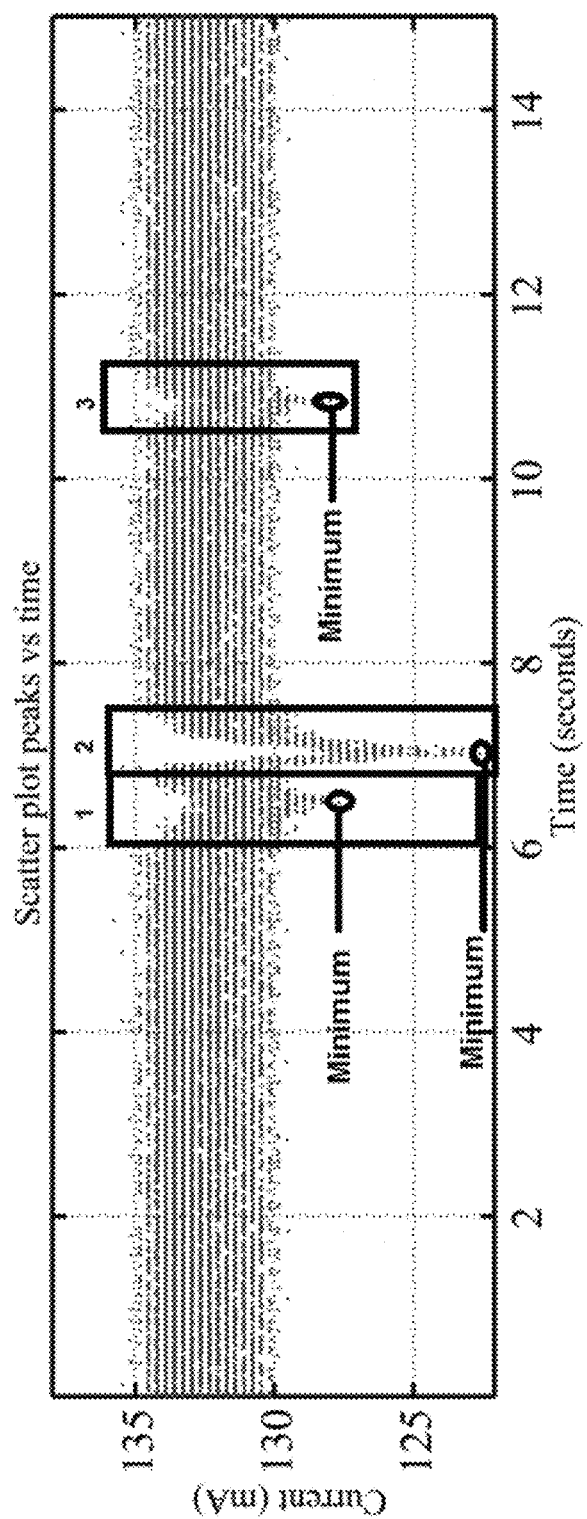
FIG. 26 shows a typical electrical current measured on the PZT and the effect of a passing bubble through it.

FIG. 26 shows a typical electrical current measured on the PZT and the effect of a passing bubble through it. Two different methods were used to analyze the electrical signals acquired from the PZT. In "method 1" the PZT was activated continuously while the bubbles were introduced into the system. The sample rate used to acquire data was 1 MHz, and the total time recoded was 20 seconds (20 Millions of samples data), initially capturing the first 10,000 samples of the signal, which has no bubbles. In this data set, the absolute value and then the value of maximum amplitude of each semi cycle is obtained.

In order to find the current drop an algorithm was developed to determine the minimum peak when the current drops due to the presence of a bubble crossing the PZT ring. The operation of the algorithm is:

1. From the peaks obtained in the algorithm, the "$z_{[n]}$" variable is created with samples than: $y_{[n]} <$ threshold.
2. The threshold is determined with the following equation:

$$\text{Threshold} = \overline{y_{[n]}} - \sigma_{y[n]} \quad (34)$$

with, $$\overline{y_{[n]}} = \left( \frac{1}{10000} \sum_{i=1}^{10000} \text{Amplitude\_max}_i \right) \quad (35)$$

$$\sigma_{y[n]} = \sqrt{\frac{1}{(9999)} \sum_{i=1}^{10000} (y_i - \overline{y_{[n]}})^2} \quad (36)$$

3. When the samples from "$y_{[n]}$" is: $y_{[n]} >$threshold, the minimum value of the variable "$z_{[n]}$" is calculated.
4. Calculate current drop as:

$$\text{Current\_drop}_{(n)}[\%] = \frac{|y_{(n)} - \text{Amplitude\_min}_{(n)}|}{y_{(n)}}(100\%) \quad (37)$$

However, when the PZT was turned on, some bubbles were broken into smaller ones, wherein some cases, they coalesced and in other cases, they continued oscillating close to the PZT without crossing it. From the above it was necessary to keep the PZT off in order to allow the bubbles to reach the middle of the acoustic chamber. After assuring this, the PZT is turned on. This permitted the control of the measurement of the bubble, thus the above method is called "method 2".

Figure 27:
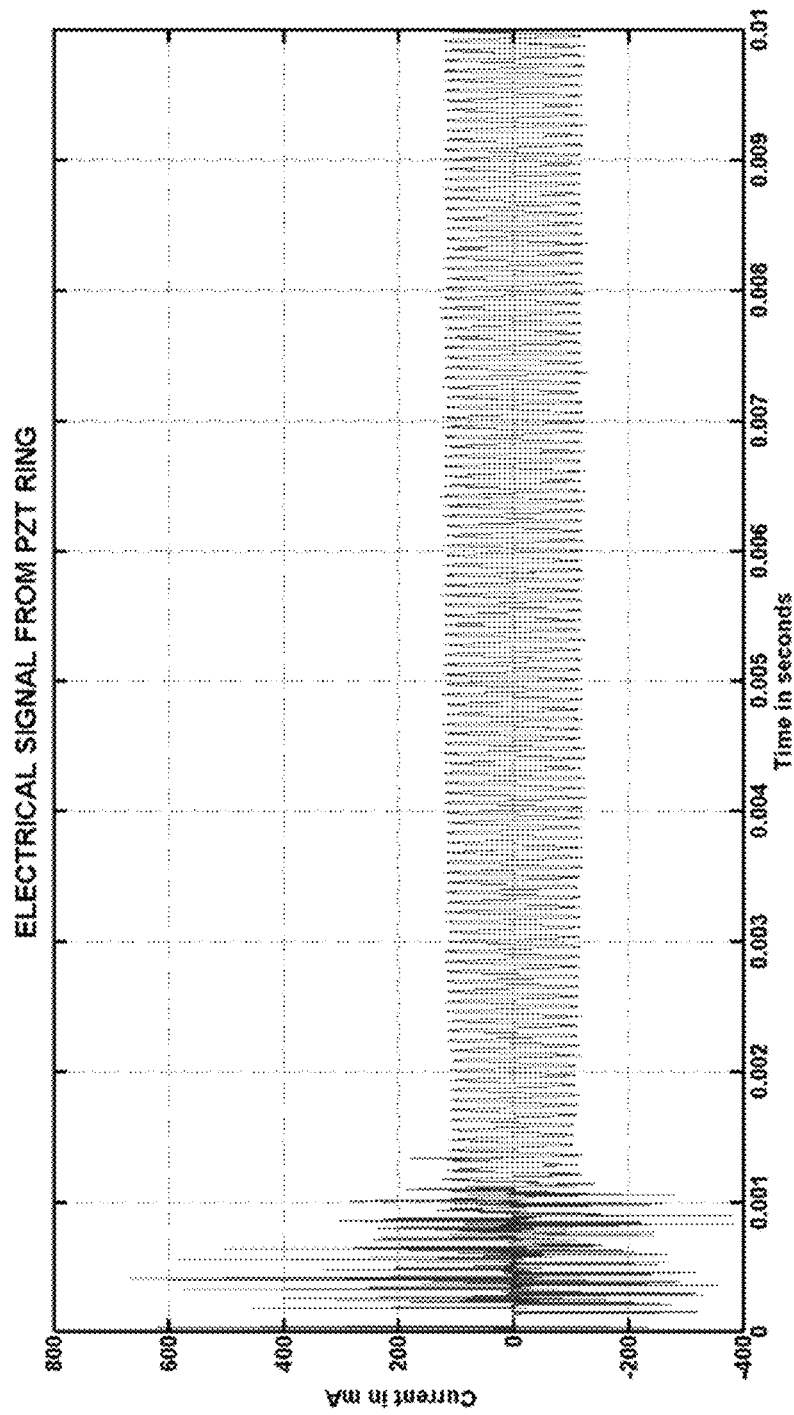
FIG. 27 shows a plot of the electrical signals using method 2, according to the present invention.

In method 2, it is necessary to acquire a reference signal (signal current without bubbles inside the acoustic chamber), and then acquire the current signal with induced bubbles into the acoustic chamber as shown in FIG. 27.

Experimentally, it was observed that the transient signal was between 9.5 ms to 10.8 ms. if the sampling frequency is 1 MHz; this means that approximately in the first 10000 samples is the transient part of the signal. Typically, signals in telecommunications are composed of the signal that carries the information, and the noisy signal. In our case, the electrical signals from the PZT "SB(n)" are shaped by the transient "$t_{SB}(n)$", and stationary signal "s(n)".

$$S_{B(n)} = t_{SB(n)} + s_{(n)} \quad (38)$$

Experimentally, a stationary signal without bubble "$S_{NB}(n)$" and a stationary signal with bubble "SB(n)" were processed without finding any difference in them. Both signals (with and without bubbles) remain the same amplitude. The signals can be expressed as:

$$S_{B(n)} = t_{SB(n)} + s_{(n)} \quad (39)$$

$$S_{NB(n)} = t_{SNB(n)} + s_{(n)} \quad (40)$$

The above equation (39) is subtracted from the equation (40), so the differential between electrical signals with bubble and without bubble is:

$$S_{NB(n)} - S_{B(n)} = t_{SNB(n)} + t_{SB(n)} \quad (41)$$

This subtraction indicates that the difference between the signals with $S_{B(n)}$ and $S_{NB(n)}$ is given by the transient signals. In order to identify the above difference between $S_{B(n)}$ and $S_{NB(n)}$, the root mean square was used for both signals and compared using the relative value. The equation for this process is:

$$\text{Relative value }[\%] = \frac{|SNB_{RMS(n)} - SB_{RMS(n)}|}{SNB_{RMS(n)}}(100\%) \quad (42)$$

High Speed Cameras

To perform a comparison between the electric signals on the PZT and the bubbles that were introduced into the system, two high-speed cameras (Speed Sense 9040 and Speed Sense 9090, Dantec Dynamics, Skovlunde, Denmark, DK-2740), hereafter called camera 1 (58') and camera 2 (58"), Speed Sense 9040 and Speed Sense 9090 respectively, were implemented in the process. Additionally, two LEDs (19 LED constellation systems and constellation 120, Tallahassee, Fla.) called LED 1 (59') and LED 2 (59"), respectively, were used. The image of the bubble leaving the bubble generation device provided the size of the bubble (camera 1), and the image of the bubble about to cross the PZT (camera 2) allowed the identification of the current drop associated to the particular bubble studied. Table 1 defines the settings for the cameras recording:

TABLE 1

|  | CAMERA 1 (9040) | CAMERA 2 (9090) |
|---|---|---|
| SAMPLE RATE | 100 | 100 |
| NUMER OF THE IMAGE | 2000 | 2000 |
| RESOLUTION IN AXIS X | 800 | 1200 |
| RESOLUTION IN AXIS Y | 600 | 800 |
| PIXE DEPTH | 8 | 8 |

Figure 28:
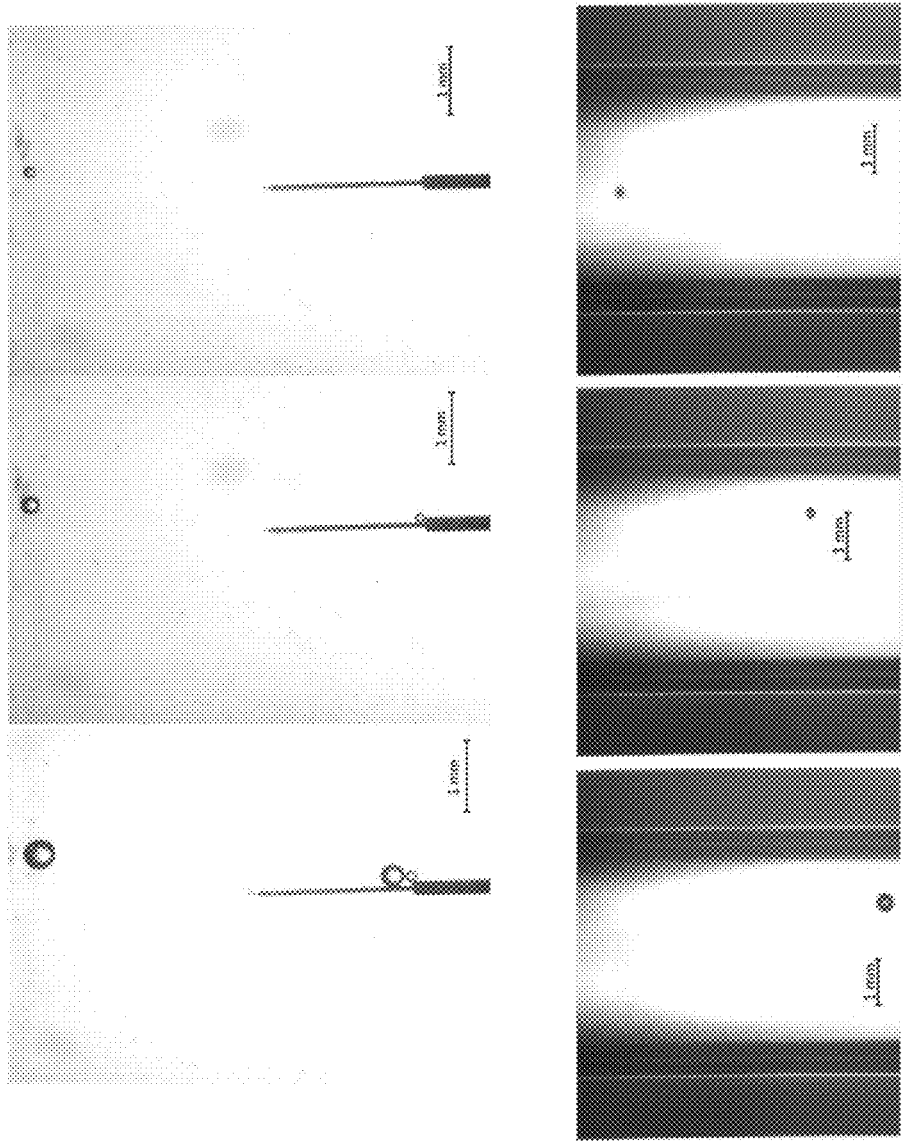
FIG. 28 shows images of bubbles in the bubble generator captured by camera 1 and 2.
Figure 29:
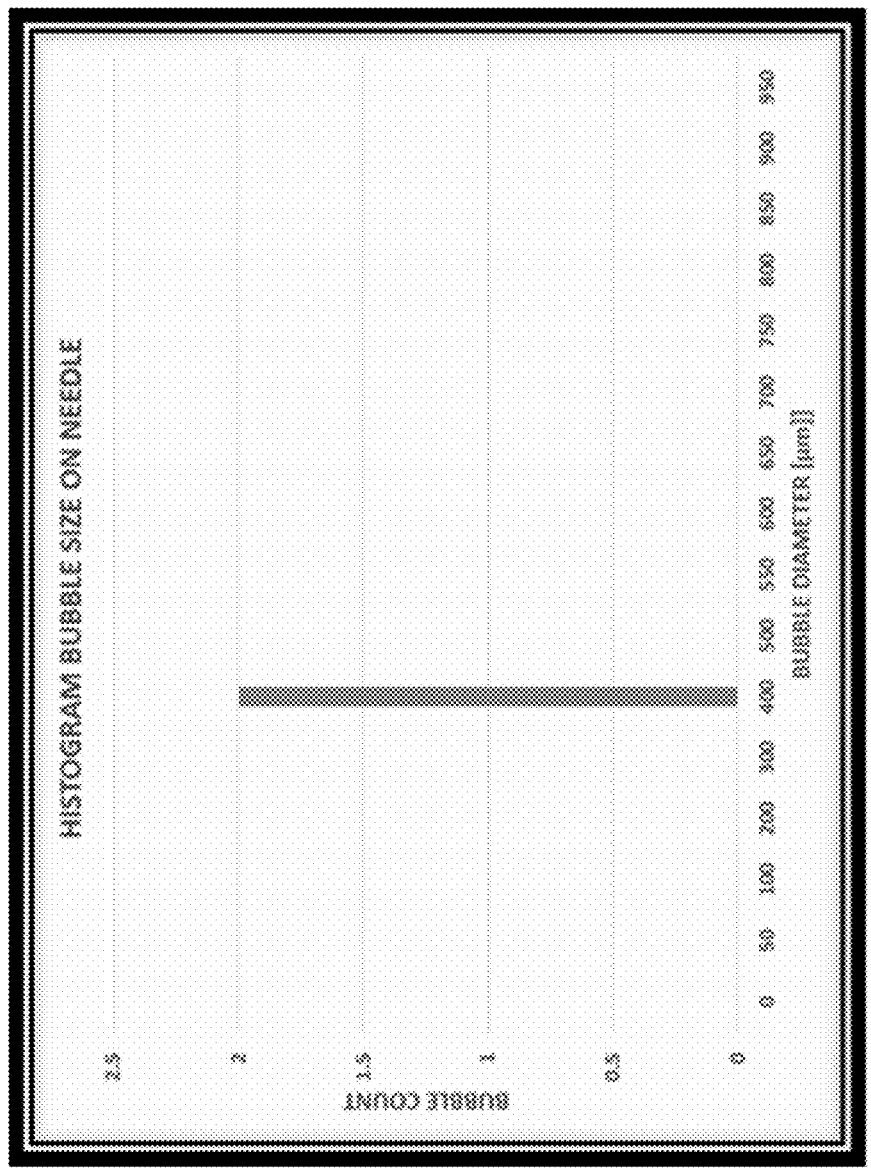
FIG. 29 shows a micro bubbles histogram of the needle.
Figure 30:
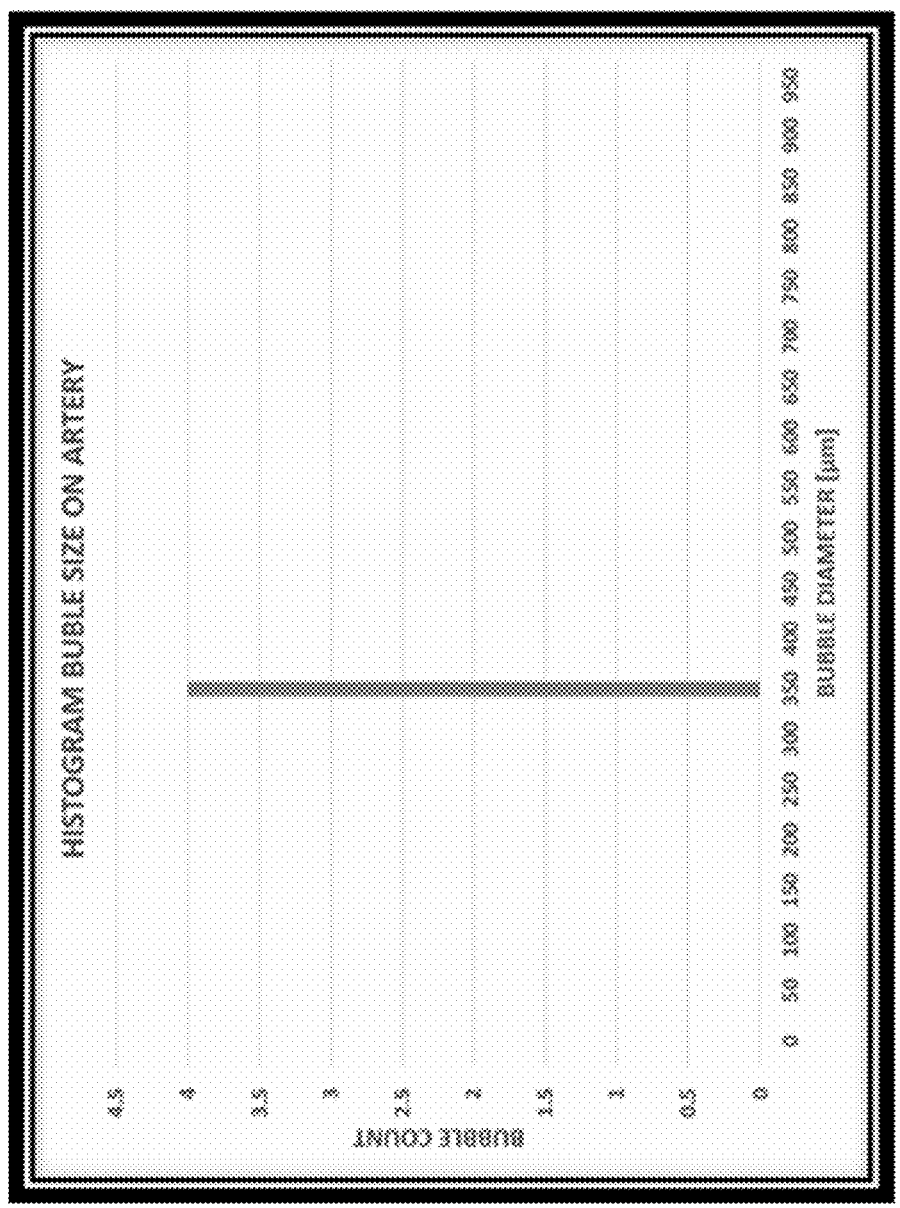
FIG. 30 shows a micro bubbles histogram of the artery.
Figure 31:
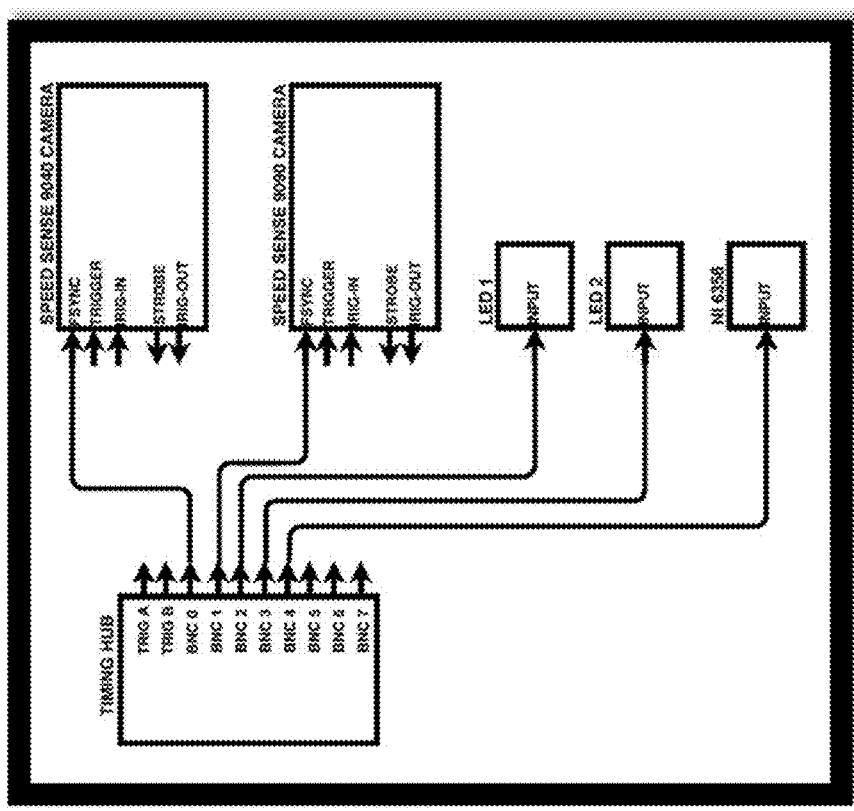
FIG. 31 shows a diagram of the timing hub settings.

FIGS. 28 and 29 are images of three bubbles of the bubble generating system as seen on camera 1 and 2, respectively. Using Dynamic Studio software, the image processing was performed by the shadow processing function where the bubble diameter recorded throughout the video was determined. FIG. 30 shows the histogram of micro bubbles upon activation of the bubble generator system. Generally, the generation of micro bubbles produced a population between 4-6 micro bubbles, the first to rise being the biggest bubble due to highest buoyancy. This bubble was the one used as a guide to enable the PZT. FIG. 31 shows the histogram from the artery.

Timing Hub

Figure 32:
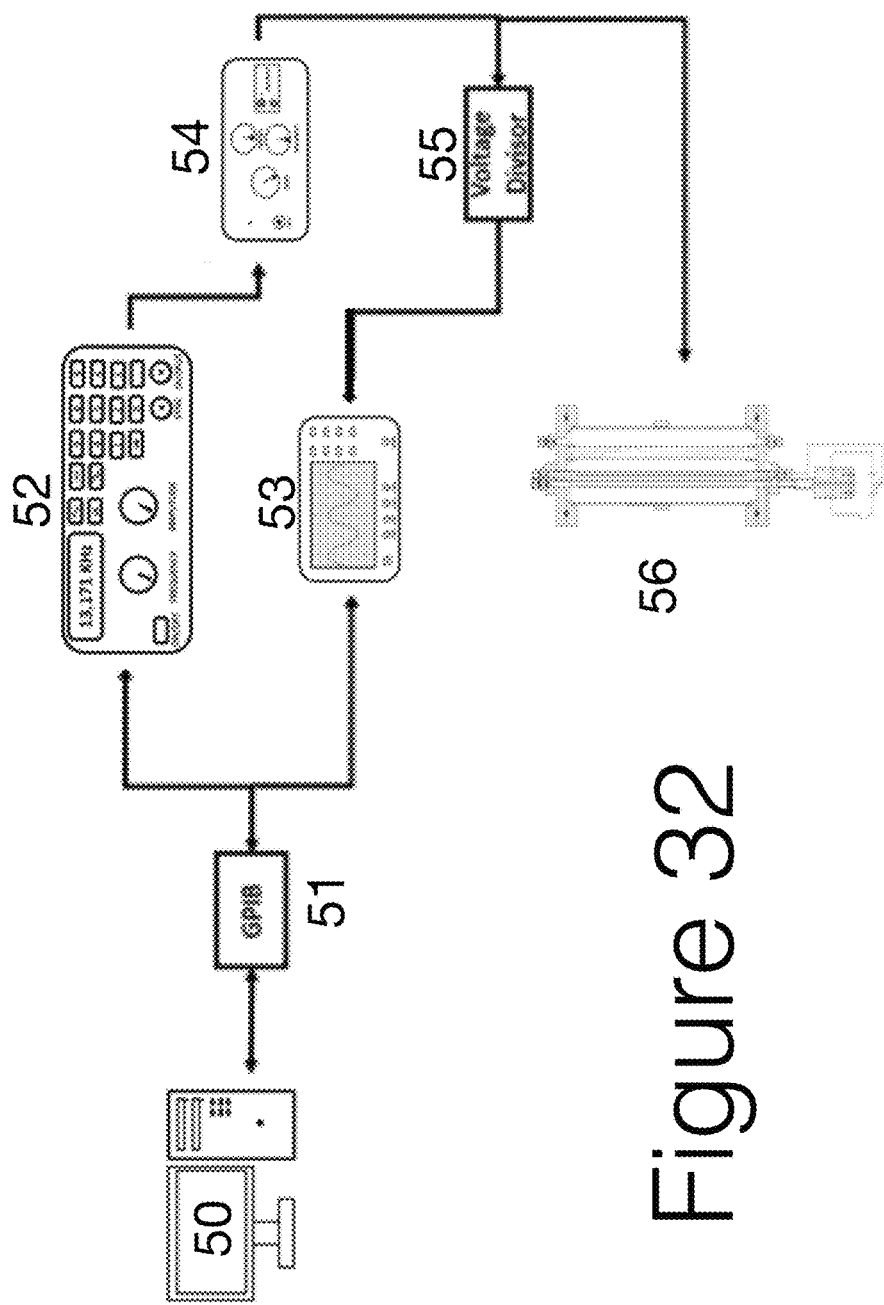
FIG. 32 shows the first experimental setup, according to the present invention.

The high-speed cameras were synchronized with the NI6356 card 57, since both devices were needed to estimate a relationship between the images of bubbles saved and the signals detected through the PZT ring. The synchronization of the devices previously mentioned (NI 6356, high speed cameras and LEDs) was performed with a timing hub 60 that used external or internal inputs as triggers. The timing hub had eight output ports. The configurations of the input and output ports (FIG. 32) were performed through Dynamic Studio (Version 3.14.35, Dantec Dynamics, Skovlunde, Denmark). The system also includes: a PC 50, a General Purpose Interface Bus (GPIB) 51, a waveform generator 52, an oscilloscope 53, a piezo amplifier 54 and a voltage divisor 55.

Figure 33:
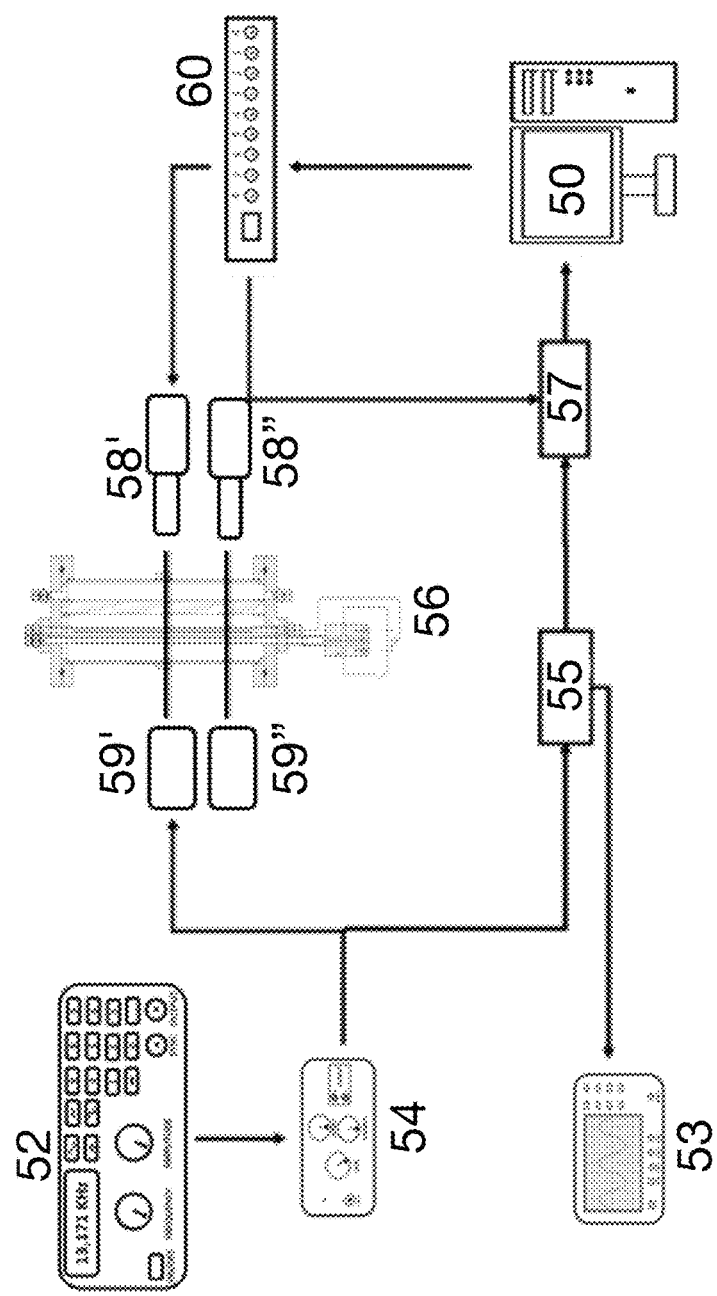
FIG. 33 shows the second experimental setup, according to the present invention.

The synchronization signal sent through the timing hub was 5 VDC (FIG. 33) and these signals were pulses that varied the frequency determined on the Dynamic Studio. The first signal emitted was a rising edge to the output port.

Experimental Protocol

A wave generated a signal that was induced into the prototype. This signal was observed by the oscilloscope. Both devices were connected via GPIB. The interface connection between computer, signal generator, and the oscilloscope was connected via GPIB by USB. Once the frequency response was found (using the experimental setup #1 shown in FIG. 34, the waveform generator was tuned to the resonance frequency.

Figure 35:
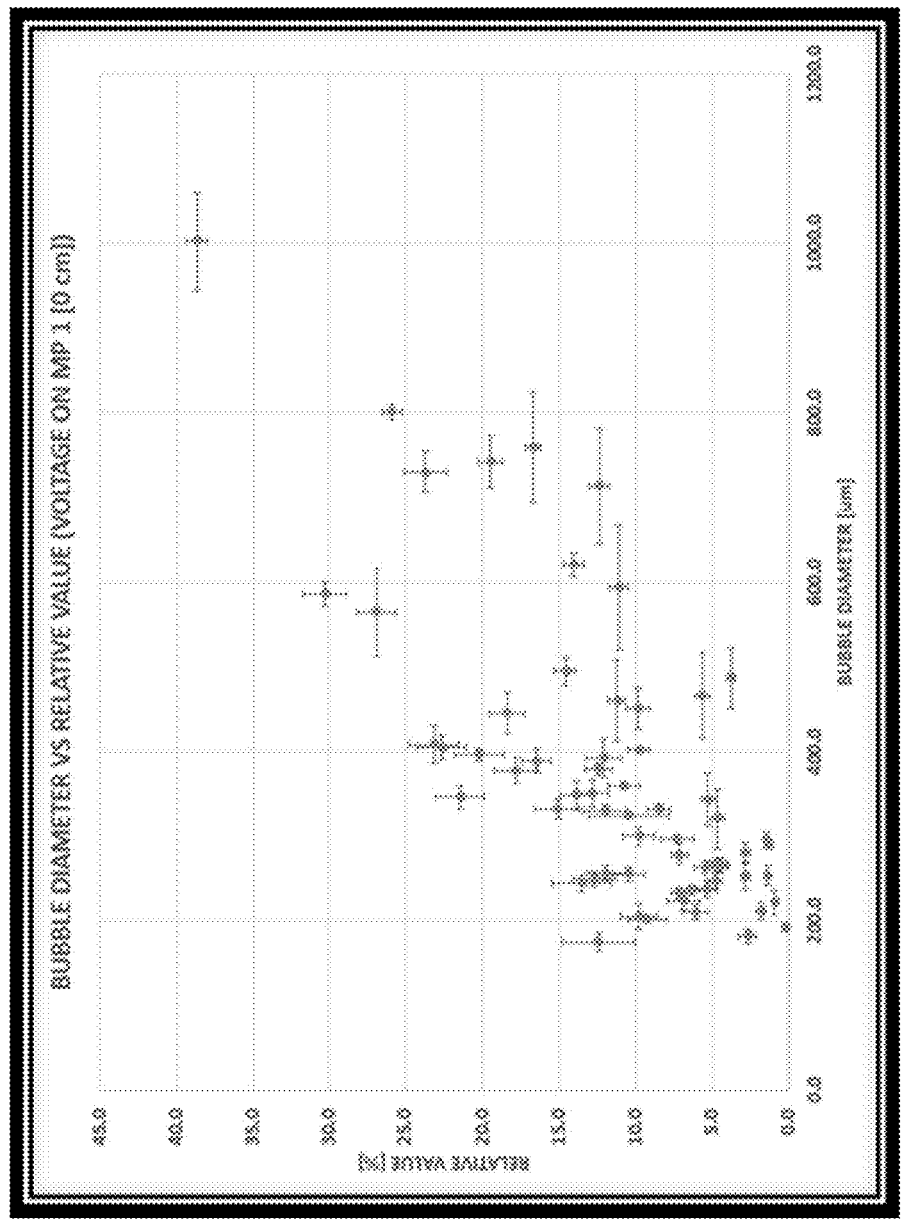
FIG. 35 shows the relationship between relative values from the voltage microphone and bubble diameter.

The next step is to activate the bubble generator system for recreating decompression sickness in the prototype. When activated, the timing hub started recording using the high-speed cameras and the data acquisition card using the experimental setup #2 shown in FIG. 35. When the bubble was close to the PZT, the PZT was activated.

Implementation of Classifiers

As previously explained, the relationship between current drop and bubble diameter was obtained and the associated sample signals (electrical signals from PZT and microphones MP1, MP2 and MP3) are the inputs to classifiers. The sample signals of the high-speed cameras are the references to determine the range of the classes. Table 2 below shows the input data which is read by the classifier algorithm:

TABLE 2

| Relative value [x] | Target [y] |
|---|---|
| 4.3 | 0 |
| 6.4 | 0 |
| 3.2 | 0 |
| 4.3 | 1 |
| 2.1 | 0 |
| 3.7 | 0 |
| 1.2 | 0 |
| 4.3 | 0 |
| 0.6 | 0 |
| 3.2 | 0 |
| 5.5 | 0 |
| 7.5 | 1 |
| 6.3 | 1 |
| 5.6 | 1 |
| 5.5 | 1 |
| 3.5 | 0 |
| 2.4 | 0 |
| 6.4 | 1 |
| 4.9 | 0 |

Support Vector Machine

The training step begins when the relative values are induced as features "x" of the equation (17) to determine the hyperplanes. To find the margin, the equation (23) is used. Finally, the weights "w" must be minimized to maximizing the separability between the classes "y" (equation (24)).

The algorithm was implemented with MATLAB. The toolbox used in MATLAB applied kernels functions and the linear kernel implemented was expressed as:

$$k(x_i, x_j) = x_i^T x_j \qquad (43)$$

In order to determine the classification for the new data, the addition of the similarities is computed:

$$\text{Predict} = \text{sgn} \Sigma_{i=1}^{N} w_i y_i k(x_i, x_j) \qquad (44)$$

With,

Predict; kernel classifier predict label to unlabeled inputs.

sgn; it is an odd mathematical function that extracts the sign of a real number.

$w_i$; weights obtained from the training data.

$y_i$; the targets obtained from the training data.

Artificial Neural Networks

Table 2 above is an example of the inputs data that neural networks algorithms receive for processing. The NN toolbox of the MATLAB software was used. Initially, the inputs are used as training data, with inputs and targets known. The weights and bias (the initial value of the bias "b" is zero) are detected, to which the error between update targets and estimate targets is zero. The expression to calculate the weights is:

$$\text{weight}_{new(i+1)} = \text{weight}_{old(i)} + y_i * x_i \qquad (45)$$

The output expression when the update has been induced can be shows as:

$$\text{output}_i = \text{weight}_{new(i)} * x_i \quad (46)$$

The iterations are stopped when the calculated error between the "$\text{weight}_{new(i+1)}$" and "$\text{weight}_{old(i)}$" remains unchanged.

K-Mean

The relative value of the bubble diameter was used because this method generates data clustering. When the cluster has been determinated, an algorithm was developed to predict the new samples. Each sample is joined to each cluster. The standard deviation is calculated for each cluster too, the minimum variation indicates which sample belongs to these clusters.

Experimental Results

Result Obtained from the Features Extraction

Bubble in Middle of the PZT Ring

Figure 36:
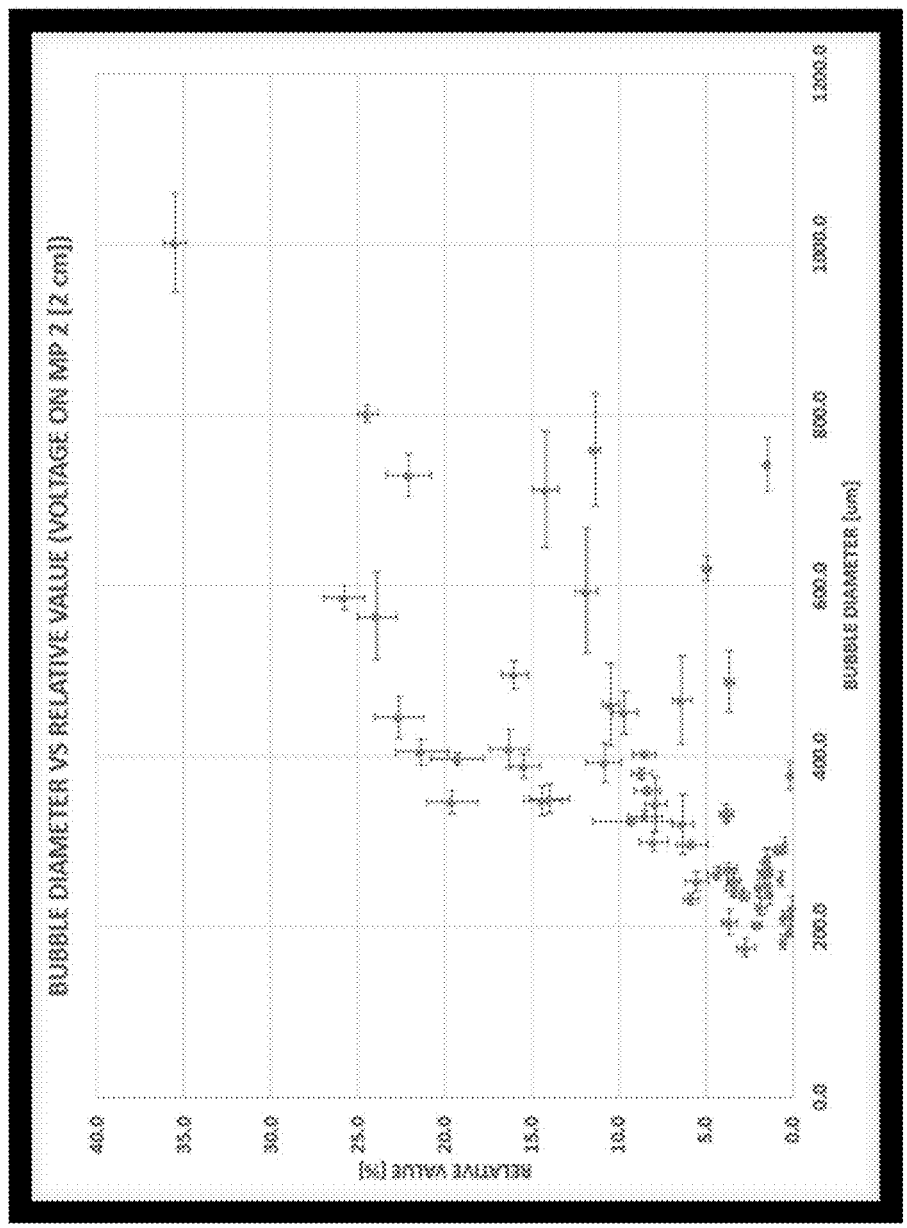
FIG. 36 shows data obtained measuring the voltage in a pill microphone located 2 cm from the bottom edge of the PZT when the PZT was actuated when the bubble reached the PZT center.

The relative values and bubble size diameter from bubbles crossing the PZT ring generate a relationship as shown in FIG. 36 where the effect of bubble size measured in the PZT when it is actuated at the time the bubble reaches the PZT center can be appreciated. The error bars were computed based on the DAQ card precision and the error propagation of the relative value of the difference in root mean square and the number of samples=126.

Without having a linear relationship, the curve was narrowed at different intervals as shown in FIG. 36. Initially, this curve was divided into two ranges: larger bubbles than 500 microns and under bubbles than 500 microns. In others word, the step "one" has a setup as: interval's range is 500 μm and the amount of ranges is 2. The second step is changing the range intervals to 200 μm, which increases the amount of range to 5 (The K-mean algorithm was used to determine the amount of classes).

Figure 37:
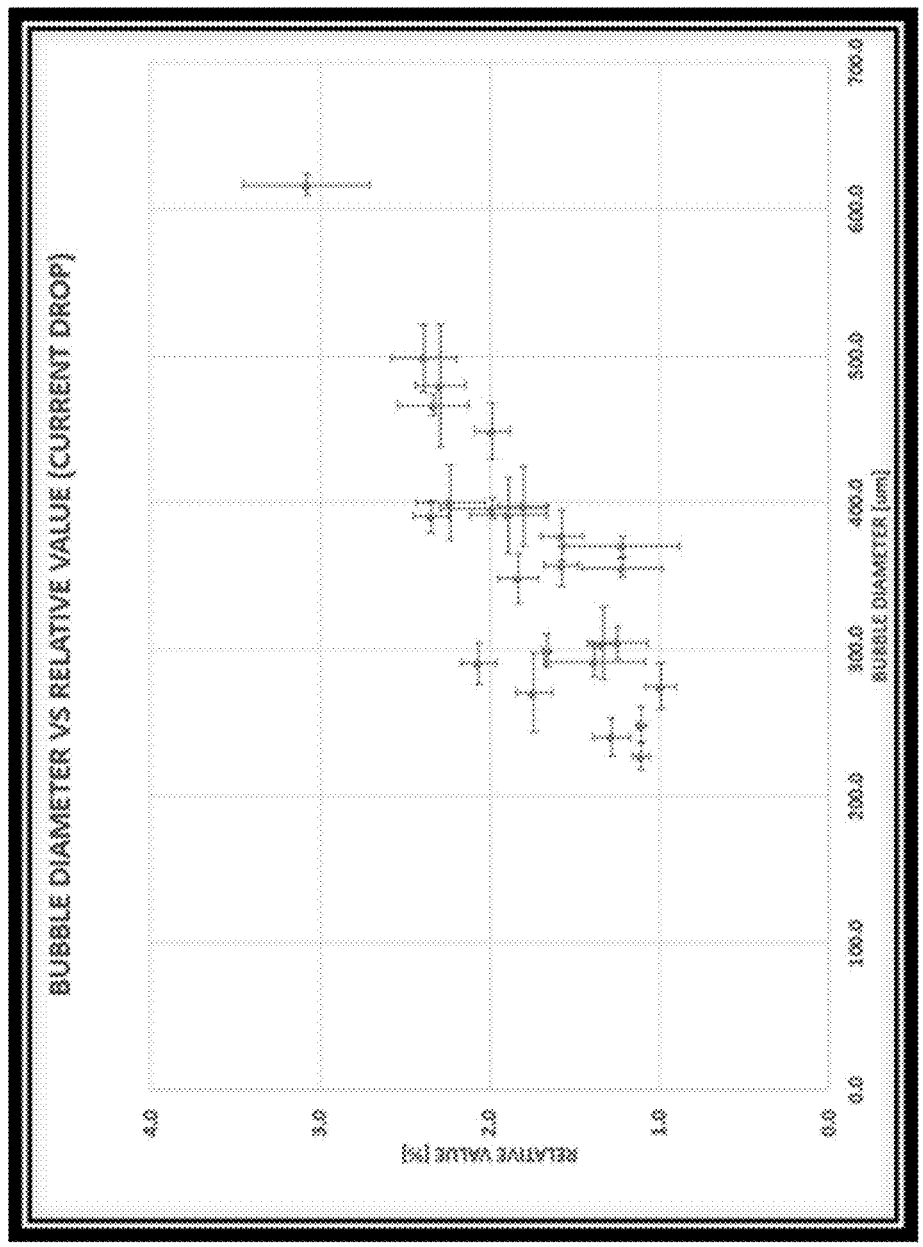
FIG. 37 shows data obtained when the PZT was actuated when the bubble was located at 1 cm from the PZT.

For the steps above, the accuracy and error in the bubbles detection is analyzed by means of tables of confusion. In order to take advantage of other observations and improve the estimate in the detection of bubbles, the signals captured by the microphones were also processed obtaining relative value from the voltage microphone and bubble diameter as shown in FIG. 37 where data was obtained measuring the voltage in a pill microphone located at the bottom edge of the PZT when the PZT was actuated when the bubble reached the PZT center and the number of samples=63.

In summary, the data obtained when the bubble crosses through the PZT are:

Electrical signal from PZT ring with 126 samples.
Electrical signal from "MP1" with 63 samples
Electrical signal from "MP2" with 38 samples.
Electrical signal from "MP3" with 63 samples.

Figure 38:
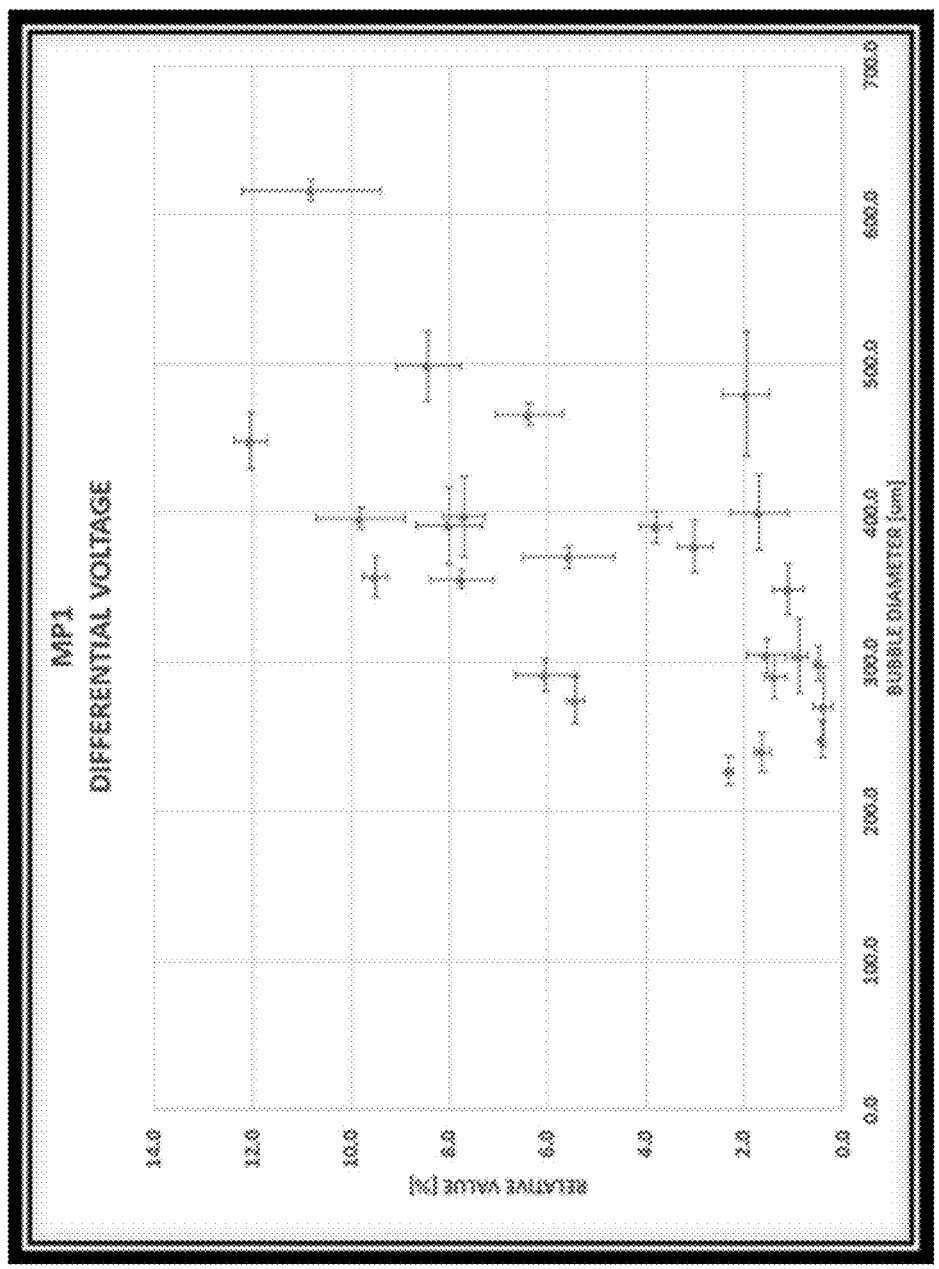
FIG. 38 shows data obtained measuring the voltage in a pill microphone located at the bottom edge of the PZT when the PZT was actuated when the bubble was located at 1 cm from the PZT.

The differences are due to some test being developed with microphones at 0 cm, 2 cm and 4 cm from bottom edge of the PZT, and others were changed to 0 cm, 1 cm and 2 cm. When it was observed that the PZT bubbles were not detected beyond 2 cm (FIG. 38, where data was obtained measuring the voltage in a pill microphone located 2 cm from the bottom edge of the PZT when the PZT was actuated when the bubble reached the PZT center and the number of samples=63.), the microphone signal acquired at 4 cm was suppressed. However, the microphones signals common for all test are PZT, MP at 0 cm and MP at 2 cm.

Bubbles Located 1 cm from the PZT Ring

Figure 39:
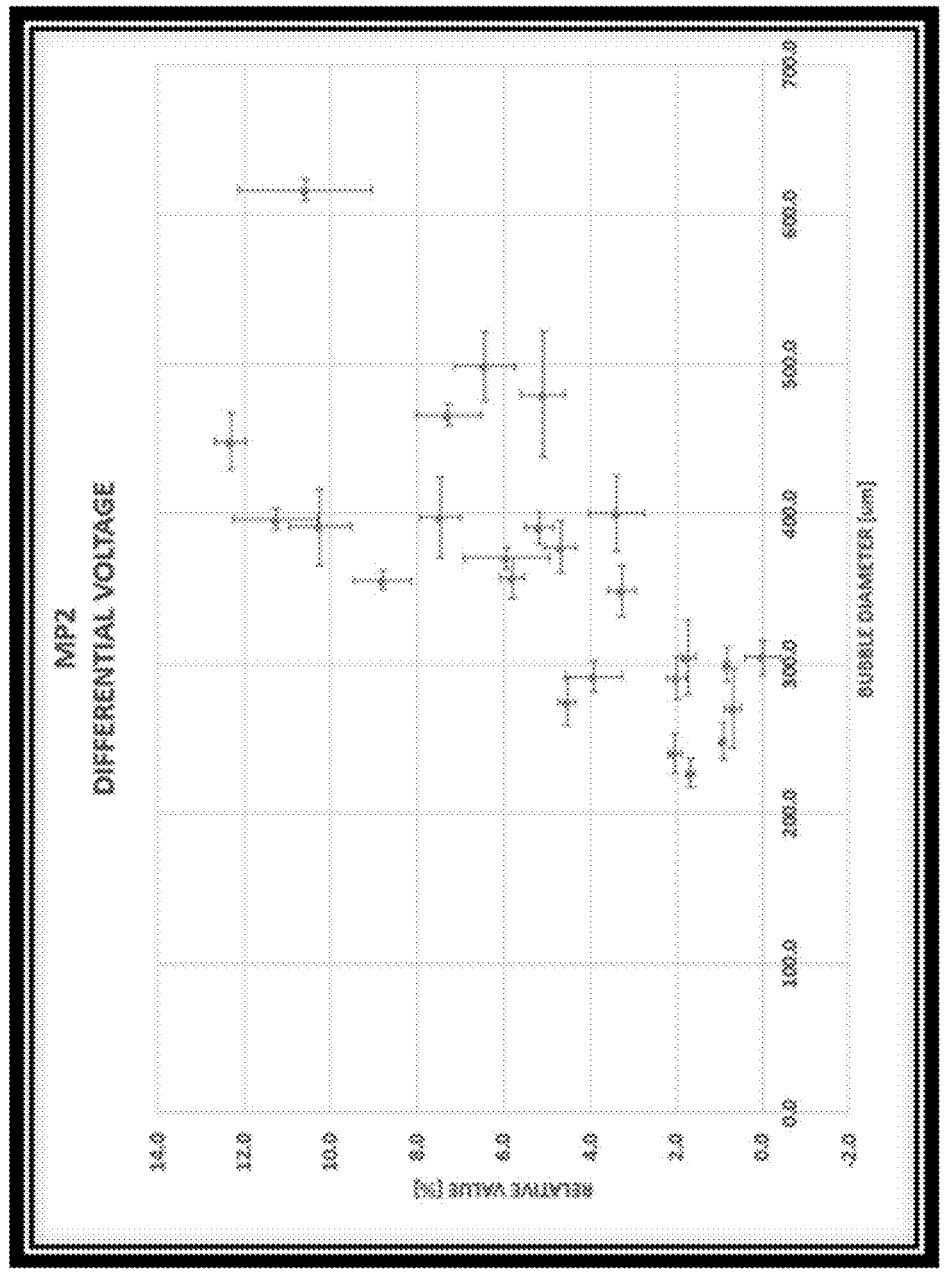
FIG. 39 shows data obtained measuring the voltage in a pill microphone located at 1 cm from the bottom edge of the PZT when the PZT was actuated when the bubble was located at 1 cm from the PZT.
Figure 40:
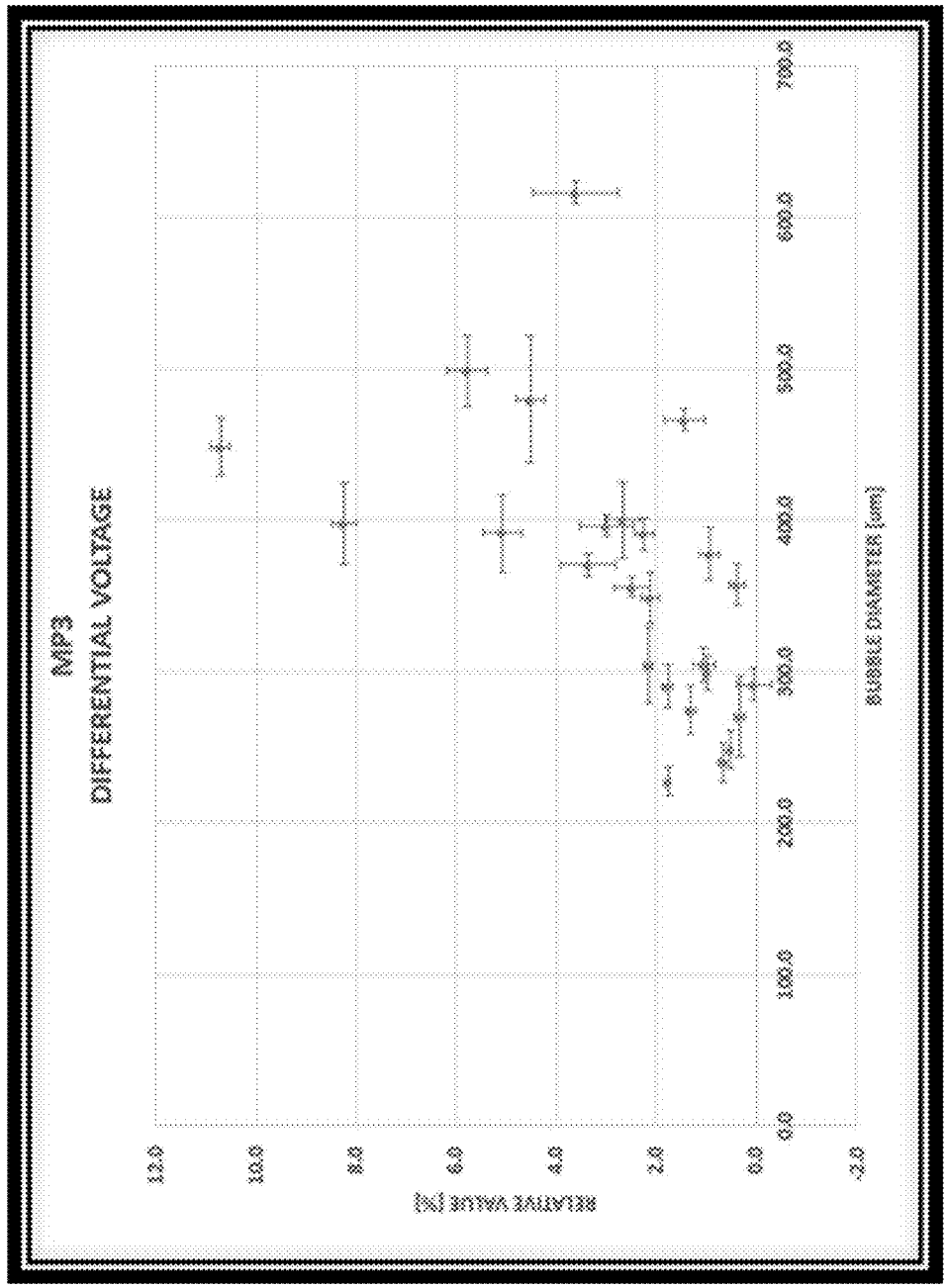
FIG. 40 shows data obtained measuring the voltage in a pill microphone located 2 cm from the bottom edge of the when the PZT was actuated when the bubble was located at 1 cm from the PZT.
Figure 41:
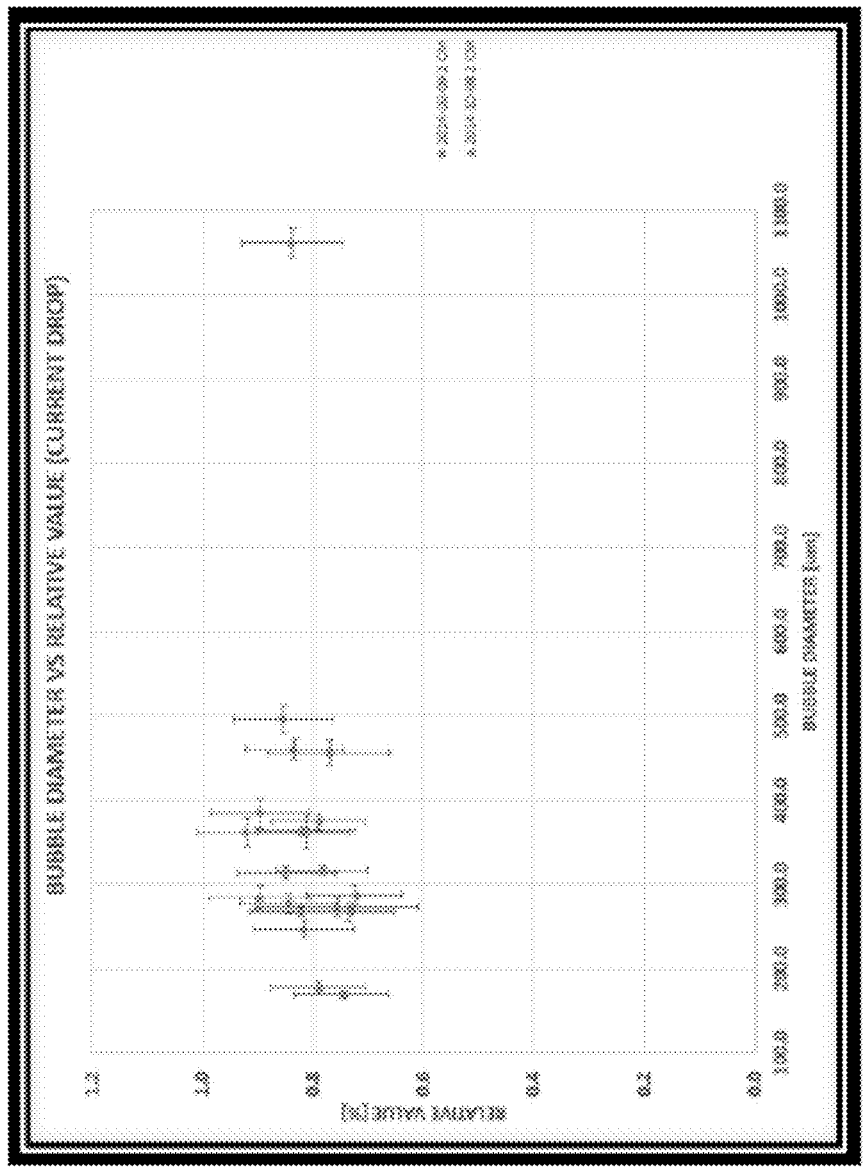
FIG. 41 shows data obtained when the PZT was located actuated when the bubble was at 2 cm below the PZT.
Figure 42:
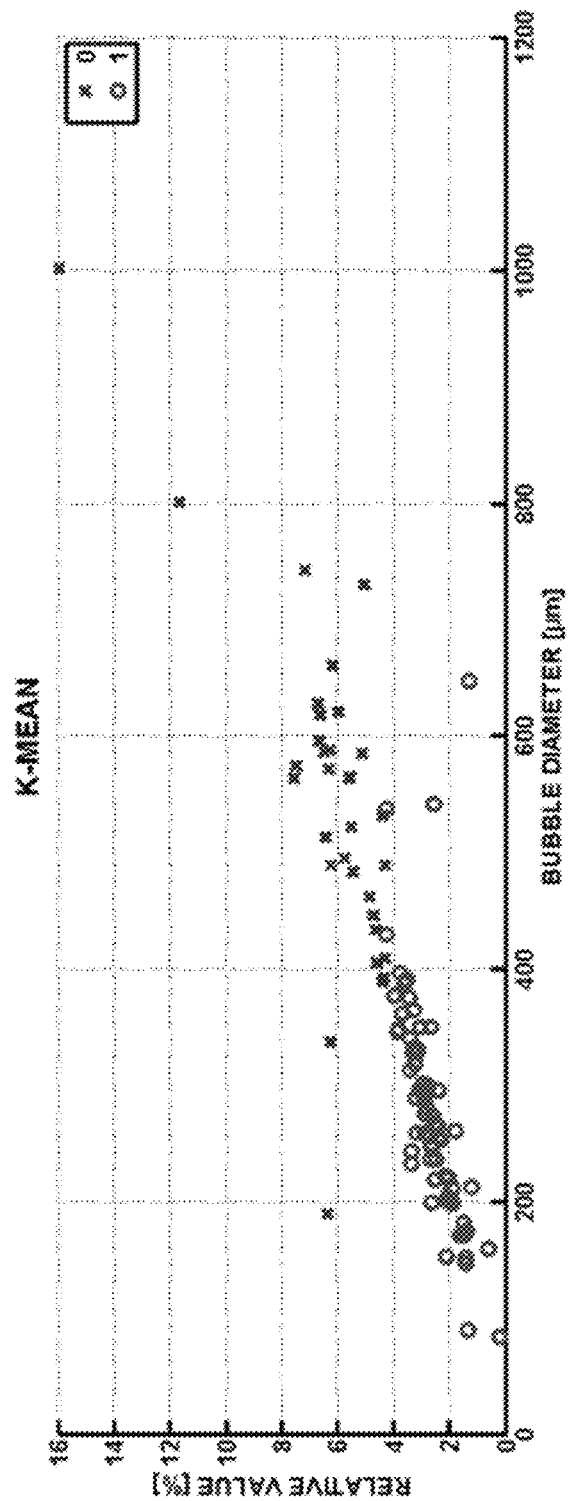
FIG. 42 shows the prediction of the K-mean algorithm response with 100 data samples.

When applying the "Method 2", a new condition needs to be considered. If the system will detect the bubbles by operating the PZT randomly, the minimum distance for bubble detection must be determined. In order to find the ring PTZ sensitivity, some tests were performed actuating the PZT to 1 cm from the bottom edge of this one. FIG. 39 shows the relative value ratio and bubble diameter from the PZT ring. Information was also acquired from microphones at 0 cm (FIG. 40, number of samples=38), 1 cm (FIG. 41, number of samples=38) and 2 cm (FIG. 42, number of samples=38) from the bottom edge of PZT ring.

Bubbles Located 2 cm from the PZT Ring

Figure 43:
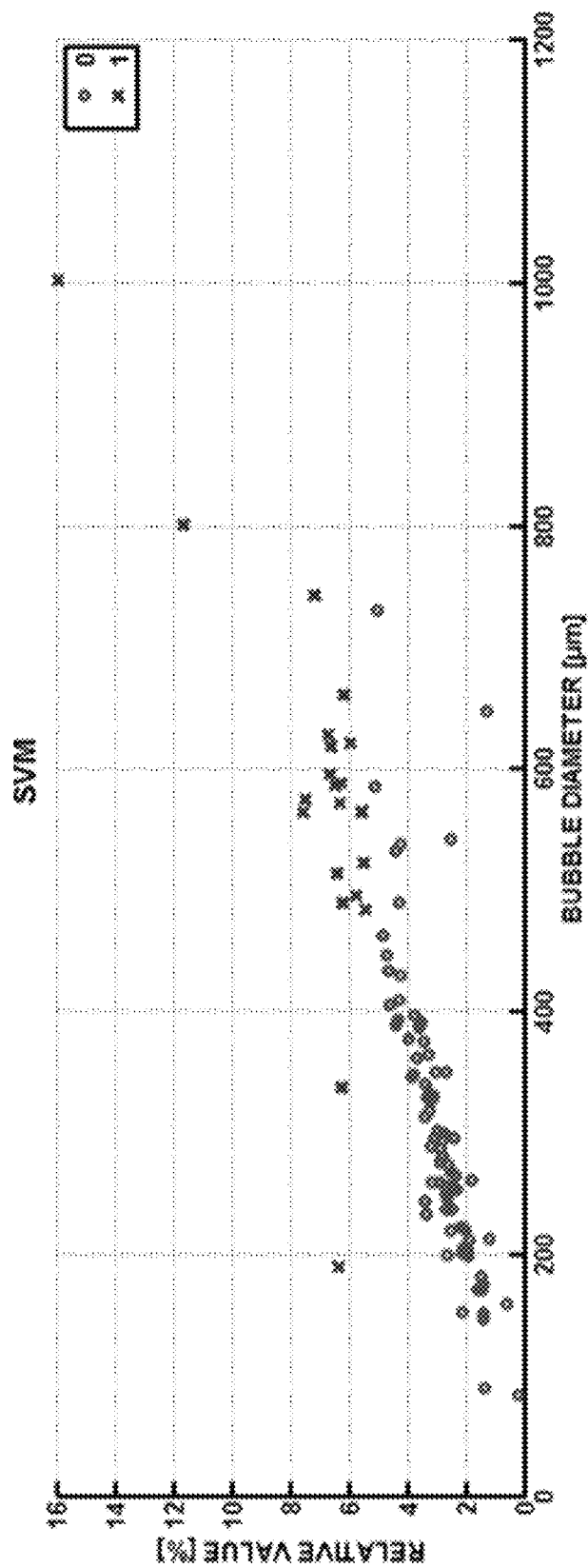
FIG. 43 shows the results of the SVM algorithm with 100 data samples.

From the data shown in FIG. 43, where data was obtained when the PZT was located and actuated when the bubble was at 2 cm below the PZT and the number of samples=20, it can be concluded that if bubbles are further away than 2 cm from the PZT, the system cannot detect them.

Bubble Detection with 1 Feature for 2 Classes

Initially, the relationship between "relative value vs bubble size diameter" was classified into 2 types. Class "o" indicates the bubbles with a diameter less than 500 μm and class "x" are bubbles larger than 500 μm. Different classifiers were used for the training data 3. The training step was developed for the three classifiers.

K-Mean

Figure 44:
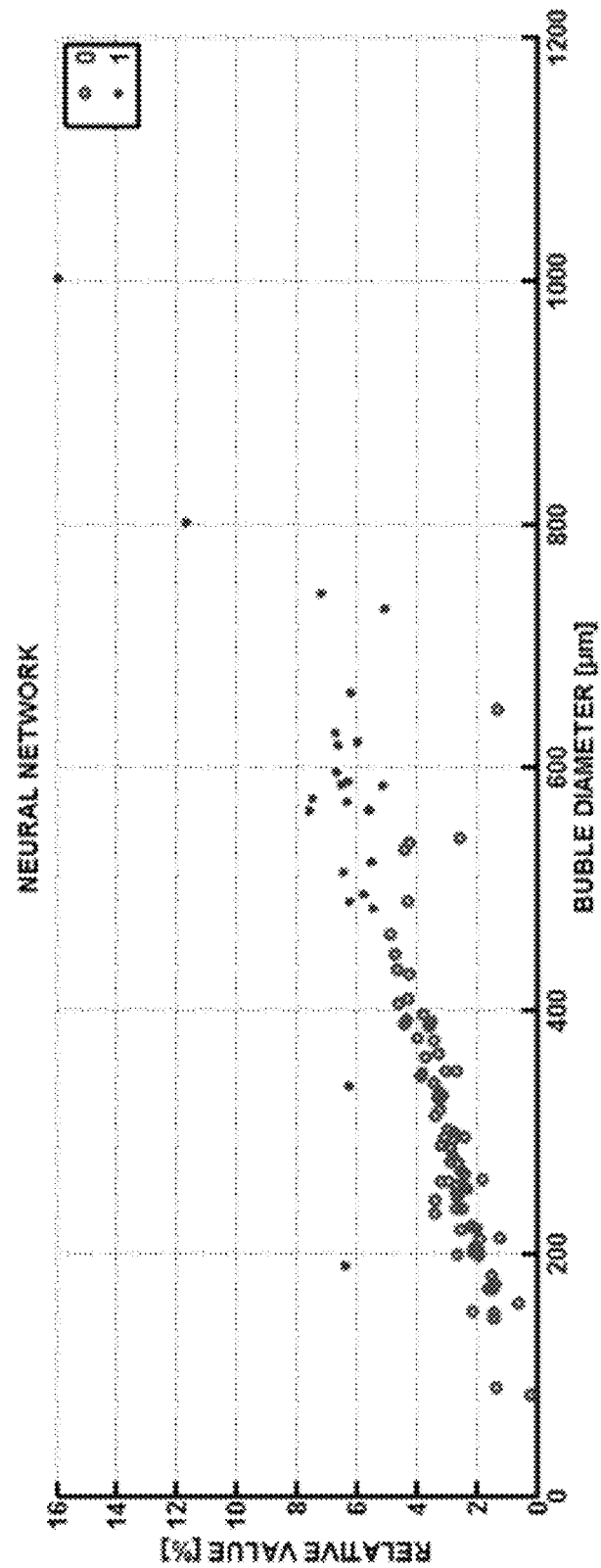
FIG. 44 shows the results of the NN algorithm with 100 data samples.

Prediction of the K-mean algorithm (added STD predictor) was used when 100 data samples corresponding to the PZT were being actuated when the bubbles were at its center. "0" represents bubbles predicted to have a size smaller than 500 μm and "1" represents bubbles bigger than 500 um as shown in FIG. 44. Table 3 below indicates the real data (vertically), and the data detected by the K-mean algorithm (horizontally) to 1 feature and 2 classes.

TABLE 3

|  |  | Real | | |
| --- | --- | --- | --- | --- |
|  |  | 0 | 1 | Total |
| K-mean | 0 | 64 | 3 | 67 |
|  | 1 | 13 | 20 | 33 |
|  | Total | 77 | 23 | 100 |

The accuracy and error in bubble detection are:

$$\text{Accuracy} = \frac{84}{100} = 0.94$$

$$\text{Error} = \frac{16}{100} = 0.16$$

SVM

Figure 45:
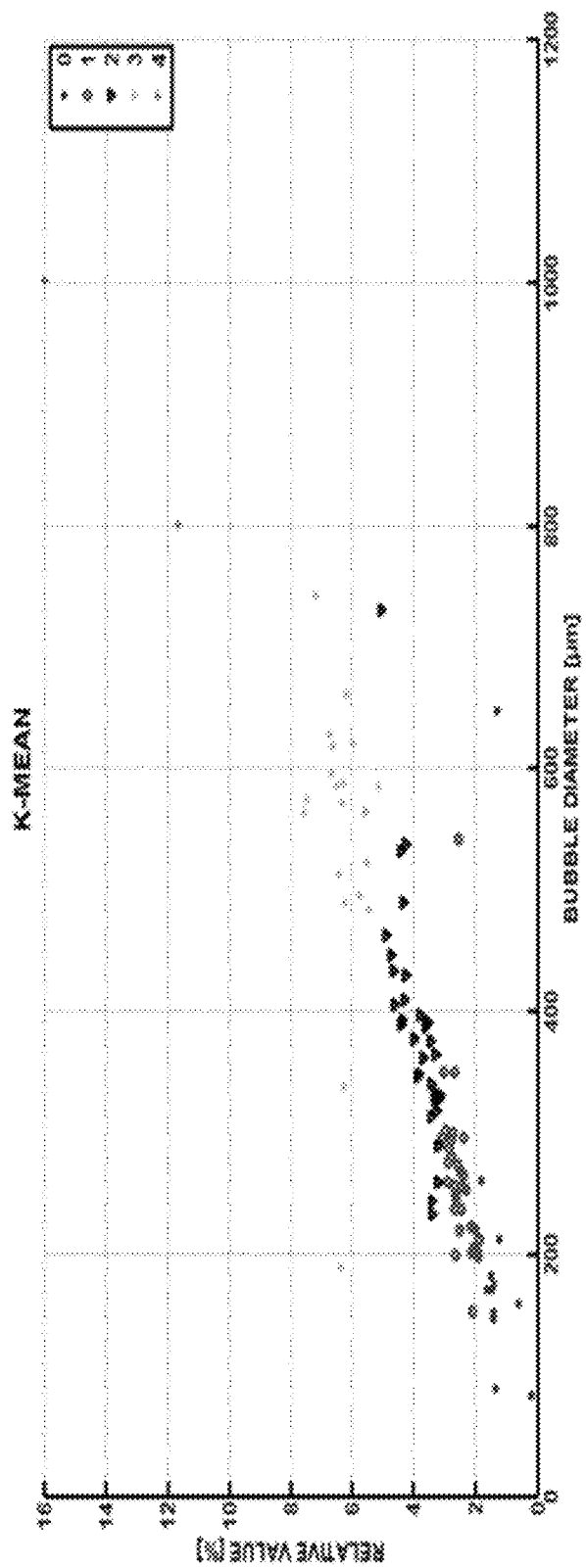
FIG. 45 shows the prediction of the K-mean algorithm was used when 100 data samples corresponding to the PZT were being actuated when the bubbles were at its center.

Predicted results of the SVM algorithm were used when 100 data samples corresponding to the PZT were being actuated when the bubbles were at its center (see FIG. 45). "0" represents bubbles predicted to have a size smaller than 500 um and "1" represents bubbles bigger than 500 um.

Table 4 below shows the real data samples (vertically), with the data detected by the SVM algorithm (horizontally).

TABLE 4

|  |  | Real | | |
|---|---|---|---|---|
|  |  | 0 | 1 | Total |
| SVM | 0 | 72 | 6 | 78 |
|  | 1 | 5 | 17 | 22 |
|  | Total | 77 | 23 | 100 |

The accuracy and error in bubble detection are:

$$\text{Accuracy} = \frac{89}{100} = 0.89$$

$$\text{Error} = \frac{11}{100} = 0.11$$

NN

Figure 46:
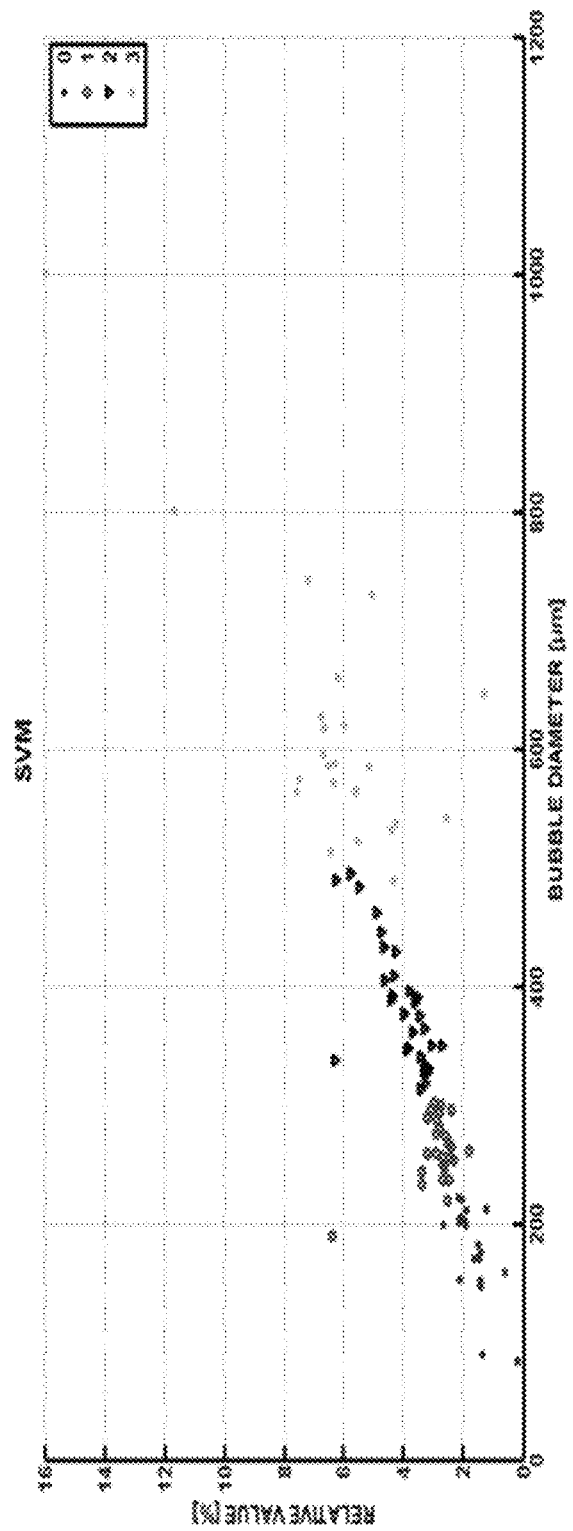
FIG. 46 shows the prediction of the SVM algorithm was used when 100 data samples corresponding to the PZT were being actuated when the bubbles were at its center.

FIG. 46 shows the predicted results of the NN algorithm when 100 data samples corresponding to the PZT being actuated when the bubbles were at its center were used. "0" represents bubbles predicted to have a size smaller than 500 um and "1" represents bubbles bigger than 500 um.

Table 5 below shows the real data (vertically), with the data detected by the NN algorithm (horizontally) to 1 feature and 2 classes.

TABLE 5

|  |  | Real | | |
|---|---|---|---|---|
|  |  | 0 | 1 | Total |
| NN | 0 | 72 | 4 | 74 |
|  | 1 | 5 | 19 | 26 |
|  | Total | 77 | 23 | 100 |

The accuracy and error in bubble detection are:

$$\text{Accuracy} = \frac{91}{100} = 0.91$$

$$\text{Error} = \frac{9}{100} = 0.09$$

Bubble Detection with 1 Feature for 5 Classes

The detection of the bubbles has been performed using the current signal and bubble diameter information divided into 5 classes. The 5 classes have been determined using the K-mean as reference. The K-mean classification was:

TABLE 6

| Label | Interval |
|---|---|
| 0 | bubbles smaller than 220 μm |
| 1 | 220 μm and 330 μm |
| 2 | 330 μm and 480 μm |
| 3 | 480 μm and 660 μm |
| 4 | bubbles bigger than 660 μm |

K-Mean

Figure 47:
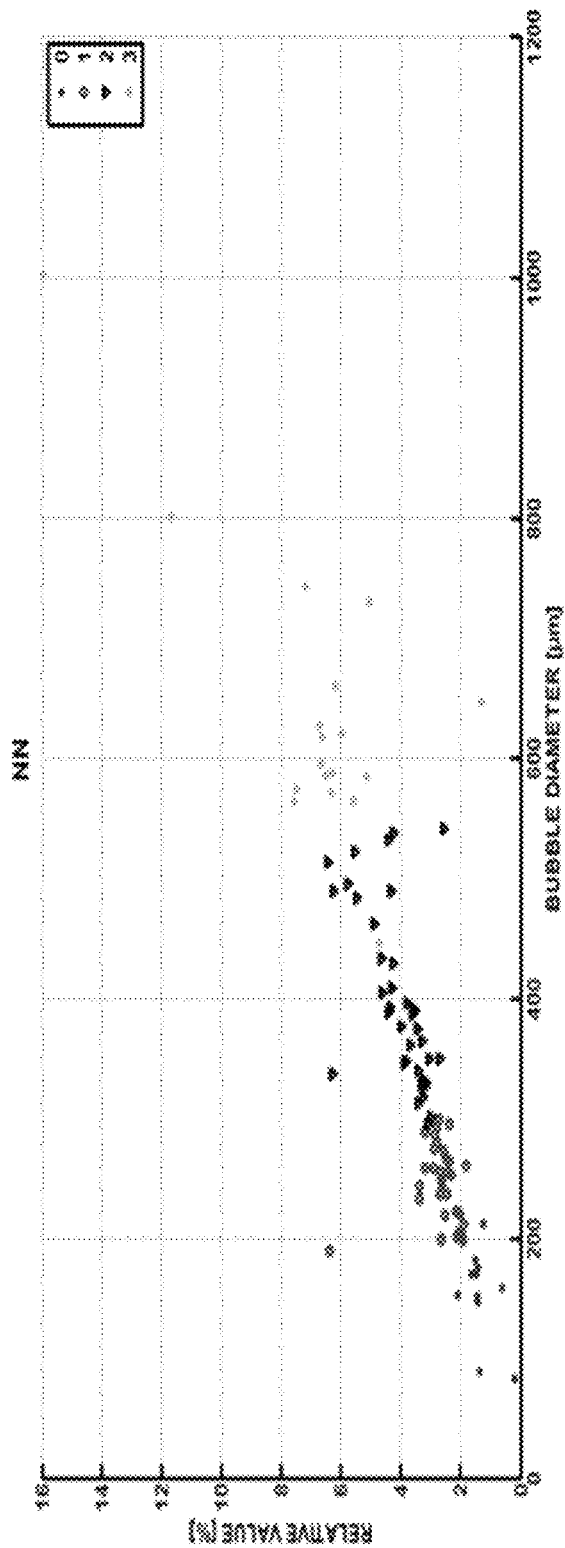
FIG. 47 shows the prediction of the NN algorithm was used when 100 data samples corresponding to the PZT were being actuated when the bubbles were at its center.

FIG. 47 shows the prediction of the K-mean algorithm when 100 data samples were used corresponding when the PZT was being actuated when the bubbles were at its center. Table 7 below indicates the intervals in which predictor K-mean algorithm detected bubbles.

TABLE 7

|  |  | Real | | | | | |
|---|---|---|---|---|---|---|---|
|  |  | 0 | 1 | 2 | 3 | 4 | Total |
| KMEAN | 0 | 9 | 3 | 0 | 1 | 0 | 13 |
|  | 1 | 2 | 25 | 4 | 0 | 0 | 31 |
|  | 2 | 0 | 3 | 26 | 4 | 0 | 33 |
|  | 3 | 1 | 1 | 2 | 15 | 0 | 19 |
|  | 4 | 0 | 0 | 1 | 1 | 2 | 4 |
|  | Total | 11 | 34 | 28 | 24 | 3 | 100 |

The accuracy and error in bubble detection are:

$$\text{Accuracy} = \frac{77}{100} = 0.77$$

$$\text{Error} = \frac{23}{100} = 0.23$$

The poor performance of this algorithm is due to the data associated on the edges of each cluster that can affect the variance of several clusters similarly, and the algorithm associate the new data to the wrong cluster.

SVM

Figure 48:
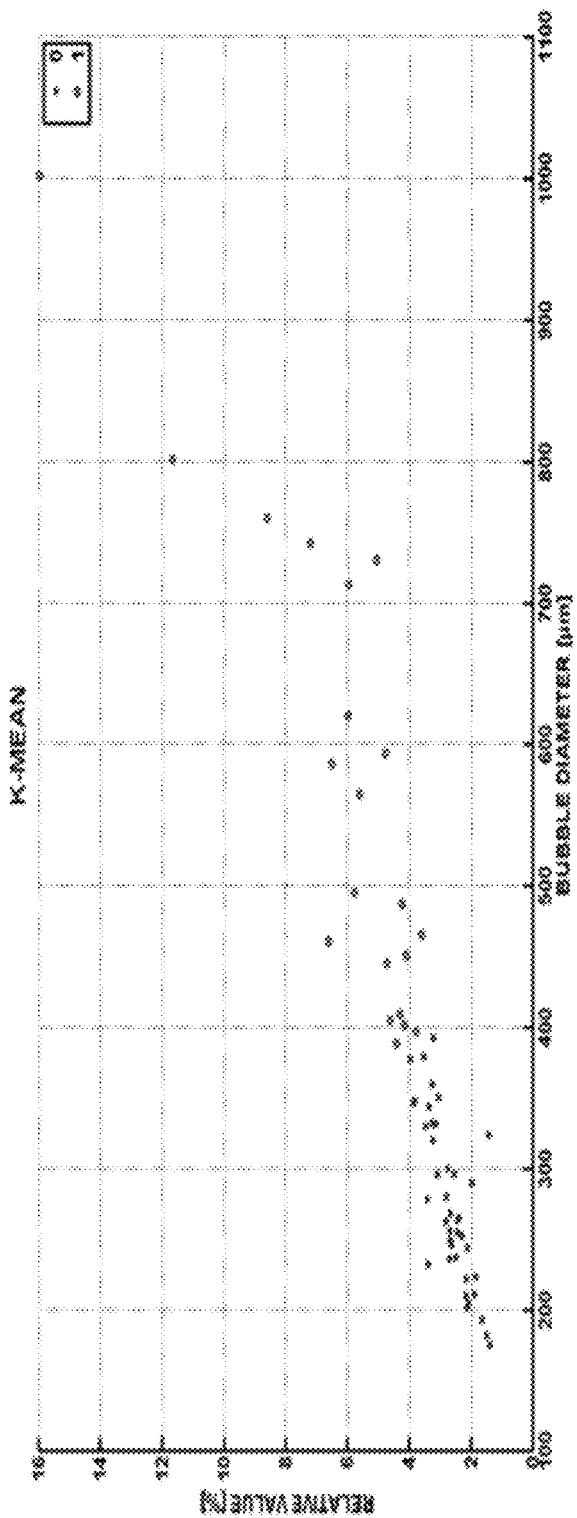
FIG. 48 shows the prediction of the K-mean algorithm response with 63 data samples.

The SVM algorithm detected four classes of 5 (FIG. 48). This algorithm depends on the stage of training and not detecting class 5 may be due to the lack of observations to find optimal separability between classes. Table 8 shows the results from the SVM prediction to 1 feature and 5 classes.

TABLE 8

|  |  | Real | | | | | |
|---|---|---|---|---|---|---|---|
|  |  | 0 | 1 | 2 | 3 | 4 | Total |
| SVM | 0 | 12 | 7 | 0 | 0 | 0 | 19 |
|  | 1 | 1 | 24 | 1 | 0 | 0 | 26 |
|  | 2 | 0 | 0 | 31 | 0 | 0 | 31 |
|  | 3 | 0 | 0 | 1 | 19 | 4 | 24 |
|  | 4 | 0 | 0 | 0 | 0 | 0 | 0 |
|  | Total | 13 | 31 | 33 | 19 | 4 | 100 |

The accuracy and error in bubble detection are:

$$\text{Accuracy} = \frac{86}{100} = 0.86$$

$$\text{Error} = \frac{14}{100} = 0.14$$

The performance dropped by 3% in accuracy with respect to detection of two classes. This is good since it could further increase the number of intervals, and the accuracy lost is under 5%, considering that an accuracy lost larger than 5% is relevant.

NN

Figure 49:
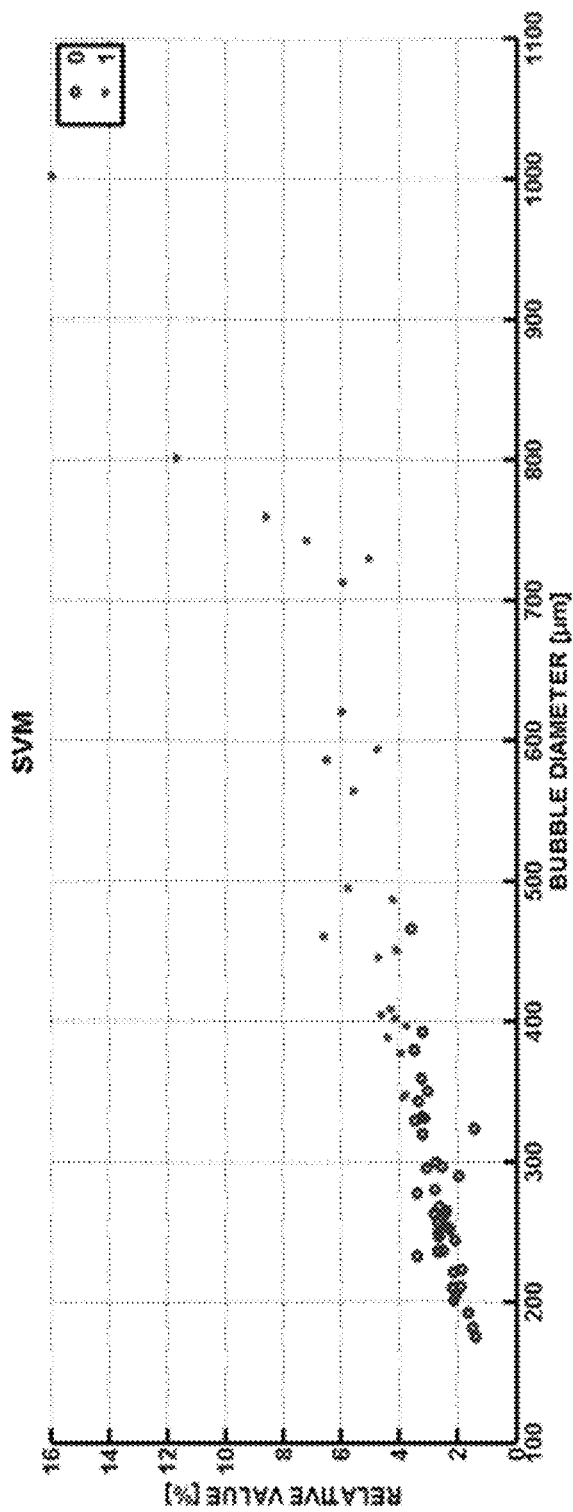
FIG. 49 shows the results of the SVM algorithm with 63 data samples.

The procedure was similar to SVM training, i.e. training was used for the current signal only. FIG. 49 shows the prediction of the NN algorithm with 100 data samples corresponding to the PZT were being actuated when the bubbles were at its center. Table 9 shows the results from the NN prediction to 1 feature and 5 classes.

TABLE 9

|    |   | Real |    |    |    |   | Total |
|----|---|------|----|----|----|---|-------|
|    |   | 0    | 1  | 2  | 3  | 4 |       |
| NN | 0 | 10   | 1  | 0  | 0  | 0 | 11    |
|    | 1 | 3    | 29 | 0  | 0  | 0 | 32    |
|    | 2 | 0    | 1  | 33 | 5  | 0 | 39    |
|    | 3 | 0    | 0  | 0  | 14 | 4 | 18    |
|    | 4 | 0    | 0  | 0  | 0  | 0 | 0     |
| Total |   | 13 | 31 | 33 | 19 | 4 | 100   |

The accuracy and error in bubble detection are:

$$\text{Accuracy} = \frac{86}{100} = 0.86$$

$$\text{Error} = \frac{14}{100} = 0.14$$

The NN algorithm accuracy lost 5% due to increase the number of classes.

Bubble Detection with 3 Feature for 2 Classes

The input data used for the detection algorithms were: current signal from the PZT ring signal, voltage signal from the MP1 (0 cm) and voltage signal from the MP2 (2 cm). This set of inputs was selected because, as mentioned previously, these three devices are common to 63 data samples. On the other hand, only half the data would have been used for testing.

K-Mean

Figure 50:
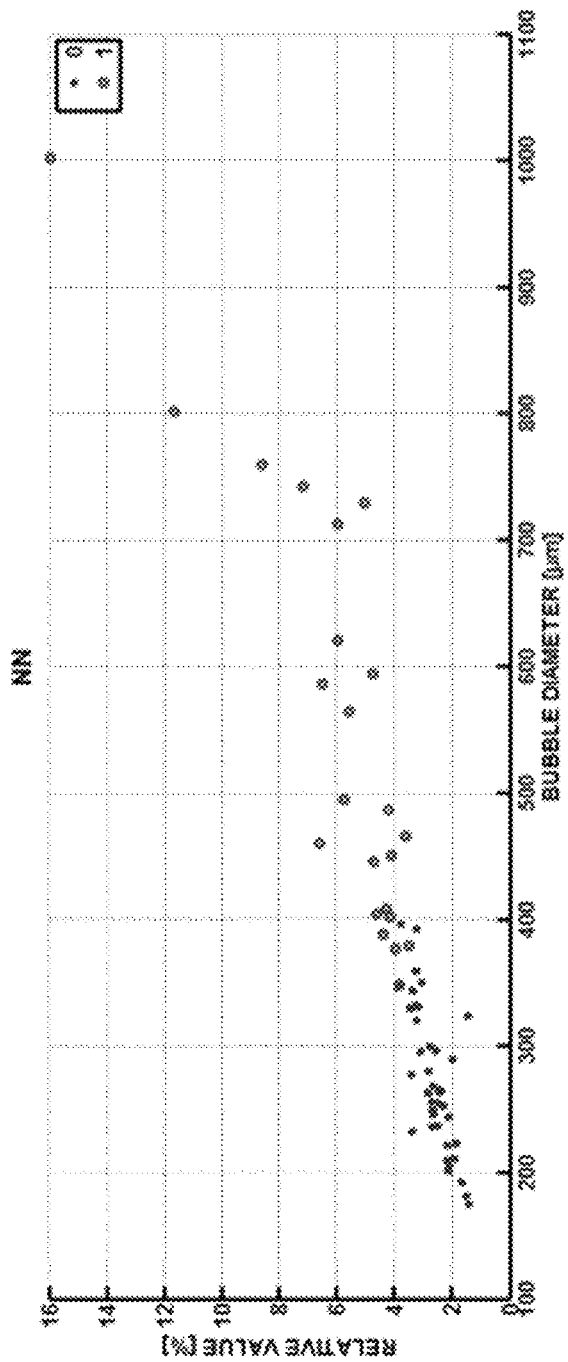
FIG. 50 shows the response of the NN algorithm with 63 data samples.

"0" represents bubbles predicted to have a size smaller than 400 μm and "1" represents bubbles bigger than 400 The first test is to detect bubbles again for 2 classes. FIG. 50 shows the curve relative value against bubble diameter. The response of the algorithm is summarized in terms of the grouping of the cluster "0" and the cluster "1". Table 10 shows the results from the K-mean prediction to 3 features and 2 classes.

TABLE 10

|        |       | Real |    |       |
|--------|-------|------|----|-------|
|        |       | 0    | 1  | Total |
| K-mean | 0     | 39   | 3  | 42    |
|        | 1     | 0    | 21 | 21    |
|        | Total | 39   | 24 | 63    |

The accuracy and error in bubble detection are 0.95 and 0.05, respectively. It should be noted that the number of data decreased from 100 samples to 63 samples. Also, signals from the microphones were also implemented. Thus, prediction accuracy improved by 10%.

SVM

Figure 51:
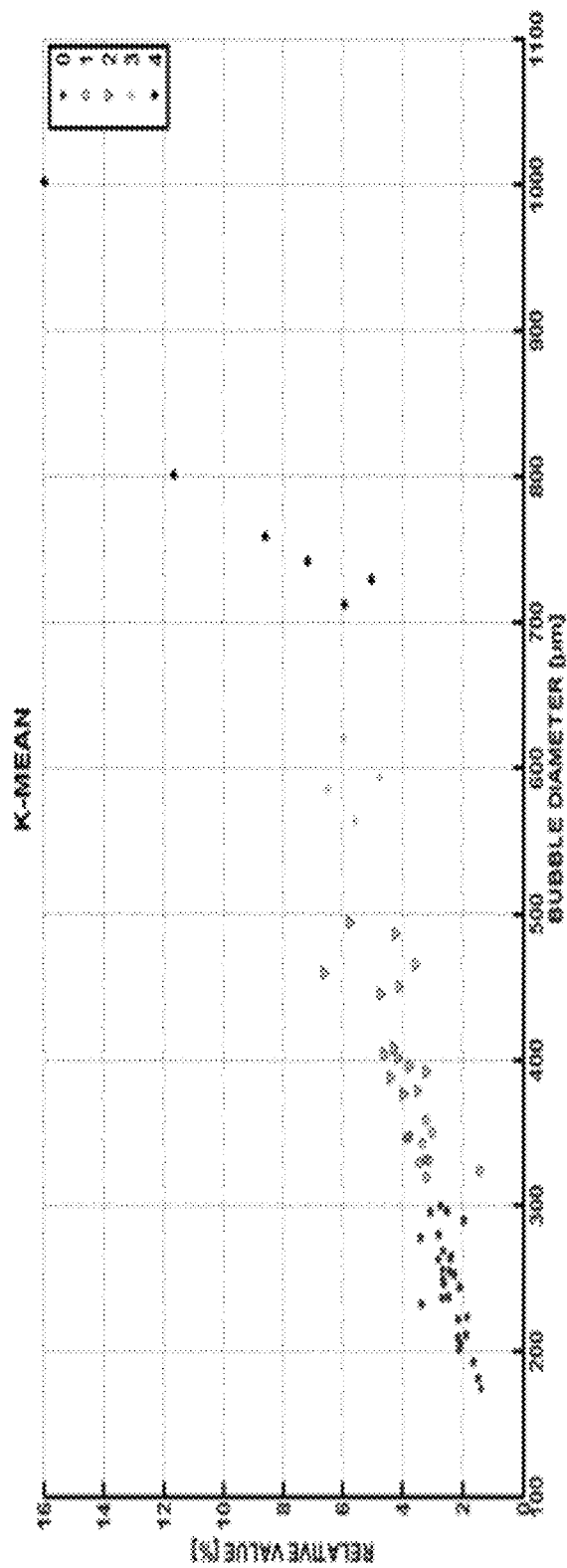
FIG. 51 shows the prediction of the K-mean algorithm response with 63 data samples to 3 features and 5 classes.

This algorithm training was conducted as: "0" represents bubbles predicted to have a size smaller than 400 μm and "1" represents bubbles bigger than 400 μm (FIG. 51). Table 11 shows the results from the SVM prediction to 3 features and 2 classes.

TABLE 11

|     |       | Real |    |       |
|-----|-------|------|----|-------|
|     |       | 0    | 1  | Total |
| SVM | 0     | 37   | 3  | 40    |
|     | 1     | 2    | 21 | 23    |
|     | Total | 39   | 24 | 63    |

The accuracy and error in bubble detection are 0.92 and 0.08, respectively. The SVM algorithm as K-mean algorithm, also improved with respect to the detection of two classes only using the current signal. For this SVM algorithm, the accuracy improved over the previous result by 3%.

NN

Figure 52:
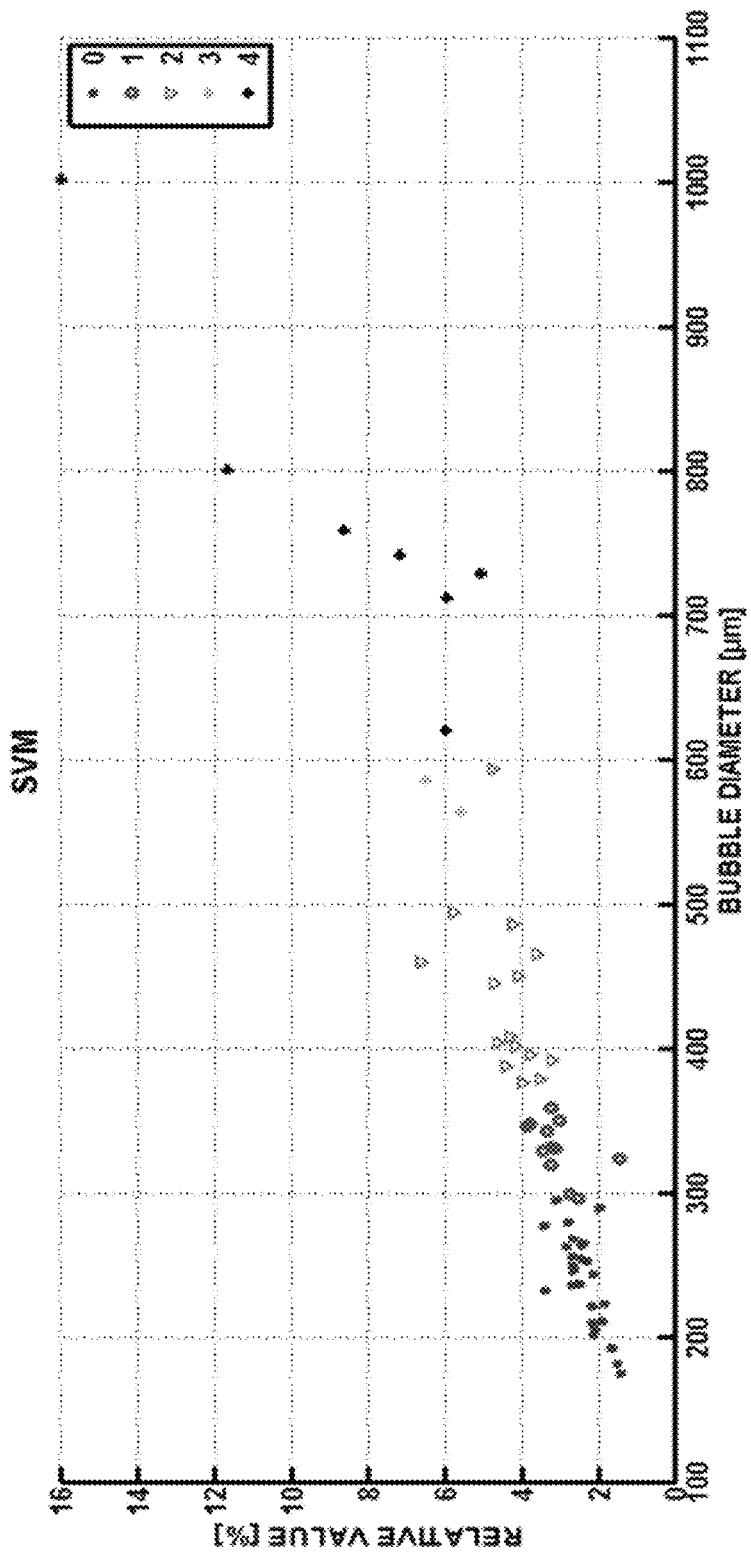
FIG. 52 shows the prediction of the SVM algorithm response with 63 data samples to 3 features and 5 classes.

The NN algorithm as SVM algorithm was trained with: "0" represents bubbles predicted to have a size smaller than 400 μm and "1" represents bubbles bigger than 400 μm (FIG. 52). Table 12 show the results from the NN prediction to 3 feature and 2 classes.

TABLE 12

|    |       | Real |    |       |
|----|-------|------|----|-------|
|    |       | 0    | 1  | Total |
| NN | 0     | 38   | 1  | 39    |
|    | 1     | 2    | 22 | 24    |
|    | Total | 40   | 23 | 63    |

The accuracy and error in bubble detection are 0.95 and 0.05, respectively. The NN algorithm improved its accuracy by 4% using microphones information with respect to the detection of bubbles using only current information from the PZT ring.

Bubble Detection with 3 Feature for 5 Classes

For this step the curve relative value against bubble diameter was divided into 5 classes similarly as previously explained. Table 13 shows the labels used.

TABLE 13

| Label | Interval                |
|-------|-------------------------|
| 0     | bubbles smaller than 290 μm |
| 1     | 290 μm and 360 μm       |
| 2     | 360 μm and 490 μm       |
| 3     | 490 μm and 620 μm       |
| 4     | bubbles bigger than 620 μm |

K-Mean

Figure 53:
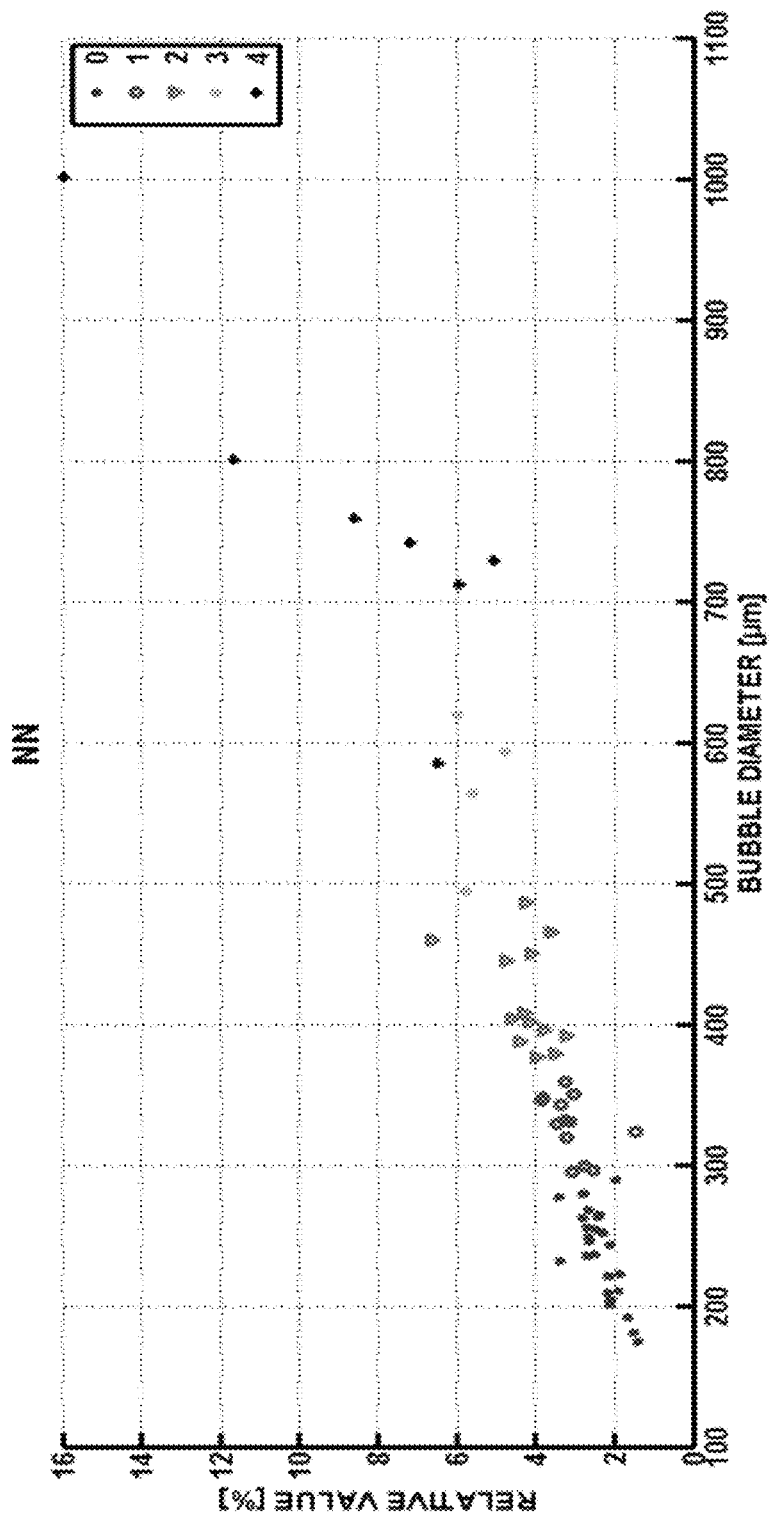
FIG. 53 shows the prediction of the NN algorithm response with 63 data samples to 3 features and 5 classes.

The prediction of the K-mean algorithm was used when 63 data samples corresponding to the PZT being actuated when the bubbles were at its center was used. Table 13 shows the intervals for the detection of the bubbles obtained from the K-mean classification to 3 features and 5 classes. FIG. 53 shows the prediction of the K-mean algorithm response with 63 data samples to 3 features and 5 classes. Table 14 shows the results from the K-mean prediction to 3 feature and 5 classes.

TABLE 14

| | | \multicolumn{5}{c|}{Real} | |
|---|---|---|---|---|---|---|---|
| | | 0 | 1 | 2 | 3 | 4 | TOTAL |
| KMEAN | 0 | 13 | 0 | 0 | 0 | 1 | 14 |
| | 1 | 0 | 6 | 0 | 0 | 0 | 6 |
| | 2 | 0 | 0 | 10 | 0 | 0 | 10 |
| | 3 | 0 | 0 | 3 | 26 | 0 | 29 |
| | 4 | 0 | 0 | 0 | 0 | 4 | 4 |
| | Total | 13 | 6 | 13 | 26 | 5 | 63 |

The accuracy and error in bubble detection are 0.94 and 0.06, respectively. The loss of precision was 1% compared to the detection of bubbles for 2 classes previously shown. It is due to the problem of edges in the detection mentioned above.

SVM

Figure 54:
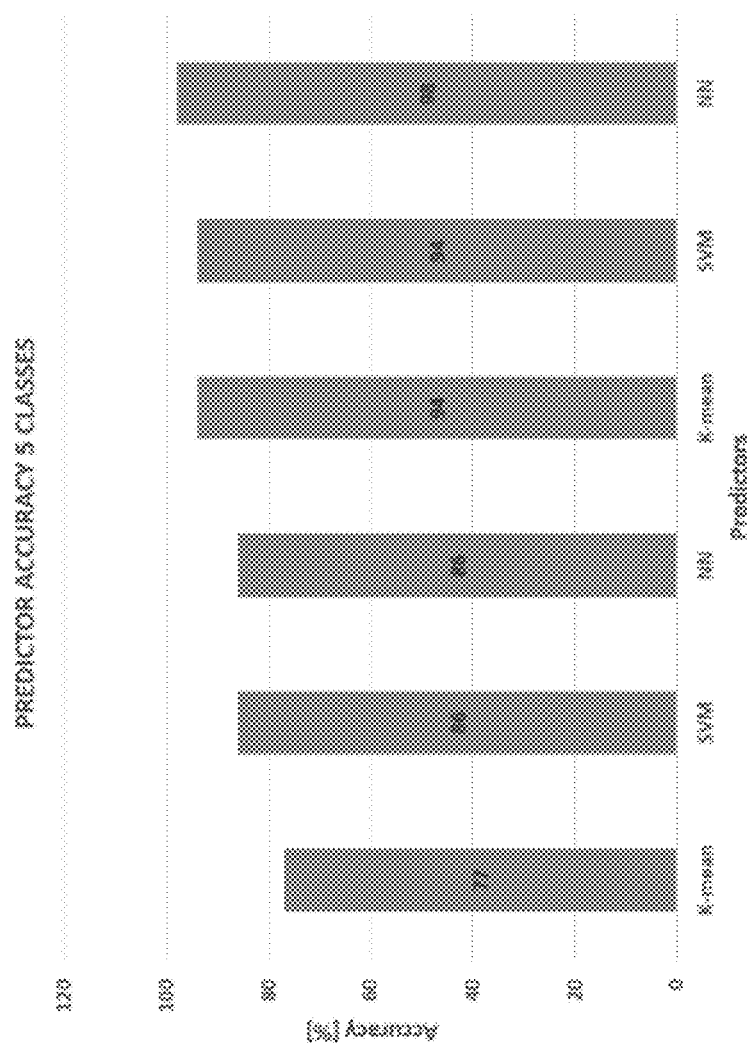
FIG. 54 shows the predictor accuracy to 5 classes.

The detection of the SVM algorithm when 63 data samples corresponding to the PZT being actuated when the bubbles were at its center was used. Table 13 indicates the intervals in which predictor SVM algorithm detects bubbles. FIG. 54 shows the prediction of the SVM algorithm response with 63 data samples to 3 features and 5 classes. Table 15 shows the results from the SVM prediction to 3 feature and 5 classes.

TABLE 15

| | | \multicolumn{5}{c|}{Real} | |
|---|---|---|---|---|---|---|---|
| | | 0 | 1 | 2 | 3 | 4 | Total |
| SVM | 0 | 12 | 0 | 0 | 0 | 0 | 13 |
| | 1 | 0 | 6 | 0 | 0 | 0 | 6 |
| | 2 | 0 | 0 | 12 | 1 | 0 | 13 |
| | 3 | 0 | 0 | 0 | 26 | 0 | 26 |
| | 4 | 2 | 1 | 0 | 0 | 2 | 5 |
| | Total | 15 | 7 | 12 | 27 | 2 | 63 |

The accuracy and error in bubble detection are 0.94 and 0.06, respectively. The accuracy of the SVM algorithm improved by 2% with respect to the detection of two classes using 3 features. This means that observations from the microphones are a significant contribution to this detection algorithm.

NN

Figure 55:
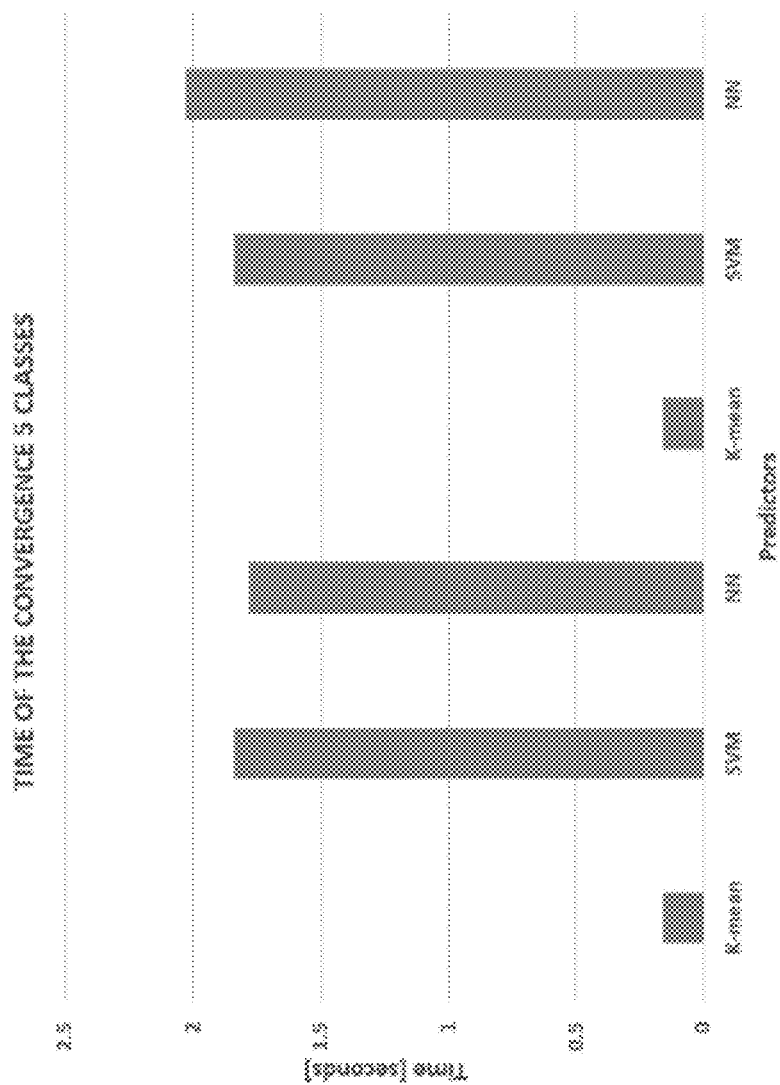
FIG. 55 indicates the time of convergence to predictors for 5 classes.

The NN algorithm as SVM algorithm was trained with data from Table 13. FIG. 55 shows the prediction of the NN algorithm response with 63 data samples to 3 features and 5 classes. Table 16 shows the results from the NN prediction to 3 features and 5 classes.

TABLE 16

| | | \multicolumn{5}{c|}{Real} | |
|---|---|---|---|---|---|---|---|
| | | 0 | 1 | 2 | 3 | 4 | Total |
| NN | 0 | 13 | 0 | 0 | 0 | 0 | 13 |
| | 1 | 0 | 6 | 0 | 0 | 0 | 6 |
| | 2 | 0 | 0 | 13 | 0 | 0 | 13 |
| | 3 | 0 | 0 | 0 | 26 | 0 | 26 |
| | 4 | 0 | 1 | 0 | 0 | 4 | 5 |
| | Total | 13 | 7 | 13 | 26 | 4 | 63 |

The accuracy and error in bubble detection are 0.98 and 0.02, respectively. The NN algorithm improved the accuracy by 3% compared to the detection of two classes using 3 features. The NN algorithm is more accurate in comparison to SVM and K-mean.

Overview and Rate of Convergence

The algorithm analysis previous explained, were performed based on the accuracy and error in the bubbles detection. Accordingly, the iterations and rate of convergence are detected. For the comparison, a laptop with a processor "Intel® Core™ i7-2670QM CPU @ 2.20 GHz" was used. The priority configuration for MATLAB software was changed to real time in the computer. The "TALKLIST" command was called to determine the processes of the computer. From the above, convergence time for each algorithm was defined in the following Table 17:

TABLE 17

| Algorithm | Features | Classes | Iterations | Time of convergence |
|---|---|---|---|---|
| K-mean | 1 | 2 | 4 | 0.14 |
| SVM | 1 | 2 | 14 | 1.20 |
| NN | 1 | 2 | 22 | 1.76 |
| K-mean | 1 | 5 | 5 | 0.16 |
| SVM | 1 | 5 | 29 | 1.84 |
| NN | 1 | 5 | 19 | 1.78 |
| K-mean | 3 | 2 | 8 | 0.15 |
| SVM | 3 | 2 | 21 | 1.34 |
| NN | 3 | 2 | 34 | 1.83 |
| K-mean | 3 | 5 | 7 | 0.16 |
| SVM | 3 | 5 | 27 | 1.84 |
| NN | 3 | 5 | 133 | 2.03 |

From the above table, the K-mean algorithm with STD predictor is the faster in convergence because their operations are simple, i.e. getting Euclidean distances and standard deviations. The SVM and NN algorithms methods use decompose matrices to solve optimization problems and this generates more computational resource causing delay.

Results and Analysis

Table 18 below associates previous results in accuracy, iterations and convergence time for each algorithm in the respective condition as: characteristics and classes.

TABLE 18

| Algorithm | Samples | Features | Classes | Iterations | Time Convergence (s) | Accuracy |
|---|---|---|---|---|---|---|
| K-mean | 100 | 1 | 2 | 4 | 0.14 | 84 |
| SVM | 100 | 1 | 2 | 14 | 1.20 | 89 |
| NN | 100 | 1 | 2 | 22 | 1.76 | 91 |
| K-mean | 100 | 1 | 5 | 5 | 0.16 | 77 |
| SVM | 100 | 1 | 5 | 29 | 1.84 | 86 |
| NN | 100 | 1 | 5 | 19 | 1.78 | 86 |
| K-mean | 63 | 3 | 2 | 8 | 0.15 | 95 |
| SVM | 63 | 3 | 2 | 21 | 1.34 | 92 |
| NN | 63 | 3 | 2 | 34 | 1.83 | 95 |
| K-mean | 63 | 3 | 5 | 7 | 0.16 | 94 |
| SVM | 63 | 3 | 5 | 27 | 1.84 | 94 |
| NN | 63 | 3 | 5 | 133 | 2.03 | 98 |

Figure 34:
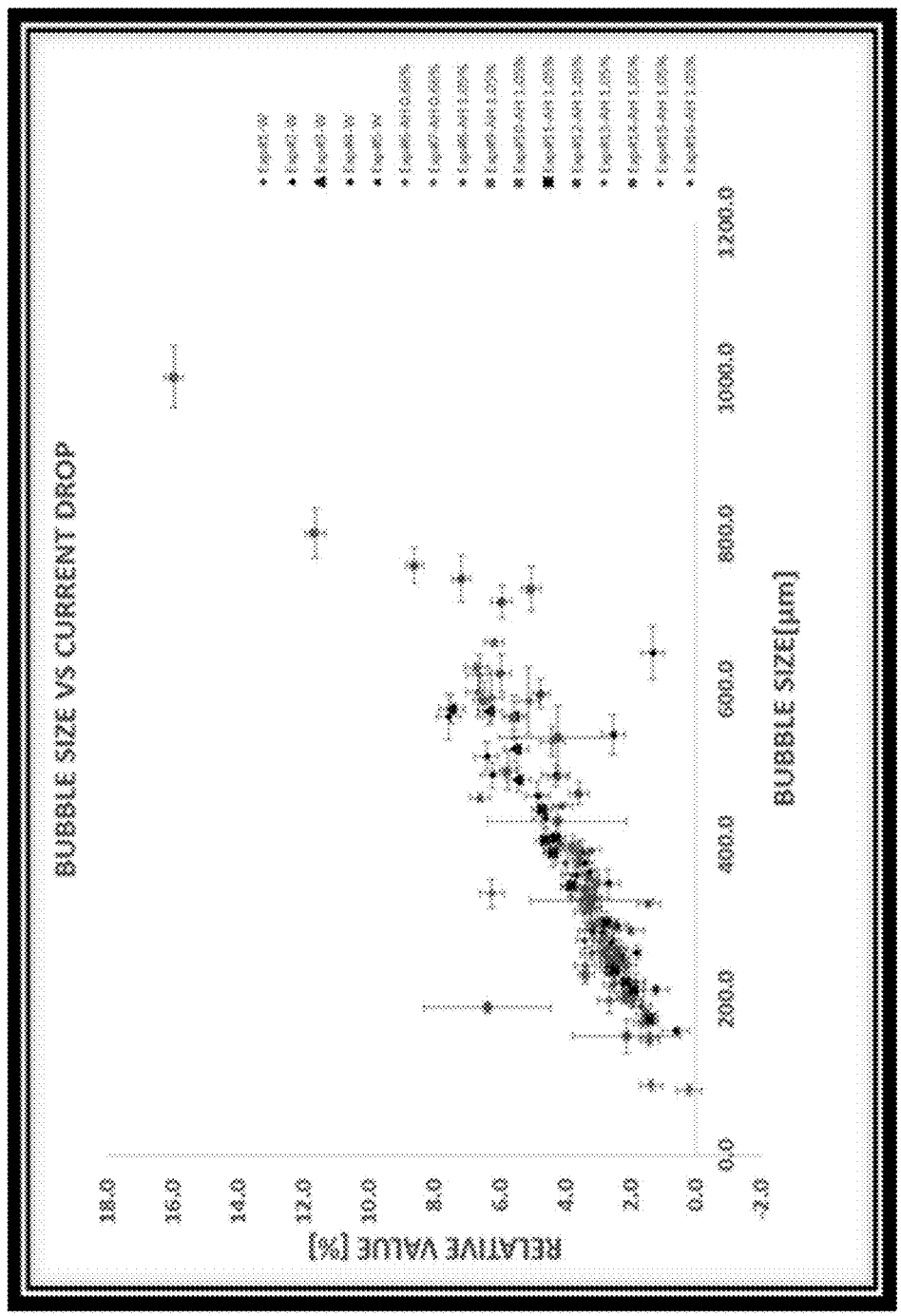
FIG. 34 shows the relationship between relative values and bubble size diameter from bubbles crossing the PZT ring.
Figure 57:
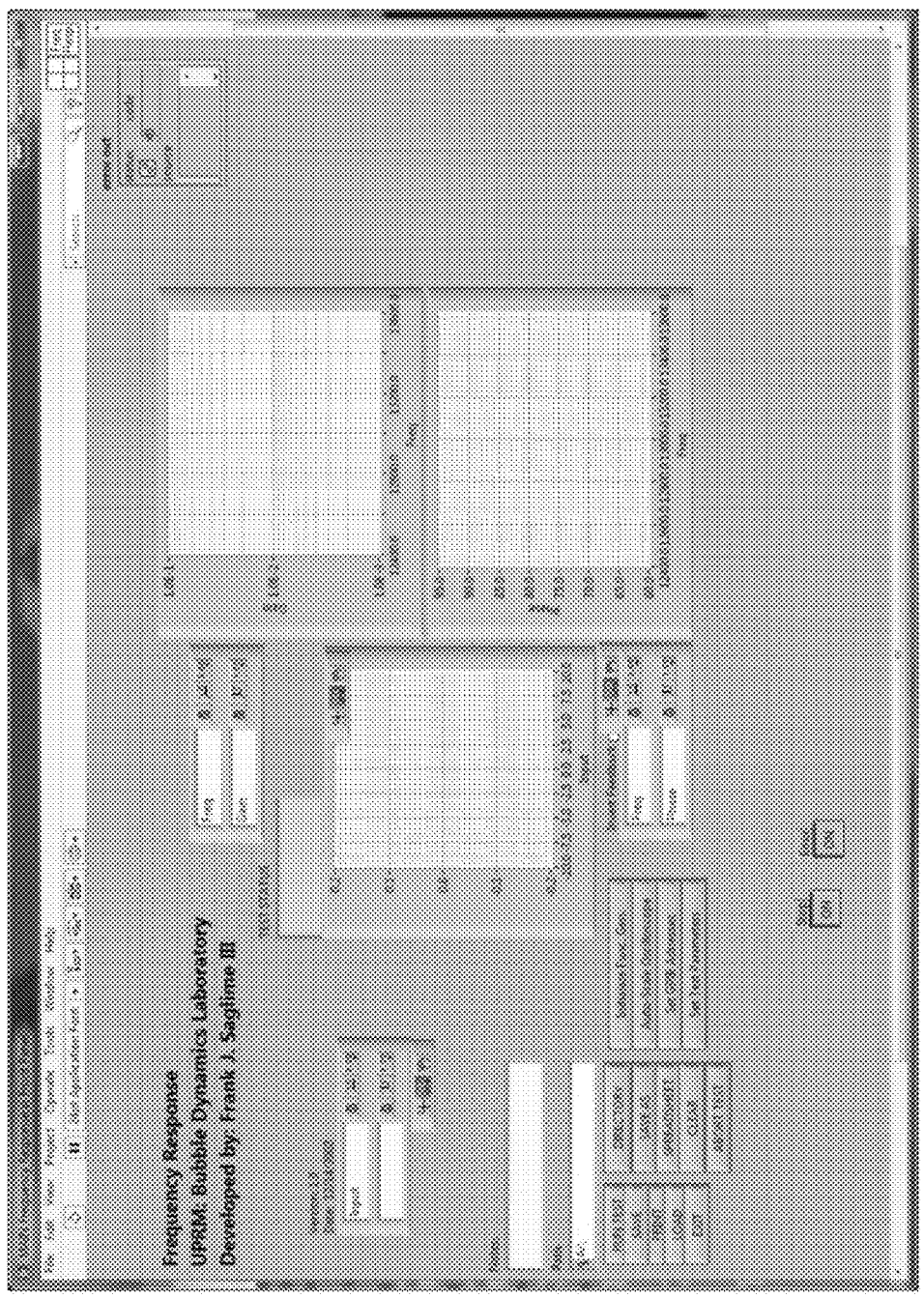
FIG. 57 shows a GUI implementing the Frequency response algorithm, according to the present invention.

Note that the addition of new features to all predictor's algorithms improves accuracy, as better illustrated by FIG. 54 which demonstrates the increase the number of the classes and the features and is possible to estimate the curve obtained in FIG. 34. This is relevant because with the application of the classifiers it is possible to detect the bubbles with an accuracy over 90%. Convergence times of the algorithms show which supervised algorithms have more time to converge due to the simplicity in calculating geometric distances, compared to solving optimization problems. FIG. 57 indicates the time of convergence to predictors for 5 classes. Accordingly, the best algorithm for accurate bubble detection would be the neural network, whereas the best algorithm for faster bubbles detection would be K-mean with STD predictor.

When considering the disadvantages, it is important to note that the targets election for the training stage was made by the K-mean. This favors the high precision of K-mean and STD predictor. Another important point is the number of iterations when the features and classes are increased in neural networks. On a computer with the technical features that were used, it is not relevant; but when the implementation is in a microcontroller, FPGA or DSP hardware device the convergence time would increase considerably.

Results in the bubbles detection at 1 cm from the edge bottom of the PZT ring were previously explained above. Assuming the sensor works in a pulsated manner, and bubbles are present in the blood stream, then if the bubbles moving along the artery are further away than 2 cm from the PZT the system will not detect them. If the bubbles are between 0-1 cm from the PZT the system will detect them.

The sensor according to the present invention is able to distinguish between a small bubble that might be at the center of the PZT when the PZT is actuated, from a big bubble that is at 1 cm from the PZT when the PZT is actuated. This is confirmed by the results shown in Table 19, Table 20 and Table 21, below.

Table 19 shows a confusion matrix for the K-mean algorithm with 4 features for the data points corresponding to the PZT actuated when the bubbles were at the center of the PZT and for bubbles that were located at 1 cm away from the PZT when it was actuated.

TABLE 19

|         |       | Real |    |       |
|---------|-------|------|----|-------|
|         |       | 0    | 1  | Total |
| K-mean  | 0     | 33   | 3  | 36    |
|         | 1     | 2    | 25 | 27    |
|         | Total | 35   | 28 | 63    |

The accuracy and error of the K-mean and STD predictor algorithm are:

$$\text{Accuracy} = \frac{58}{63} = 0.92$$

$$\text{Error} = \frac{5}{63} = 0.08$$

Table 20 shows a confusion matrix for the SVM algorithm with 4 features for the data points corresponding to the PZT actuated when the bubbles were at the center of the PZT and for bubbles that were located at 1 cm away from the PZT when it was actuated.

TABLE 20

|     |       | Real |    |       |
|-----|-------|------|----|-------|
|     |       | 0    | 1  | Total |
| SVM | 0     | 31   | 10 | 41    |
|     | 1     | 4    | 18 | 22    |
|     | Total | 35   | 28 | 63    |

The accuracy and error of the SVM predictor algorithm are:

$$\text{Accuracy} = \frac{49}{63} = 0.78$$

$$\text{Error} = \frac{14}{63} = 0.22$$

Table 21 shows a confusion matrix for the neural network algorithm with 4 features for the data points corresponding to the PZT actuated when the bubbles were at the center of the PZT and for bubbles that were located at 1 cm away from the PZT when it was actuated.

TABLE 21

|    |       | Real |    |       |
|----|-------|------|----|-------|
|    |       | 0    | 1  | Total |
| NN | 0     | 33   | 1  | 34    |
|    | 1     | 2    | 27 | 29    |
|    | Total | 35   | 28 | 63    |

The accuracy and error of the NN predictor algorithm are:

$$\text{Accuracy} = \frac{60}{63} = 0.95$$

$$\text{Error} = \frac{3}{63} = 0.05$$

The algorithms developed and implemented will be described in conjunction with the accompanying Figures.

Algorithm Setup to Bubble Generating System

Figure 56:
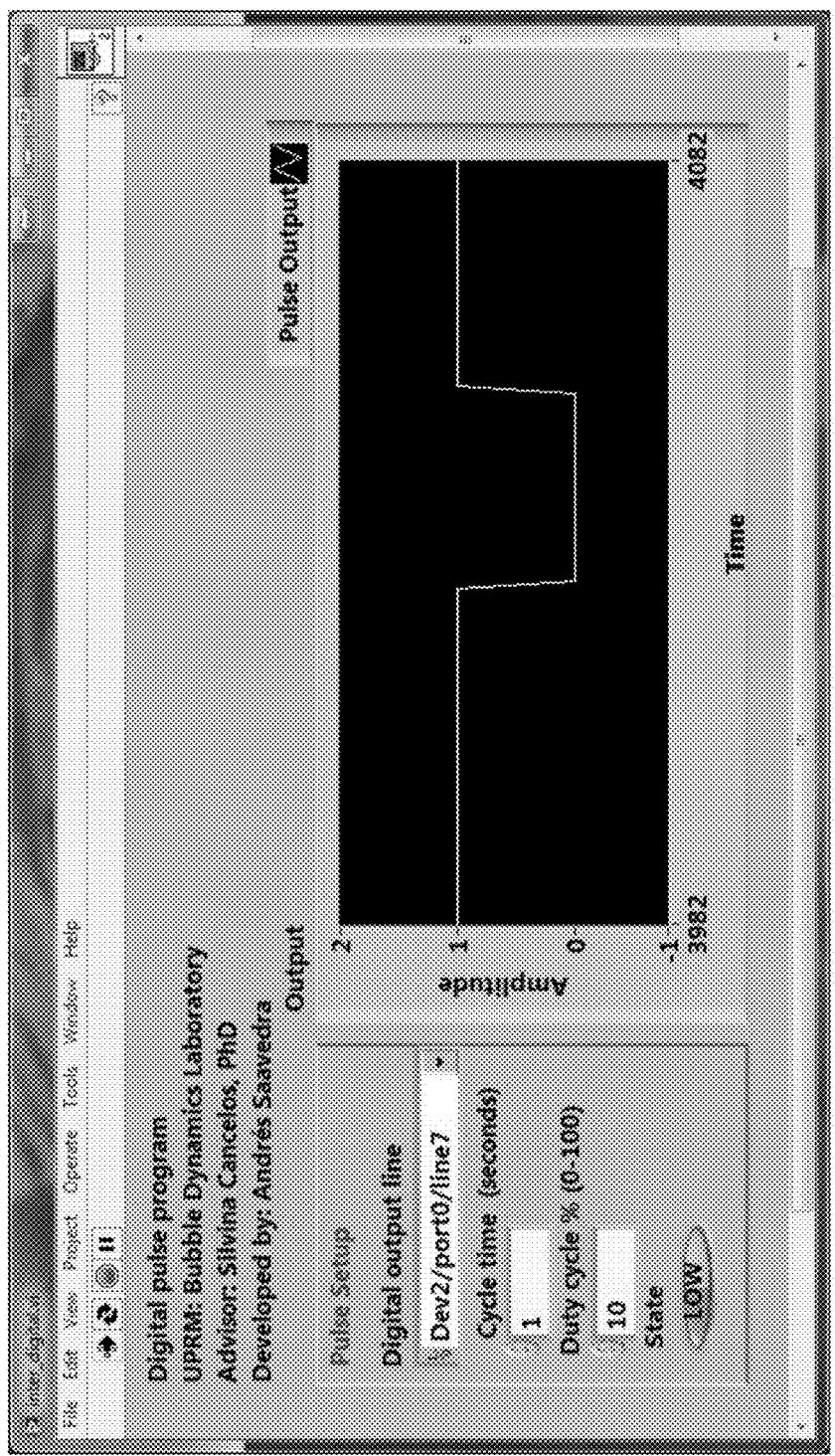
FIG. 56 illustrates a GUI for a Pulse with modulator program in Labview.
Figure 58:
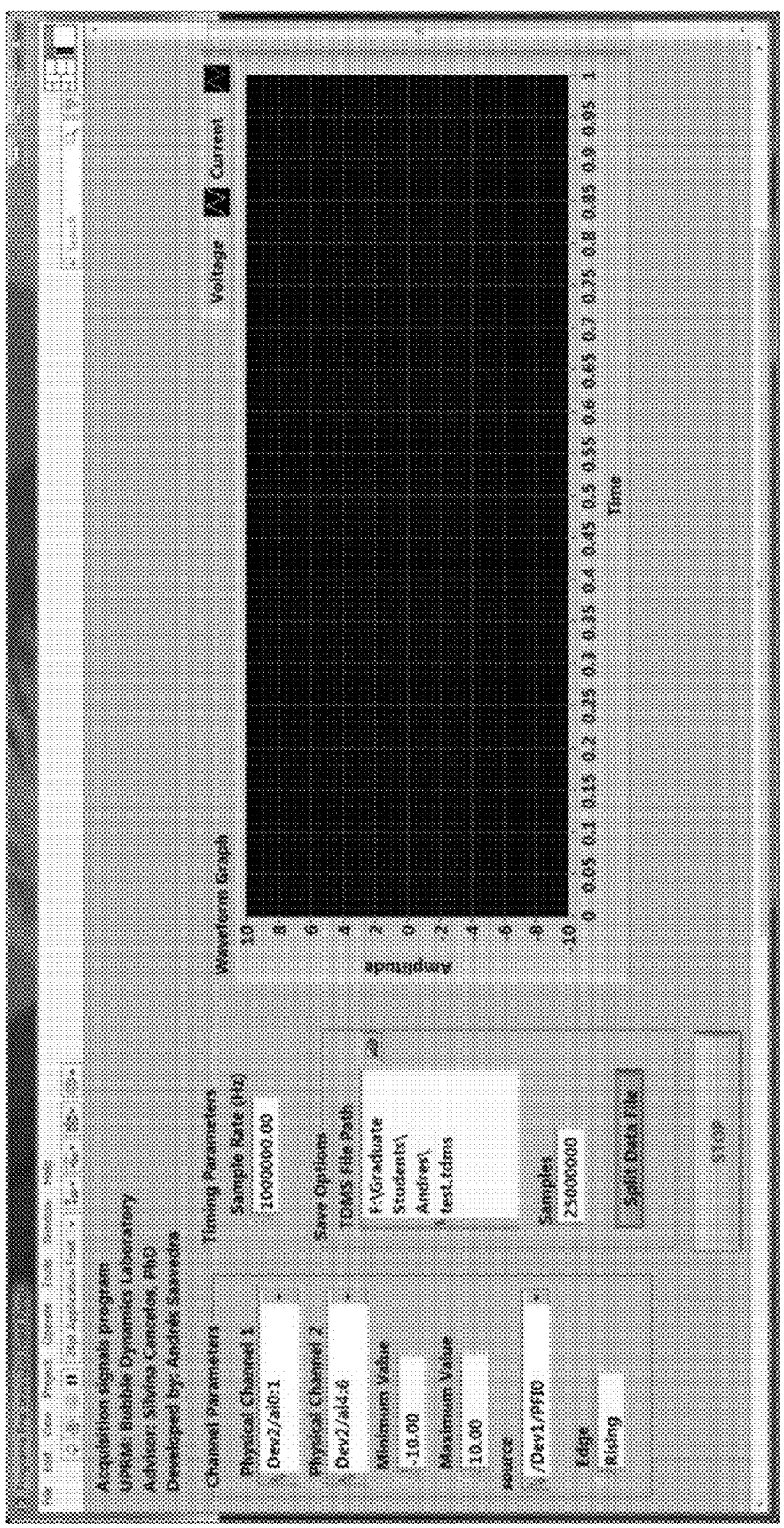
FIG. 58 shows a GUI implementing the data acquisition program, according to the present invention.

The program developed determines the pulse time, the duty cycle and the state as shown in FIG. 56, wherein the duty cycle is given by the relationship:

$$\text{Duty cycle} = \frac{\tau}{T} \quad (47)$$

where "τ" is the time, and the period of the signal is "T" (pulse time in our case). The state indicated when working with "τ" in low or high. Because the NI6356 card always broadcasts a high pulse on digital port, this condition maintains activation of the electro valve at all times, so the state will work on low pulse (actuates the solenoid when the pulse goes down to a 10% duty cycle as shown in FIG. 58).

Algorithm Setup to Frequency Response

The algorithm to detect the frequency response is implemented by the GUI shown in FIG. 57. For the first step is necessary select the GPM address. Each device, like the waveform generator and the oscilloscope, have addresses, therefore must be selected indicating the device. In our case, the oscilloscope address is 7 and the waveform generator is 11. The next step is to select "set test parameters", here the number of points, the range and breadth of the sweep frequency are chosen.

Algorithm Setup to Acquisition Signals

The GUI of the Labview program used with the data acquisition card is shown in FIG. 58. Details of the configuration of the program are shown in Table 22 below.

| REGIONS | SPECIFICATIONS |
|---|---|
| CHANNEL PARAMETERS | Establishes the channel parameters such as the amplitude level to be received in each channel. |
| TIMMING PARAMETERS | Specifies the value for the sample rate, for example 1.0 MHz |
| SAVE OPTIONS | Select options for saving data, such as location and size of each file. The bottom "Split data file", when clicked, generates the partition size that was set. |

Figure 59:
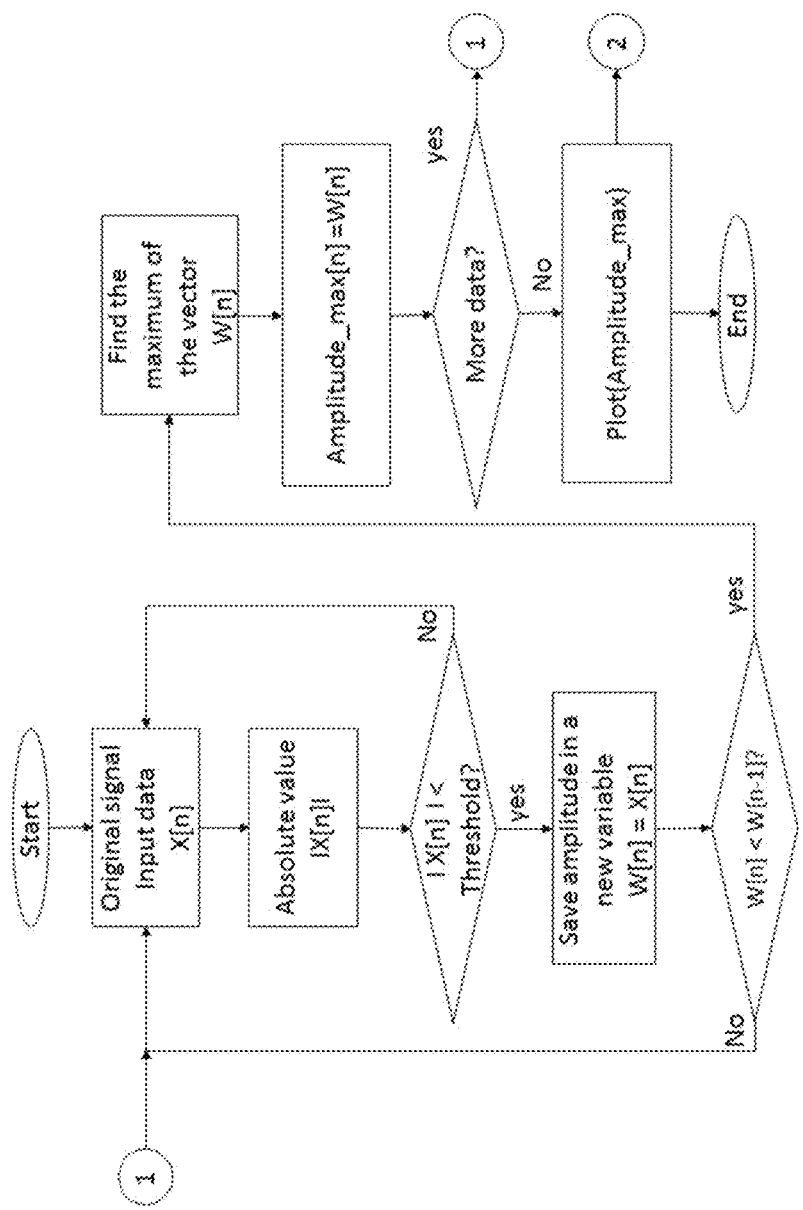
FIG. 59 a block diagram for amplitude peaks detection, according to the present invention.
Figure 60:
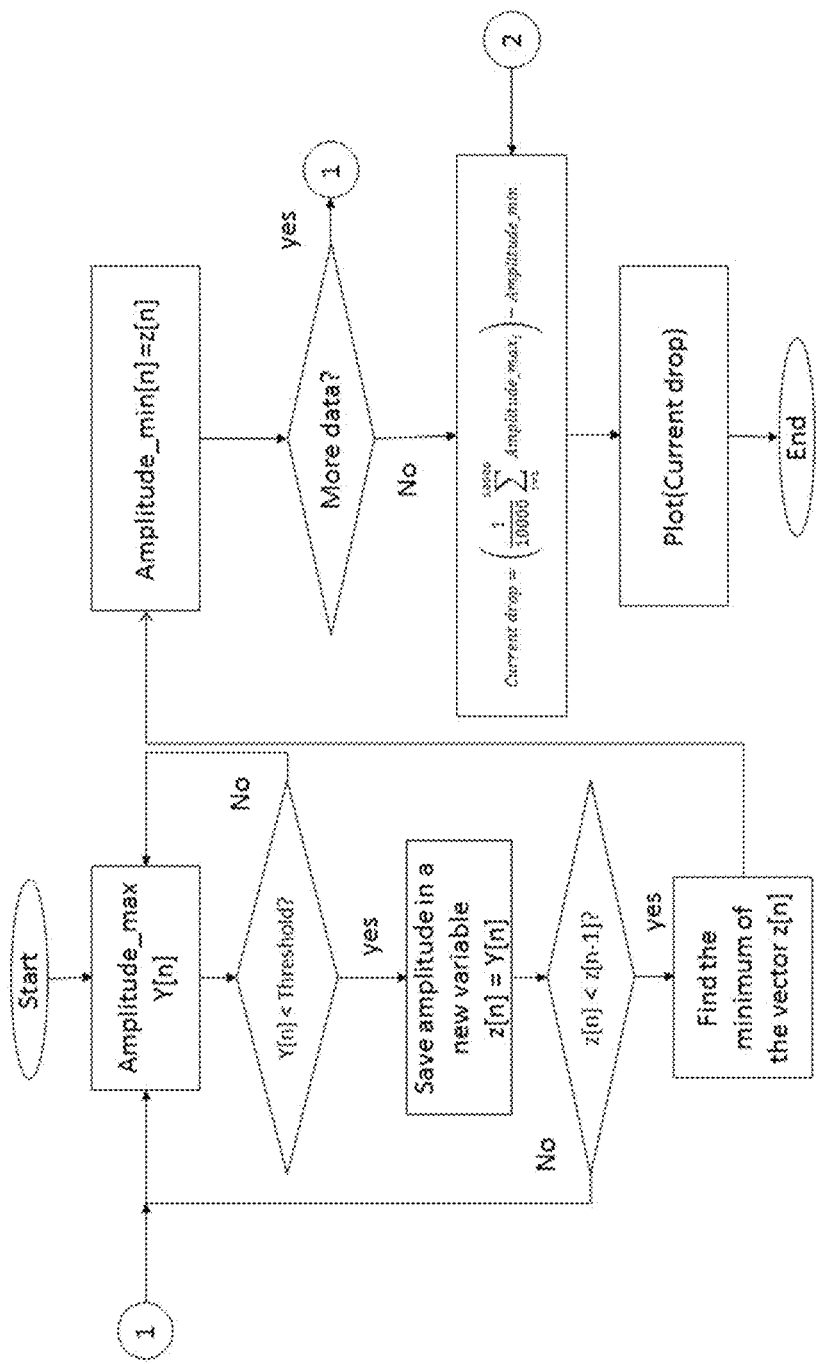
FIG. 60 shows a block diagram for current drop detection, according to the present invention.
Figure 61:
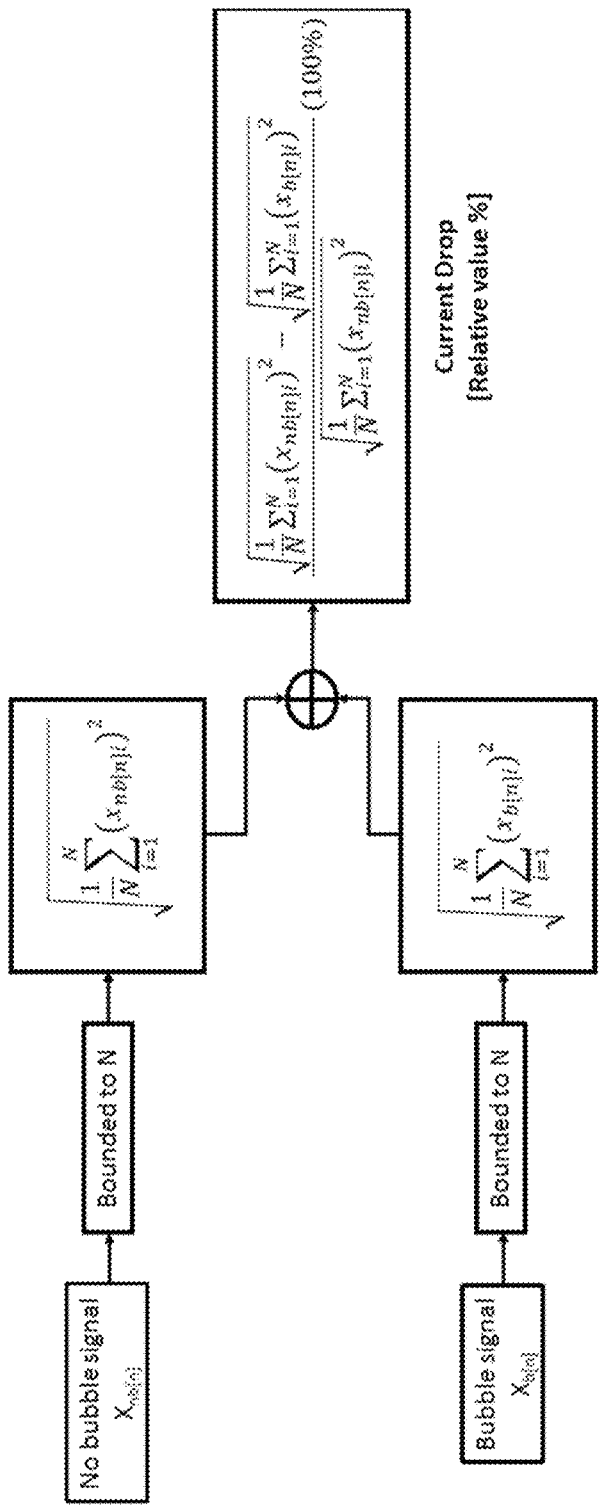
FIG. 61 shows the algorithm to detect Current drop in relative value using "method 2", according to the present invention.

Algorithms to Current Drop Detecting
Method 1:

The algorithm shown in FIG. 59 can detect the maximum amplitude of each semi cycle. Also, the algorithm developed to find the current drop is shown in FIG. 60.
Method 2:

FIG. 61 shows the algorithm implemented to detect the differential between reference signal "$x_{nb[n]}$" and bubble signal "$x_{b[n]}$".

K-Mean Algorithm and STD Predictor

The following code was developed to implement the K-mean algorithm and STD predictor as previously explained according to the present invention.

```
% K-mean y STD predictor
clc
clear all
close all
%------------------------------------------------------------------
% Data with the extracted characteristics
%------------------------------------------------------------------
A=xlsread('C:\Users\Andres Saavedra\Documents\MATLAB\work\Thesis\Algoritmos finales\Data entrenamiento\Data_input_2_features.xlsx');
Bubble_size1=A(:,4);% column with bubble sizes in micrometers
Curren_drop=A(:,3);% column with the current drop in mili-amperes
MP1=A(:,5);
MP2=A(:,6);
%------------------------------------------------------------------
% Classification
%------------------------------------------------------------------
tic % Start of execution timing count
% MP3=A(:,7);
% X=[Bubble_size1 Curren_drop];% 2 features
X=[Bubble_size1 Curren_drop MP1 MP2];% 4 features
Grupos=5;% Quantity of classes
rng('default') % For reproducibility
opts=statset('Display','final');tic
[idx,ctrs]=kmeans(X,Grupos,'Distance','city','Replicates',15,'Options',opts);
toc % End of execution timing count
plot(X(idx==1,1),X(idx==1,2),'r.','MarkerSize',12)
hold on
plot(X(idx==2,1),X(idx==2,2),'b.','MarkerSize',12)
plot(ctrs(:,1),ctrs(:,2),'kx','MarkerSize',12,'LineWidth',2)
plot(ctrs(:,1),ctrs(:,2),'ko','MarkerSize',12,'LineWidth',2)
legend('Cluster 1','Cluster 2','Centroids','Location','NW')
hold off
Resultado=[X,idx];
toc
gscatter(Bubble_size,X(:,2),idx,'br','xo')%2 classes color, symbol
%    gscatter(Bubble_size,X(:,2),idx,'brkgm','xov*+')%5 classes
%    xlswrite('kmean_prediccion_4features_2clases',Resultado);%
% xlswrite('kmean_clasificacion_4features_2clases',Resultado);%
%------------------------------------------------------------------
% Initialize STD predictor groups
%------------------------------------------------------------------
for j=1:length(Curren_drop)-1
bd=Resultado(:,1);
cd=Resultado(:,2);
if Resultado(j,6)==1
Grupo1(j)=[bd(j) cd(j)];
Grupo1(j)=Resultado(j,2);
else
Grupo1(j)=0;
end
if Resultado(j,6)==2
Grupo2(j)=Resultado(j,2);
else
Grupo2(j)=0;
end
end
%------------------------------------------------------------------
% Desition: adding new currnt sample to groups already
% classified, determines which shows less standard deviation,
% predicting to which bubble size interval the current drop
% belongs.
%------------------------------------------------------------------
for l=1:length(Curren_drop)
Nuevo_dato=Curren_drop(1);
rms1=std(Grupo1);Grupo1_1=Grupo1;
Grupo1_1(end+1)=Nuevo_dato;
rms1_1=std(Grupo1_1);
error1=abs(rms1-rms1_1);
rms2=std(Grupo2);Grupo2_2=Grupo2;
Grupo2_2(end+1)=Nuevo_dato;
rms2_2=std(Grupo2_2);
error2=abs(rms2-rms2_2);
if error1>error2
salidapredictor(1)=1;
% display('Burbuja mayor a 500 um')
else
% display('Burbuja menor a 500 um')
salidapredictor(1)=0;
end
end
```

SVM Algorithm

The SVM function could not be implemented in MATLAB for more than 2 classes. Thus, two algorithms were developed. The first one shown below detects two bubble sizes:

```
% SVM predictor for two classes
close all
clear all
clc
%----------------------------------------------------------------
% Definicion de variables
%----------------------------------------------------------------
A=xlsread('C:\Users\Andres
Saavedra\Documents\MATLAB\work\Thesis\Algoritmos
finales\Data entrenamiento\Data_input_3 features.xlsx');
Current_drop=A(:,3);
MP1=A(:,5);
MP2=A(:,6);
X=[Current_drop];
X=[Current_drop MP 1 MP2]
XTest=Current_drop;
Y=A(:,7);
%----------------------------------------------------------------
% Aplicacion de SVM
%----------------------------------------------------------------
tic
CVSVMModel=fitcsvm(X,Y)
[label,score]=predict(CVSVMModel,XTest);toc
Resultado=[XTest label];
%    xlswrite('svm_prediccion_1feature_2clases',Resultado);
%    xlswrite('svm_prediccion_3feature_2clases',Resultado);
```

In order to determine 5 classes, the next algorithm with one vs all methodology, was implemented:

```
% SVM predictor more tan two classes
% Methodology: one vs all
close all
clear all
clc
%----------------------------------------------------------------
% Variable definitions
%----------------------------------------------------------------
A=xlsread('C:\Users\Andres
Saavedra\Documents\MATLAB\work\Thesis\Algoritmos
finales\Data entrenamiento\Data_input_3 features.xlsx');
Current_drop=A(:,3);
MP1=A(:,5);
MP2=A(:,6);
X=[Current_drop];
Y=A(:,7);
XTest=Current_drop;
%----------------------------------------------------------------
% SVM multi-class, using the multisvm function
%----------------------------------------------------------------
tic
results=multi svm(TrainingSet, GroupTrain, TestSet);
toc
% xlswrite('svm_prediccion_1feature_5class',Resultado);
% xlswrite('svm_prediccion_3feature_5class',Resultado);
```

Neural Network Algorithm

The following algorithm describes the Neural Network algorithm used as previously described according to the present invention.

```
% SVM predictor more than two classes
% Methodology: one vs all
close all
clear all
clc
A=xlsread('C:\Users\Andres
Saavedra\Documents\MATLAB\work\Thesis\Algoritmos
finales\Data entrenamiento\Data_input_3 features.xlsx');
Bubble_size=A(:,2);
Current_drop=A(:,3);
MP1=A(:,5);
MP2=A(:,6);
subg1=A(:,10);subg2=A(:,11);subg3=A(:,12);subg4=A(:,13);subg5=A(:,14);
group=[subg1 subg2 subg3 subg4 subg5];
% x=[Current_drop MP1 MP2]; 3 Features
x=Current_drop;%1 feature
x=x';
t=group';
tic
% Create a Pattern Recognition Network
hiddenLayerSize=6;
net=patternnet(hiddenLayerSize);
% Setup Division of Data for Training, Validation, Testing
net.divideParam.trainRatio=70/100;
net.divideParam.valRatio=15/100;
net.divideParam.testRatio=15/100;
% Train the Network
[net,tr]=train(net,x,t);
% Test the Network
y=net(x);% Result of the networks when tested with all input data
e=gsubtract(t,y);
tind=vec2ind(t);
yind=vec2ind(y);
percentErrors=sum(tind~=yind)/numel(tind);
performance=perform(net,t,y);
toc
figure, plotconfusion(t,y)
% xlswrite('NN_prediccion_5clases_3features',y');
```

Rate of Convergence

The "TASKLIST" command was used to detect the processes used by the computer constantly. Table 23 below shows the running process in the computer when prediction algorithm was computed.

TABLE 23

| Image Name | CPU Process | Session Name | Session # | Memory Usage |
| --- | --- | --- | --- | --- |
| System Idle Process | 0 | Services | 0 | 24 k |
| System | 4 | Services | 0 | 3,580 k |
| smss.exe | 500 | Services | 0 | 1,384 K |
| csrss.exe | 656 | Services | 0 | 6,696 K |
| wininit.exe | 792 | Services | 0 | 5,188 K |
| csrss.exe | 812 | Console | 1 | 12,724 K |
| services.exe | 848 | Services | 0 | 11,968 K |
| lsass.exe | 876 | Services | 0 | 14,640 K |
| lsm.exe | 884 | Services | 0 | 4,964 K |
| winlogon.exe | 972 | Console | 1 | 8,692 K |
| svchost.exe | 380 | Services | 0 | 12,216 K |
| nvvsvc.exe | 464 | Services | 0 | 8,632 K |
| nvSCPAPISvr.exe | 524 | Services | 0 | 6,136 K |
| svchost.exe | 700 | Services | 0 | 11,420 K |
| svchost.exe | 804 | Services | 0 | 22,612 K |
| svchost.exe | 1036 | Services | 0 | 161,904 K |
| svchost.exe | 1076 | Services | 0 | 44,300 K |
| svchost.exe | 1200 | Services | 0 | 13,768 K |
| svchost.exe | 1364 | Services | 0 | 20,224 K |
| NvXDSync.exe | 1428 | Console | 1 | 22,724 K |
| nvvsvc.exe | 1440 | Console | 1 | 15,888 K |
| AvastSvc.exe | 1640 | Services | 0 | 41,412 K |
| wlanext.exe | 1648 | Services | 0 | 19,828 K |
| conhost.exe | 1656 | Services | 0 | 3,552 K |
| spoolsv.exe | 1832 | Services | 0 | 18,156 K |
| svchost.exe | 1868 | Services | 0 | 14,568 K |
| armsvc.exe | 1956 | Services | 0 | 4,192 K |
| AERTSr64.exe | 1980 | Services | 0 | 3,444 K |
| AgentHost.Service.exe | 2004 | Services | 0 | 17,500 K |

TABLE 23-continued

| Image Name | CPU Process | Session Name | Session # | Memory Usage |
|---|---|---|---|---|
| AppleMobileDeviceService.exe | 2388 | Services | 0 | 9,856 K |
| Agent.AgentHost.exe | 2408 | Services | 0 | 27,460 K |
| devmonsrv.exe | 2540 | Services | 0 | 7,088 K |
| svchost.exe | 2576 | Services | 0 | 5,852 K |
| EvtEng.exe | 2652 | Services | 0 | 17,352 K |
| hasplms.exe | 2704 | Services | 0 | 21,708 K |
| lkads.exe | 2876 | Services | 0 | 9,100 K |
| nidmsrv.exe | 2916 | Services | 0 | 9,496 K |
| SystemWebServer.exe | 2960 | Services | 0 | 10,616 K |
| rndlresolversvc.exe | 3024 | Services | 0 | 4,204 K |
| RegSrvc.exe | 2136 | Services | 0 | 9,088 K |
| SftService.exe | 2696 | Services | 0 | 10,032 K |
| taskhost.exe | 2712 | Console | 1 | 9,920 K |
| svchost.exe | 3124 | Services | 0 | 6,840 K |
| dwm.exe | 3200 | Console | 1 | 10,624 K |
| SupportAssistAgent.exe | 3208 | Services | 0 | 42,360 K |
| explorer.exe | 3232 | Console | 1 | 93,368 K |
| Toaster.exe | 3456 | Console | 1 | 52,056 K |
| TeamViewer_Service.exe | 4080 | Services | 0 | 14,436 K |
| WLIDSVC.EXE | 2284 | Services | 0 | 12,532 K |
| ZeroConfigService.exe | 4128 | Services | 0 | 17,840 K |
| RtkNGUI64.exe | 4324 | Console | 1 | 13,276 K |
| obexsrv.exe | 4384 | Services | 0 | 7,512 K |
| nvtray.exe | 4400 | Console | 1 | 35,472 K |
| hkcmd.exe | 4436 | Console | 1 | 8,828 K |
| igfxpers.exe | 4452 | Console | 1 | 12,804 K |
| lkcitdl.exe | 4572 | Services | 0 | 9,812 K |
| Apoint.exe | 4632 | Console | 1 | 12,896 K |
| rundll32.exe | 4724 | Console | 1 | 11,180 K |
| quickset.exe | 4924 | Console | 1 | 14,560 K |
| WLIDSVCM.EXE | 5056 | Services | 0 | 4,756 K |
| lktsrv.exe | 4424 | Services | 0 | 9,716 K |
| unsecapp.exe | 4660 | Services | 0 | 6,788 K |
| ApplicationWebServer.exe | 4824 | Services | 0 | 9,108 K |
| WmiPrvSE.exe | 1348 | Services | 0 | 14,644 K |
| nmsrvc.exe | 5424 | Services | 0 | 8,492 K |
| WmiPrvSE.exe | 5956 | Services | 0 | 27,532 K |
| GoogleUpdate.exe | 5488 | Console | 1 | 528 K |
| ISUSPM.exe | 5548 | Console | 1 | 7,964 K |
| SearchIndexer.exe | 3108 | Services | 0 | 59,772 K |
| WebcamDell2.exe | 6192 | Console | 1 | 9,836 K |
| ApMsgFwd.exe | 6388 | Console | 1 | 8,616 K |
| mediasrv.exe | 6456 | Services | 0 | 8,600 K |
| AvastVBoxSVC.exe | 6604 | Services | 0 | 12,276 K |
| btplayerctrl.exe | 6684 | Console | 1 | 7,004 K |
| ApntEx.exe | 6748 | Console | 1 | 8,120 K |
| hidfind.exe | 6764 | Console | 1 | 7,192 K |
| conhost.exe | 6824 | Console | 1 | 5,668 K |
| SweetPacksUpdateManager.exe | 6856 | Console | 1 | 10,280 K |
| nmctxth.exe | 6892 | Console | 1 | 15,276 K |
| realsched.exe | 7036 | Console | 1 | 412 K |
| AgentHost.UI.exe | 7052 | Console | 1 | 42,000 K |
| svchost.exe | 7096 | Services | 0 | 6,632 K |
| svchost.exe | 6320 | Services | 0 | 45,132 K |
| avastui.exe | 1380 | Console | 1 | 25,660 K |
| ngservice.exe | 6536 | Services | 0 | 4,592 K |
| unsecapp.exe | 3652 | Console | 1 | 8,692 K |
| SearchProtocolHost.exe | 5596 | Services | 0 | 8,984 K |
| BTHSAmpPalService.exe | 3112 | Services | 0 | 6,048 K |
| BTHSSecurityMgr.exe | 2804 | Services | 0 | 10,652 K |
| DellDataVaultWiz.exe | 5552 | Services | 0 | 12,152 K |
| MATLAB.exe | 6172 | Console | 1 | 465,244 K |
| LMS.exe | 6408 | Services | 0 | 5,272 K |
| NASvc.exe | 6704 | Services | 0 | 6,928 K |
| svchost.exe | 6300 | Services | 0 | 23,748 K |
| wmpnetwk.exe | 6156 | Services | 0 | 9,960 K |
| DellDataVault.exe | 5876 | Services | 0 | 11,740 K |
| UNS.exe | 4184 | Services | 0 | 8,068 K |
| WmiApSrv.exe | 1132 | Services | 0 | 7,636 K |
| cmd.exe | 6888 | Console | 1 | 4,488 K |
| conhost.exe | 4244 | Console | 1 | 6,720 K |
| SearchFilterHost.exe | 4300 | Services | 0 | 6,664 K |
| tasklist.exe | 7956 | Console | 1 | 8,860 K |

The total CPU process is 368192. The specification for the computer to millions instructions per seconds (MIPS) is 128300. This establishes that the time count for each generating MATLAB algorithm presents additional time of about 3 pec. If the algorithms are being used by the computer, it would be negligible. However, considering the hardware devices currently available to build a portable system, the information in Table 24 below comparing the time of convergence to classifiers in different hardware devices must be consider:

TABLE 24

| | | | | Time of convergence [sec] | | | |
|---|---|---|---|---|---|---|---|
| Algorithm | Features | Classes | Iterations | PC | PIC | DSP | FPGA |
| K-mean | 1 | 2 | 4 | 0.14 | 449.1 | 2.0 | 18.0 |
| SVM | 1 | 2 | 14 | 1.20 | 3849.0 | 17.5 | 154.0 |
| NN | 1 | 2 | 22 | 1.76 | 5645.2 | 25.7 | 225.0 |
| K-mean | 1 | 5 | 5 | 0.16 | 513.2 | 2.3 | 20.5 |
| SVM | 1 | 5 | 29 | 1.84 | 5901.8 | 26.8 | 236.1 |
| NN | 1 | 5 | 19 | 1.78 | 5709.4 | 26.0 | 228.4 |
| K-mean | 3 | 2 | 8 | 0.15 | 481.1 | 2.2 | 19.2 |
| SVM | 3 | 2 | 21 | 1.34 | 4298.1 | 19.5 | 171.9 |
| NN | 3 | 2 | 34 | 1.83 | 5869.7 | 26.7 | 234.8 |
| K-mean | 3 | 5 | 7 | 0.16 | 513.2 | 2.3 | 20.5 |
| SVM | 3 | 5 | 27 | 1.84 | 5901.8 | 26.8 | 236.1 |
| NN | 3 | 5 | 133 | 2.03 | 6511.2 | 29.6 | 260.4 |

The following devices were used with this technical specifications: PIC "18F452" with 40 MIPS (Microchip, 2002), DSP "TMS320DM647" with 8800 MIPS (TI, 2012), and FPGA Stratix 10 with 1000 MIPS (Altera, 2015).

Although the present invention has been described herein with reference to the foregoing exemplary embodiment, this embodiment does not serve to limit the scope of the present invention. Accordingly, those skilled in the art to which the present invention pertains will appreciate that various modifications are possible, without departing from the technical spirit of the present invention.

We claim:

1. A system for real-time monitoring the amount and size of bubbles within an enclosed medium, said system comprising:
   a piezoelectric element configured to surround said enclosed medium;
   a plurality of transducers;
   processing unit electrically connected to said piezoelectric element and said plurality of transducers, wherein said processing unit comprises:
   a resonant frequency module that determines the resonant frequency within said enclosed medium based on electrical signals received from said piezoelectric element in order to generate a resonant electrical signal having a frequency equal to said resonant frequency and exciting said enclosed medium with said generated resonant electrical signal via said piezoelectric element;
   a monitoring module that measures electrical signals from said piezoelectric element and said plurality of transducers;
   an extraction module that establishes a relationship between said measured electrical signals and the amount and size of said bubbles;
   a classifier module that receives data from said monitoring module, said data indicative of at least one of: the amount and size of said bubbles determined from said piezoelectric element and said plurality of transducers, wherein said classifier module further classifies said received data into different categories of said received data in order to determine the amount and size of bubbles within said enclosed medium.

2. The system of claim 1, wherein said enclosed medium comprises a body part of a user having bloodstream and/or tissues.

3. The system of claim 1, wherein said plurality of transducers comprises a plurality of pill microphones.

4. The system of claim 1, wherein said resonant frequency module determines the resonant frequency within said enclosed medium by acquiring current and voltage signals on said piezoelectric element and determining the electrical admittance on the piezoelectric element as a function of frequency.

5. The system of claim 1, wherein said exciting generated resonant electrical signal allows said piezoelectric element to resonate at the same resonant frequency within said enclosed medium.

6. The system of claim 5, wherein the presence of bubbles is determined by measuring a disturbance of said resonant frequency.

7. The system of claim 1, wherein the measured electrical signals from said piezoelectric element and said plurality of transducers are current and voltage electrical signals.

8. The system of claim 7, wherein the relationship between said current and voltage electrical signals and the amount and size of said bubbles is determined by calculating current and voltage relative values from a plurality of current and voltage measurements taken from said piezoelectric element and said plurality of transducers and associating said relative values to the amount and size of said bubbles.

9. The system of claim 1, wherein said categories comprise different bubble sizes that are categorized from data associated from measurements of at least one of: said piezoelectric element and said plurality of transducers.

10. The system of claim 9, wherein said classifier module determines the amount and size of bubbles within said enclosed medium by applying on said data at least one of: a Support Vector Machines classifier method, an Artificial Neural Networks classifier method and a K-mean classifier method.

11. The system of claim 2, wherein said body part is a user's thigh.

12. A method for real-time monitoring of an amount and size of bubbles within an enclosed medium, said method comprising:
determining a resonant frequency within said enclosed medium;
generating an electrical signal having a frequency equal to said detected resonant frequency and exciting said enclosed medium with said generated signal via a piezoelectric element;
measuring electrical signals from at least one of: said piezoelectric element and a plurality of transducers;
establishing a relationship between said measured electrical signals and the amount and size of said bubbles;
generating data indicative of at least one of: the amount and size of said bubbles based on the established relationship;
classifying said generated data into different categories of said generated data;
determining the presence and size of bubbles within said enclosed medium based on the classification results of said generated data categories.

13. The method of claim 12, wherein said resonant frequency is determined by acquiring current and voltage signals on said piezoelectric element and determining the electrical admittance on the piezoelectric element as a function of frequency.

14. The method of claim 12, wherein the measured electrical signals from said piezoelectric element and said plurality of transducers are current and voltage electrical signals.

15. The method of claim 12, wherein the relationship between said measured electrical signals and the amount and size of said bubbles is determined by calculating current and voltage relative values from a plurality of current and voltage measurements taken from said piezoelectric element and said plurality of transducers and associating said relative values to the amount and size of said bubbles.

16. The method of claim 12, wherein said data generated corresponds to measurements made from said at least one of: the piezoelectric element and the plurality of transducers.

17. The method of claim 12, wherein said categories comprise different bubble sizes that are categorized from data associated from measurements of at least one of: said piezoelectric element and said plurality of transducers.

18. The method of claim 12, wherein the amount and size of bubbles within the enclosed medium is determined by applying on said data at least one of: a Support Vector Machines classifier method, an Artificial Neural Networks classifier method and a K-mean classifier method.

19. The method of claim 12, wherein said enclosed medium comprises a body part of a user having bloodstream and/or tissues.

20. The method of claim 19, wherein said body part is a user's thigh.

* * * * *